US011535668B2

(12) United States Patent
Baeuerle et al.

(10) Patent No.: US 11,535,668 B2
(45) Date of Patent: Dec. 27, 2022

(54) INDUCIBLE MONOVALENT ANTIGEN BINDING PROTEIN

(71) Applicant: Harpoon Therapeutics, Inc., South San Francisco, CA (US)

(72) Inventors: Patrick Baeuerle, South San Francisco, CA (US); Holger Wesche, South San Francisco, CA (US)

(73) Assignee: HARPOON THERAPEUTICS, INC., South San Francisco, CA (US)

(*) Notice: Subject to any disclaimer, the term of this patent is extended or adjusted under 35 U.S.C. 154(b) by 218 days.

(21) Appl. No.: 16/489,523

(22) PCT Filed: Feb. 28, 2018

(86) PCT No.: PCT/US2018/020307
§ 371 (c)(1),
(2) Date: Aug. 28, 2019

(87) PCT Pub. No.: WO2018/160754
PCT Pub. Date: Sep. 7, 2018

(65) Prior Publication Data
US 2020/0148771 A1  May 14, 2020

Related U.S. Application Data

(60) Provisional application No. 62/465,000, filed on Feb. 28, 2017.

(51) Int. Cl.
C07K 16/28 (2006.01)

(52) U.S. Cl.
CPC ...... *C07K 16/2818* (2013.01); *C07K 16/2878* (2013.01); *C07K 2317/35* (2013.01); *C07K 2317/524* (2013.01); *C07K 2317/526* (2013.01); *C07K 2317/565* (2013.01); *C07K 2317/622* (2013.01); *C07K 2317/75* (2013.01); *C07K 2317/92* (2013.01); *C07K 2319/50* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,943,533 A | 7/1990 | Mendelsohn et al. |
| 5,061,620 A | 10/1991 | Tsukamoto et al. |
| 5,199,942 A | 4/1993 | Gillis |
| 5,225,539 A | 7/1993 | Winter |
| 5,350,674 A | 9/1994 | Boenisch et al. |
| 5,399,346 A | 3/1995 | Anderson et al. |
| 5,530,101 A | 6/1996 | Queen et al. |
| 5,565,332 A | 10/1996 | Hoogenboom et al. |
| 5,580,859 A | 12/1996 | Felgner et al. |
| 5,585,089 A | 12/1996 | Queen et al. |
| 5,585,362 A | 12/1996 | Wilson et al. |
| 5,589,466 A | 12/1996 | Felgner et al. |
| 5,759,808 A | 6/1998 | Casterman et al. |
| 5,766,886 A | 6/1998 | Studnicka et al. |
| 5,773,292 A | 6/1998 | Bander |
| 5,800,988 A | 9/1998 | Casterman et al. |
| 5,840,526 A | 11/1998 | Casterman et al. |
| 5,844,093 A | 12/1998 | Kettleborough et al. |
| 5,858,358 A | 1/1999 | June et al. |
| 5,859,205 A | 1/1999 | Adair et al. |
| 5,874,541 A | 2/1999 | Casterman et al. |
| 5,883,223 A | 3/1999 | Gray |
| 6,005,079 A | 12/1999 | Casterman et al. |
| 6,015,695 A | 1/2000 | Casterman et al. |
| 6,107,090 A | 8/2000 | Bander |
| 6,120,766 A | 9/2000 | Hale et al. |
| 6,136,311 A | 10/2000 | Bander |
| 6,326,193 B1 | 12/2001 | Liu et al. |
| 6,331,415 B1 | 12/2001 | Cabilly et al. |
| 6,352,694 B1 | 3/2002 | June et al. |
| 6,407,213 B1 | 6/2002 | Carter et al. |
| 6,534,055 B1 | 3/2003 | June et al. |
| 6,548,640 B1 | 4/2003 | Winter |
| 6,670,453 B2 | 12/2003 | Frenken et al. |
| 6,692,964 B1 | 2/2004 | June et al. |
| 6,759,518 B1 | 7/2004 | Kontermann et al. |
| 6,767,711 B2 | 7/2004 | Bander |
| 6,797,514 B2 | 9/2004 | Berenson et al. |
| 6,867,041 B2 | 3/2005 | Berenson et al. |

(Continued)

FOREIGN PATENT DOCUMENTS

| | | |
|---|---|---|
| CN | 1563092 A | 1/2005 |
| CN | 101646689 A | 2/2010 |

(Continued)

OTHER PUBLICATIONS

Annual Report Pursuant to Section 13 or 15(d) of the Securities Exchange Act of 1934. 2019 22-24 [online]. [Retrieved on Aug. 5, 2021]. Retrieved from website URL:https://www.annualreports.com/HostedData/AnnualReportArchive/h/NASDAQ_HARP_2018.pdf.

Brauchle et al. Characterization of a Novel FLT3 BiTE Molecule for the Treatment of Acute Myeloid Leukemia. Mol Cancer Ther 19:1875-88 (2020).

Glaser et al. Novel antibody hinge regions for efficient production of CH2 domain-deleted antibodies. J. Biol. Chem. 280:41494-503 (2005).

Halaby et al. The immunoglobulin fold family: sequence analysis and 3D structure comparisons. Prot Eng 12(7):563-571 (1999).

(Continued)

*Primary Examiner* — Phillip Gambel
(74) *Attorney, Agent, or Firm* — Wilson Sonsini Goodrich & Rosati

(57) ABSTRACT

Disclosed herein are inducible monovalent target-binding proteins which are activated upon protease cleavage. Pharmaceutical compositions comprising the binding proteins disclosed herein and methods of using such formulations are further provided.

20 Claims, 5 Drawing Sheets
Specification includes a Sequence Listing.

(56) References Cited

U.S. PATENT DOCUMENTS

| | | |
|---|---|---|
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,060,808 B1 | 6/2006 | Goldstein et al. |
| 7,067,318 B2 | 6/2006 | June et al. |
| 7,144,575 B2 | 12/2006 | June et al. |
| 7,163,680 B2 | 1/2007 | Bander |
| 7,172,869 B2 | 2/2007 | June et al. |
| 7,175,843 B2 | 2/2007 | June et al. |
| 7,232,566 B2 | 6/2007 | June et al. |
| 7,247,301 B2 | 7/2007 | Van De Winkel et al. |
| 7,262,276 B2 | 8/2007 | Huang et al. |
| 7,595,378 B2 | 9/2009 | Van De Winkel et al. |
| 7,666,414 B2 | 2/2010 | Bander |
| 7,723,484 B2 | 5/2010 | Beidler et al. |
| 7,807,162 B2 | 10/2010 | Silence |
| 7,850,971 B2 | 12/2010 | Maddon et al. |
| 7,939,072 B2 | 5/2011 | Yarden et al. |
| 8,114,965 B2 | 2/2012 | Maddon et al. |
| 8,188,223 B2 | 5/2012 | Beirnaert et al. |
| 8,236,308 B2 | 8/2012 | Kischel et al. |
| 8,470,330 B2 | 6/2013 | Schuelke et al. |
| 8,623,356 B2 | 1/2014 | Christopherson et al. |
| 8,629,244 B2 | 1/2014 | Kolkman et al. |
| 8,703,135 B2 | 4/2014 | Beste et al. |
| 8,784,821 B1 | 7/2014 | Kufer et al. |
| 8,846,042 B2 | 9/2014 | Zhou |
| 8,907,071 B2 | 12/2014 | Sullivan et al. |
| 8,937,164 B2 | 1/2015 | Descamps et al. |
| 9,169,316 B2 | 10/2015 | Baty et al. |
| 9,309,327 B2 | 4/2016 | Humphreys et al. |
| 9,327,022 B2 | 5/2016 | Zhang et al. |
| 9,340,621 B2 | 5/2016 | Kufer et al. |
| 9,708,412 B2 | 7/2017 | Baeuerle et al. |
| 9,920,115 B2 | 3/2018 | Dubridge et al. |
| 10,066,016 B2 | 9/2018 | Dubridge et al. |
| 10,100,106 B2 | 10/2018 | Dubridge et al. |
| 10,428,120 B2 | 10/2019 | Kontermann et al. |
| 11,180,563 B2 | 11/2021 | Wesche et al. |
| 2002/0015704 A1 | 2/2002 | Bander |
| 2002/0051780 A1 | 5/2002 | Lindhofer et al. |
| 2003/0031673 A1 | 2/2003 | Bander |
| 2003/0092892 A1 | 5/2003 | Frenken et al. |
| 2004/0101519 A1 | 5/2004 | June et al. |
| 2005/0042664 A1 | 2/2005 | Wu et al. |
| 2005/0048617 A1 | 3/2005 | Wu et al. |
| 2005/0100543 A1 | 5/2005 | Hansen et al. |
| 2005/0175606 A1 | 8/2005 | Huang et al. |
| 2006/0034810 A1 | 2/2006 | Riley et al. |
| 2006/0046971 A1 | 3/2006 | Stuhler et al. |
| 2006/0121005 A1 | 6/2006 | Berenson et al. |
| 2006/0228364 A1 | 10/2006 | Dennis et al. |
| 2006/0252096 A1 | 11/2006 | Zha et al. |
| 2007/0014794 A1 | 1/2007 | Carter et al. |
| 2007/0178082 A1 | 8/2007 | Silence et al. |
| 2007/0269422 A1 | 11/2007 | Beirnaert et al. |
| 2008/0069772 A1 | 3/2008 | Stuhler et al. |
| 2008/0260757 A1 | 10/2008 | Holt et al. |
| 2009/0028880 A1 | 1/2009 | Beirnaert et al. |
| 2009/0252683 A1 | 10/2009 | Kischel et al. |
| 2009/0259026 A1 | 10/2009 | Tomlinson et al. |
| 2010/0022452 A1 | 1/2010 | Silence |
| 2010/0122358 A1 | 5/2010 | Brueggemann et al. |
| 2010/0150918 A1 | 6/2010 | Kufer et al. |
| 2010/0166734 A1 | 7/2010 | Dolk |
| 2010/0189651 A1 | 7/2010 | Stagliano et al. |
| 2010/0189727 A1 | 7/2010 | Rodeck et al. |
| 2010/0266531 A1 | 10/2010 | Hsieh et al. |
| 2010/0291112 A1 | 11/2010 | Kellner et al. |
| 2010/0311119 A1 | 12/2010 | Hermans et al. |
| 2011/0129458 A1 | 6/2011 | Dolk et al. |
| 2011/0165621 A1 | 7/2011 | Dreier et al. |
| 2011/0262439 A1 | 10/2011 | Kufer et al. |
| 2011/0275787 A1 | 11/2011 | Kufer et al. |
| 2011/0313135 A1 | 12/2011 | Vanhove et al. |
| 2012/0039899 A1 | 2/2012 | Olsen et al. |
| 2012/0231024 A1 | 9/2012 | Elsaesser-Beile et al. |
| 2012/0237977 A1* | 9/2012 | Daugherty ............ A61P 43/00 435/69.6 |
| 2012/0328619 A1 | 12/2012 | Fey et al. |
| 2013/0017200 A1 | 1/2013 | Scheer et al. |
| 2013/0136744 A1 | 5/2013 | Bouche et al. |
| 2013/0197201 A1 | 8/2013 | Vasquez et al. |
| 2013/0266568 A1 | 10/2013 | Brinkmann et al. |
| 2013/0267686 A1 | 10/2013 | Brinkmann et al. |
| 2013/0273055 A1 | 10/2013 | Borges et al. |
| 2013/0330335 A1 | 12/2013 | Bremel et al. |
| 2014/0004121 A1 | 1/2014 | Fanslow, III et al. |
| 2014/0023664 A1 | 1/2014 | Lowman et al. |
| 2014/0045195 A1 | 2/2014 | Daugherty et al. |
| 2014/0073767 A1 | 3/2014 | Lee et al. |
| 2014/0088295 A1 | 3/2014 | Smith et al. |
| 2014/0205601 A1 | 7/2014 | Beirnaert et al. |
| 2014/0242075 A1 | 8/2014 | Parren et al. |
| 2014/0302037 A1 | 10/2014 | Borges et al. |
| 2014/0322218 A1 | 10/2014 | Xiao et al. |
| 2015/0037334 A1 | 2/2015 | Kufer et al. |
| 2015/0056206 A1 | 2/2015 | Zhou |
| 2015/0064169 A1 | 3/2015 | Wang et al. |
| 2015/0079088 A1 | 3/2015 | Lowman et al. |
| 2015/0079093 A1 | 3/2015 | Stuhler |
| 2015/0093336 A1 | 4/2015 | Van Ginderachter et al. |
| 2015/0174268 A1 | 6/2015 | Li et al. |
| 2015/0183875 A1 | 7/2015 | Cobbold et al. |
| 2015/0232557 A1 | 8/2015 | Tan et al. |
| 2015/0274836 A1 | 10/2015 | Ho et al. |
| 2015/0274844 A1 | 10/2015 | Blankenship et al. |
| 2016/0017058 A1 | 1/2016 | Kim et al. |
| 2016/0024174 A1 | 1/2016 | Odunsi et al. |
| 2016/0032011 A1 | 2/2016 | Zhang et al. |
| 2016/0032019 A1 | 2/2016 | Xiao et al. |
| 2016/0039942 A1 | 2/2016 | Cobbold et al. |
| 2016/0068605 A1 | 3/2016 | Nemeth et al. |
| 2016/0115241 A1 | 4/2016 | Yan et al. |
| 2016/0130331 A1 | 5/2016 | Stull et al. |
| 2016/0215063 A1 | 7/2016 | Bernett et al. |
| 2016/0229913 A1* | 8/2016 | Bosques ............... C07K 16/00 |
| 2016/0251440 A1 | 9/2016 | Roobrouck et al. |
| 2016/0257721 A1 | 9/2016 | Lieber et al. |
| 2016/0319040 A1 | 11/2016 | Dreier et al. |
| 2016/0340444 A1 | 11/2016 | Baeuerle et al. |
| 2016/0355842 A1 | 12/2016 | Parks et al. |
| 2017/0029502 A1 | 2/2017 | Raum et al. |
| 2017/0037149 A1 | 2/2017 | Raum et al. |
| 2017/0152316 A1 | 6/2017 | Cobbold et al. |
| 2017/0158771 A1* | 6/2017 | Glennie ............... A61P 37/00 |
| 2017/0204164 A1 | 7/2017 | Himmler et al. |
| 2017/0275373 A1 | 9/2017 | Kufer et al. |
| 2017/0298149 A1 | 10/2017 | Baeuerle et al. |
| 2017/0334997 A1 | 11/2017 | Dubridge et al. |
| 2017/0362310 A1 | 12/2017 | Shoemaker |
| 2017/0369563 A1 | 12/2017 | Dubridge et al. |
| 2018/0016323 A1 | 1/2018 | Brandenburg et al. |
| 2018/0134789 A1 | 5/2018 | Baeuerle et al. |
| 2018/0148508 A1 | 5/2018 | Wang et al. |
| 2018/0161428 A1 | 6/2018 | Dubridge et al. |
| 2018/0162949 A1 | 6/2018 | Baeuerle et al. |
| 2018/0326060 A1 | 11/2018 | Wesche et al. |
| 2018/0327508 A1 | 11/2018 | Wesche et al. |
| 2018/0346601 A1 | 12/2018 | Dettling et al. |
| 2019/0031749 A1 | 1/2019 | Dubridge et al. |
| 2019/0092862 A1 | 3/2019 | Cui et al. |
| 2019/0112381 A1 | 4/2019 | Wesche et al. |
| 2019/0135930 A1 | 5/2019 | Wesche et al. |
| 2019/0225702 A1 | 7/2019 | Baeuerle et al. |
| 2020/0095340 A1 | 3/2020 | Wesche et al. |
| 2020/0115461 A1 | 4/2020 | Evnin et al. |
| 2020/0231672 A1 | 7/2020 | Dubridge et al. |
| 2020/0270362 A1 | 8/2020 | Wesche et al. |
| 2020/0289646 A1 | 9/2020 | Wesche et al. |
| 2021/0047439 A1 | 2/2021 | Wesche et al. |
| 2021/0095047 A1 | 4/2021 | Baeuerle et al. |
| 2021/0100902 A1 | 4/2021 | Dubridge et al. |

(56) References Cited

U.S. PATENT DOCUMENTS

| | | |
|---|---|---|
| 2021/0171649 A1 | 6/2021 | Wesche et al. |
| 2021/0179735 A1 | 6/2021 | Baeuerle et al. |
| 2021/0269530 A1 | 9/2021 | Lin et al. |
| 2021/0284728 A1 | 9/2021 | Lin et al. |
| 2021/0292421 A1 | 9/2021 | Lin et al. |
| 2021/0355219 A1 | 11/2021 | Lin et al. |
| 2022/0017626 A1 | 1/2022 | Wesche et al. |
| 2022/0054544 A1 | 2/2022 | Lin et al. |
| 2022/0098311 A1 | 3/2022 | Wesche et al. |
| 2022/0112297 A1 | 4/2022 | Wesche et al. |

FOREIGN PATENT DOCUMENTS

| | | |
|---|---|---|
| CN | 105968201 A | 9/2016 |
| CN | 105968204 A | 9/2016 |
| CN | 109593786 A | 4/2019 |
| EP | 0239400 A2 | 9/1987 |
| EP | 0519596 A1 | 12/1992 |
| EP | 0592106 A1 | 4/1994 |
| EP | 1378520 A1 | 1/2004 |
| EP | 1736484 A1 | 12/2006 |
| EP | 2336179 A1 | 6/2011 |
| FR | 901228 A | 7/1945 |
| JP | 2005501517 A | 1/2005 |
| JP | 2005518789 A | 6/2005 |
| JP | 2016500655 A | 1/2016 |
| JP | 2019052750 A | 4/2019 |
| WO | WO-9109967 A1 | 7/1991 |
| WO | WO-9307105 A1 | 4/1993 |
| WO | WO-9404678 A1 | 3/1994 |
| WO | WO-9937681 A2 | 7/1999 |
| WO | WO-0043507 A1 | 7/2000 |
| WO | WO-0190190 A2 | 11/2001 |
| WO | WO-0196584 A2 | 12/2001 |
| WO | WO-02085945 A2 | 10/2002 |
| WO | WO-03025020 A1 | 3/2003 |
| WO | WO-03035694 A2 | 5/2003 |
| WO | WO-03064606 A2 | 8/2003 |
| WO | WO-2004003019 A2 | 1/2004 |
| WO | WO-2004041867 A2 | 5/2004 |
| WO | WO-2004042404 A1 | 5/2004 |
| WO | WO-2004049794 A2 | 6/2004 |
| WO | WO-2004099249 A2 | 11/2004 |
| WO | WO-2006020258 A2 | 2/2006 |
| WO | WO-2006122787 A1 | 11/2006 |
| WO | WO-2007024715 A2 | 3/2007 |
| WO | WO-2007042261 A2 | 4/2007 |
| WO | WO-2007062466 A1 | 6/2007 |
| WO | WO-2007115230 A2 | 10/2007 |
| WO | WO-2008028977 A2 | 3/2008 |
| WO | WO-2009025846 A2 | 2/2009 |
| WO | WO-2009030285 A1 | 3/2009 |
| WO | WO-2009147248 A2 | 12/2009 |
| WO | WO-2010003118 A1 | 1/2010 |
| WO | WO-2010037836 A2 | 4/2010 |
| WO | WO-2010037837 A2 | 4/2010 |
| WO | WO-2010081173 A2 | 7/2010 |
| WO | WO-2011039368 A2 | 4/2011 |
| WO | WO-2011051327 A2 | 5/2011 |
| WO | WO-2011117423 A1 | 9/2011 |
| WO | WO-2012131053 A1 | 10/2012 |
| WO | WO-2012138475 A1 | 10/2012 |
| WO | WO-2012158818 A2 | 11/2012 |
| WO | WO-2012163805 A1 | 12/2012 |
| WO | WO-2012175400 A1 | 12/2012 |
| WO | WO-2013036130 A1 | 3/2013 |
| WO | WO-2013072406 A1 | 5/2013 |
| WO | WO-2013072415 A1 | 5/2013 |
| WO | WO-2013104804 A2 | 7/2013 |
| WO | WO-2013110531 A1 | 8/2013 |
| WO | WO-2013126712 A1 | 8/2013 |
| WO | WO-2013128027 A1 | 9/2013 |
| WO | WO-2013128194 A1 | 9/2013 |
| WO | WO-2014033304 A2 | 3/2014 |
| WO | WO-2014047231 A1 | 3/2014 |
| WO | WO-2014052064 A1 | 4/2014 |
| WO | WO-2014138306 A1 | 9/2014 |
| WO | WO-2014140358 A1 | 9/2014 |
| WO | WO-2014144689 A1 | 9/2014 |
| WO | WO-2014151910 A1 | 9/2014 |
| WO | WO-2015103072 A1 | 7/2015 |
| WO | WO-2015146437 A1 | 10/2015 |
| WO | WO-2015150447 A1 | 10/2015 |
| WO | WO-2015184207 A1 | 12/2015 |
| WO | WO-2016009029 A1 | 1/2016 |
| WO | WO-2016034044 A1 | 3/2016 |
| WO | WO-2016046778 A2 | 3/2016 |
| WO | WO-2016055551 A1 | 4/2016 |
| WO | WO-2016087531 A1 | 6/2016 |
| WO | WO-2016105450 A2 | 6/2016 |
| WO | WO-2016130819 A2 | 8/2016 |
| WO | WO-2016171999 A2 | 10/2016 |
| WO | WO-2016179003 A1 | 11/2016 |
| WO | WO-2016182064 A1 | 11/2016 |
| WO | WO-2016187101 A2 | 11/2016 |
| WO | WO-2016187594 A1 | 11/2016 |
| WO | WO-2016210447 A1 | 12/2016 |
| WO | WO-2017021356 A1 | 2/2017 |
| WO | WO-2017025038 A1 | 2/2017 |
| WO | WO-2017025698 A1 | 2/2017 |
| WO | WO-2017027392 A1 | 2/2017 |
| WO | WO-2017031104 A1 | 2/2017 |
| WO | WO-2017041749 A1 | 3/2017 |
| WO | WO-2017079528 A1 | 5/2017 |
| WO | WO-2017134134 A1 | 8/2017 |
| WO | WO-2017136549 A1 | 8/2017 |
| WO | WO-2017156178 A1 | 9/2017 |
| WO | WO-2017161206 A1 | 9/2017 |
| WO | WO-2018017863 A1 | 1/2018 |
| WO | WO-2018026953 A1 | 2/2018 |
| WO | WO-2018067993 A1 | 4/2018 |
| WO | WO-2018071777 A1 | 4/2018 |
| WO | WO-2018083204 A1 | 5/2018 |
| WO | WO-2018098354 A1 | 5/2018 |
| WO | WO-2018098356 A1 | 5/2018 |
| WO | WO-2018133877 A1 | 7/2018 |
| WO | WO-2018136725 A1 | 7/2018 |
| WO | WO-2018160671 A1 | 9/2018 |
| WO | WO-2018160754 A2 | 9/2018 |
| WO | WO-2018165619 A1 | 9/2018 |
| WO | WO-2018204717 A1 | 11/2018 |
| WO | WO-2018209298 A1 | 11/2018 |
| WO | WO-2018209304 A1 | 11/2018 |
| WO | WO-2018232020 A1 | 12/2018 |
| WO | WO-2019025983 A1 | 2/2019 |
| WO | WO-2019075359 A1 | 4/2019 |
| WO | WO-2019075378 A1 | 4/2019 |
| WO | WO-2019222278 A1 | 11/2019 |
| WO | WO-2019222282 A1 | 11/2019 |
| WO | WO-2019222283 A1 | 11/2019 |
| WO | WO-2019229701 A2 | 12/2019 |
| WO | WO-2020060593 A1 | 3/2020 |
| WO | WO-2020061482 A1 | 3/2020 |
| WO | WO-2020061526 A1 | 3/2020 |
| WO | WO-2020069028 A1 | 4/2020 |
| WO | WO-2020232303 A1 | 11/2020 |
| WO | WO-2021097060 A1 | 5/2021 |
| WO | WO-2021168303 A1 | 8/2021 |
| WO | WO-2021231434 A1 | 11/2021 |

OTHER PUBLICATIONS

Han et al. Masked Chimeric Antigen Receptor for Tumor-Specific Activation. Molecular Therapy 25(1):274-284 (2017).

Hassanzadeh-Ghassabeh et al. Nanobodies and their potential applications. Nanomedicine 8(6):1013-1026 (2013).

Huck et al. Sequence of a human immunoglobulin gamma 3 heavy chain constant region gene: comparison with the other human C gamma genes. Nucl. Acids Res. 14:1779-89 (1986).

Julian et al. Efficient affinity maturation of antibody variable domains requires co-selection of compensatory mutations to maintain thermodynamic stability. Sci Rep 7:45259 (2017).

(56) References Cited

OTHER PUBLICATIONS

Škrlec et al. Non-immunoglobulin scaffolds: a focus on their targets. Trends in Biotechnol 33:408-418 (2015).
Krzywinska et al. CD45 Isoform Profile Identifies Natural Killer (NK) Subsets with Differential Activity. PLoS One 11(4):e0150434 (2016).
Leibl et al. Ovarian granulosa cell tumors frequently express EGFR (Her-1), Her-3, and Her-4: An immunohistochemical study. Gynecol Oncol 101(1):18-23 (2006).
Mason et al. CD79a: a novel marker for B-cell neoplasms in routinely processed tissue samples. Blood 86(4):1453-1459 (1995).
PCT/US2020/060184 International Search Report and Written Opinion dated Mar. 4, 2021.
PCT/US2021/018853 International Search Report and Written Opinion dated Jul. 8, 2021.
PCT/US2021/031790 International Search Report and Written Opinion dated Sep. 16, 2021.
Sandler et al. Nondermatologic adverse events associated with anti-EGFR therapy. Oncology (Williston Park) 20(5 Suppl 2):35-40 (2006).
Sheng et al. Novel Transgenic Mouse Model for Studying Human Serum Albumin as a Biomarker of Carcinogenic Exposure. Chem. Res. Toxicol. 29(5):797-809 (2016).
Stehle et al. Albumin-based drug carriers: comparison between serum albumins of different species on pharmacokinetics and tumor uptake of the conjugate. Anticancer Drugs. 10(8):785-90 (1999).
Stirewalt et al. The role of FLT3 in haematopoietic malignancies. Nat Rev Cancer 3:650-665 (2003).
Tan et al. Influence of the hinge region on complement activation, C1q binding, and segmental flexibility in chimeric human immunoglobulins. PNAS USA 87:162-166 (1990).
Thomas. Cetuximab: adverse event profile and recommendations for toxicity management. Clin J Oncol Nurs. 9(3):332-8 (2005).
UniProtKB Accession No. A0A3M1V7M7_9EURY, lg-like_bact domain-containing protein, Feb. 13, 2019 [online] [Retrieved on Jun. 8, 2021]. Retrieved from the internet <url:<ahref"https://www.uniprotorg/uniprot/A0A3M1V7M7.bct">https://www.uniprotorg/uniprot/A0A3M1V7M7.bct</url:.<a>.
U.S. Appl. No. 16/159,554 Office Action dated Mar. 16, 2021.
U.S. Appl. No. 16/161,986 Office Action dated Dec. 2, 2021.
Agata et al. Expression of the PD-1 antigen on the surface of stimulated mouse T and B lymphocytes. Int. Immunol 8:765-75 (1996).
Al-Lazikani et al. Standard conformations for the canonical structures of immunoglobulins. J. Mol Biology 273(4):927-948 (1997).
Altschul et al. Basic local alignment search tool. J Mol Biol 215(3):403-410 (1990).
Altschul, et al. Gapped BLAST and PSI-BLAST: a new generation of protein database search programs. Nucleic Acids Res 25:3389-3402 (1977).
Barrett et al. Treatment of advanced leukemia in mice with mRNA engineered T cells. Hum Gene Ther 22:1575-1586 (2011).
Batzer et al. Enhanced evolutionary PCR using oligonucleotides with inosine at the 3'-terminus. Nucleic Acids Res. 19(18):5081 (1991).
Bird et al. Single-chain antigen-binding proteins. Science 242(4877):423-426 (1988).
Blank et al. Interaction of PD-L1 on tumor cells with PD-1 on tumor-specific T cells as a mechanism of immune evasion: implications for tumor immunotherapy. Cancer Immunol Immunother 54:307-314 (2005).
Caldas et al. Design and synthesis of germline-based hemi-humanized single-chain Fv against the CD18 surface antigen. Protein Eng 13(5):353-360 (2000).
Carter et al. PD-1: PD-L inhibitory pathway affects both CD4(+) and CD8(+) T cells and is overcome by IL-2. Eur J Immunol 32:634-643 (2002).
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
Dao et al. Targeting the intracellular WT1 oncogene product with a therapeutic human antibody. Sci Transl Med 5(176):176ra33 (2013).
De Genst et al. Antibody repertoire development in camelids. Dev Comp Immunol 30(1-2):187-198 (2006).
Dong et al. B7-H1 pathway and its role in the evasion of tumor immunity. J Mol Med 81:281-287 (2003).
Elango et al. Optimized transfection of mRNA transcribed from a d(A/T)100 tail-containing vector. Biochim Biophys Res Commun 330:958-966 (2005).
Freeman et al. Engagement of the PD-1 immunoinhibitory receptor by a novel B7 family member leads to negative regulation of lymphocyte activation. J Exp Med 192:1027-1034 (2000).
Garland et al. The use of Teflon cell culture bags to expand functionally active CD8+ cytotoxic T lymphocytes. J Immunol Meth 227(1-2):53-63 (1999).
Grupp et al. Chimeric antigen receptor-modified T cells for acute lymphoid leukemia. NEJM 368:1509-1518 (2013).
Haanen et al. Selective expansion of cross-reactive CD8(+) memory T cells by viral variants. J Exp Med 190(9):1319-1328 (1999).
Hollinger et al. "Diabodies": Small bivalent and bispecific antibody fragments. PNAS USA 90:6444 6448 (1993).
Huston et al. Protein engineering of antibody binding sites: recovery of specific activity in an anti-digoxin single-chain Fv analogue produced in *Escherichia coli*. PNAS USA 85(16):5879-5883 (1988).
Izumoto et al. Phase II clinical trial of Wilms tumor 1 peptide vaccination for patients with recurrent glioblastoma multiforme. J Neurosurg 108:963-971 (2008).
Jones et al. Replacing the complementarity-determining regions in a human antibody with those from a mouse. Nature 321:522-525 (1986).
Kalos et al. T cells with chimeric antigen receptors have potent antitumor effects and can establish memory in patients with advanced leukemia. Sci Transl Med 3(95):95ra73 (2011).
Konishi et al. B7-H1 expression on non-small cell lung cancer cells and its relationship with tumor-infiltrating lymphocytes and their PD-1 expression. Clin Cancer Res 10:5094-5100 (2004).
Latchman et al. PD-L2 is a second ligand for PD-1 and inhibits T cell activation. Nat Immunol 2:261-268 (2001).
Milone et al. Chimeric receptors containing CD137 signal transduction domains mediate enhanced survival of T cells and increased antileukemic efficacy in vivo. Mol Ther 17(8):1453-1464 (2009).
Mumtaz et al. Design of liposomes for circumventing the reticuloendothelial cells. Glycobiology 5:505-10 (1991).
Nacheva et al. Preventing nondesired RNA-primed RNA extension catalyzed by T7 RNA polymerase. Eur J Biochem 270:1458-1465 (2003).
Needleman et al. A general method applicable to the search for similarities in the amino acid sequence of two proteins. J. Mol. Biol. 48:443-453 (1970).
Nicholson et al. Construction and characterisation of a functional CD19 specific single chain Fv fragment for immunotherapy of B lineage leukaemia and lymphoma. Mol Immun 34(16-17):1157-1165 (1997).
Nishikawa et al. Nonviral vectors in the new millennium: delivery barriers in gene transfer. Human Gene Therapy. 12:861-870 (2001).
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
Padlan. A possible procedure for reducing the immunogenicity of antibody variable domains while preserving their ligand-binding properties. Mol Immunol 28(4-5):489-498 (1991).
PCT/US2019/052206 International Search Report and Written Opinion dated Feb. 14, 2020.
PCT/US2019/052206 Invitation to Pay Additional Fees dated Dec. 23, 2019.
PCT/US2019/052270 Invitation to Pay Additional Fees dated Jan. 9, 2020.

(56) References Cited

OTHER PUBLICATIONS

PCT/US2019/053017 International Search Report and Written Opinion dated Jan. 31, 2020.
PCT/US2019/053017 Invitation to Pay Additional Fees dated Nov. 27, 2019.
Pearson, et al. Improved Tools for Biological Sequence Comparison. Proc. Nat'l Acad. Sci. USA. 85 (1988): 2444-48.
Pedersen et al. Comparison of surface accessible residues in human and murine immunoglobulin Fv domains. Implication for humanization of murine antibodies. J Mol Biol 235(3):959-973 (1994).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Presta. Antibody Engineering. Curr Op Struct Biol 2:593-596 (1992).
Riechmann et al. Reshaping human antibodies for therapy. Nature, 332.6162:323-7 (1988).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg et al. Use of tumor-infiltrating lymphocytes and interleukin-2 in the immunotherapy of patients with metastatic melanoma. A preliminary report. NEJM 319:1676 (1988).
Rossolini et al. Use of deoxyinosine-containing primers vs degenerate primers for polymerase chain reaction based on ambiguous sequence information. Mol Cell Probes 8(2):91-98 (1994).
Sadelain et al. The basic principles of chimeric antigen receptor design. Cancer Discov. 3(4):388-98 (2013).
Sandhu. A rapid procedure for the humanization of monoclonal antibodies. Gene 150(2):409-410 (1994).
Sastry et al. Targeting hepatitis B virus-infected cells with a T-cell receptor-like antibody. J Virol 85(5):1935-1942 (2011).
Schenborn et al. A novel transcription property of SP6 and T7 RNA polymerases: dependence on template structure. Nuc Acids Res 13:6223-6236 (1985).
Scheraga. Predicting three-dimensional structures of oligopeptides. Rev Computational Chem 3:73-142 (1992).
Sergeeva et al. An anti-PR1/HLA-A2 T-cell receptor-like antibody mediates complement-dependent cytotoxicity against acute myeloid leukemia progenitor cells. Blood 117(16):4262-4272 (2011).
Smith et al. Comparison of Biosequences. Advances in Applied Mathematics. 2:482-489 (1981).
Song et al. CD27 costimulation augments the survival and antitumor activity of redirected human T cells in vivo. Blood 119(3):696-706 (2012).
Stepinski et al. Synthesis and properties of mRNAs containing the novel 'anti-reverse' cap analogs 7-methyl(3'0-methyl)GpppG and 7-methyl(e'-deoxy)GpppG. RNA 7:1486-1495 (2001).
Studnicka et al. Human-engineered monoclonal antibodies retain full specific binding activity by preserving non-CDR complementarity-modulating residues. Pro Eng 7(6):805-814 (1994).
Tan et al. "Superhumanized" antibodies: reduction of immunogenic potential by complementarity-determining region grafting with human germline sequences: application to an anti-CD28. J Immunol 169:1119-1125 (2002).
Tassev et al. Retargeting NK92 cells using an HLA-A2-restricted, EBNA3C-specific chimeric antigen receptor. Cancer Gene Ther 19(2):84-100 (2012).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Ui-Tei et al. Sensitive assay of RNA interference in *Drosophila* and Chinese hamster cultured cells using firefly luciferase gene as target. FEBS Letters 479: 79-82 (2000).
U.S. Appl. No. 15/630,259 Office Action dated Dec. 30, 2019.

U.S. Appl. No. 16/159,545 Office Action dated Dec. 2, 2019.
Verhoeyen et al. Reshaping human antibodies: Grafting an antilysozyme activity. Science 239:1534-1536 (1988).
Verma et al. TCR mimic monoclonal antibody targets a specific peptide/HLA class I complex and significantly impedes tumor growth in vivo using breast cancer models. J Immunol 184(4):2156-2165 (2010).
Willemsen et al. A phage display selected fab fragment with MHC class I-restricted specificity for MAGE-A1 allows for retargeting of primary human T lymphocytes. Gene Ther 8(21):1601-1608 (2001).
Yan et al. Engineering upper hinge improves stability and effector function of a human IgG1. J. Biol. Chem. 287:5891 (2012).
Yoshinaga et al. Ig L-chain shuffling for affinity maturation of phage library-derived human anti-human MCP-1 antibody blocking its chemotactic activity. J Biochem 143(5):593-601 (2008).
Baum et al. Antitumor activities of PSMAxCD3 diabodies by redirected T-cell lysis of prostate cancer cells. Immunotherapy 5(1):27-38 (2013).
Harmsen et al. Properties, production, and applications of camelid single-domain antibody fragments. Appl. Microbiol. Biotechnol. 77:13-22 (2007).
PCT/US2019/052270 International Search Report and Written Opinion dated Mar. 5, 2020.
U.S. Appl. No. 15/821,498 Office Action dated Apr. 21, 2020.
U.S. Appl. No. 15/821,530 Office Action dated Apr. 22, 2020.
U.S. Appl. No. 16/583,070 Office Action dated Mar. 3, 2020.
Zabetakis et al. Contributions of the complementarity determining regions to the thermal stability of a single-domain antibody. PLoS One 8(10):e77678 (2013).
Bendell et al. Abstract 5552: First-in-human phase I study of HPN424, a tri-specific half-life extended PSMA-targeting T-cell engager in patients with metastatic castration-resistant prostate cancer (mCRPC). J Clin Oncol 38(15):5552 (May 2020).
PCT/US/2020/032985 International Search Report and Written Opinion dated Oct. 15, 2020.
U.S. Appl. No. 15/630,259 Office Action dated Sep. 30, 2020.
U.S. Appl. No. 16/159,554 Office Action dated Oct. 5, 2020.
Almagro et al. Humanization of antibodies. Front Biosci 13:1619-1633 (2008).
Argani et al. Mesothelin is overexpressed in the vast majority of ductal adenocarcinomas of the pancreas: identification of a new pancreatic cancer marker by serial analysis of gene expression (SAGE). Clin Cancer Res 7(12):3862-3868 (2001).
Austin et al. Cancer Research (Jul. 2018) vol. 78, No. 13, Supp. Supplement 1. Abstract No. 1781. Meeting Info: 2018 Annual Meeting of the American Association for Cancer Research, AACR 2018. Chicago, IL, United States. Apr. 14, 2018-Apr. 18, 2018).
Baca et al. Antibody humanization using monovalent phage display. J Biol Chem 272(16):10678-10684 (1997).
Baeuerle et al. Bispecific T-cell engaging antibodies for cancer therapy. Cancer Res 69:4941-4944 (2009).
Bedouelle et al. Diversity and junction residues as hotspots of binding energy in an antibody neutralizing the dengue virus. FEBS J 273(1):34-46 (2006).
Bortoletto et al. Optimizing anti-CD3 affinity for effective T cell targeting against tumor cells. Eur J Immunol 32:3102-3107 (2002).
Bracci et al. Cyclophosphamide enhances the antitumor efficacy of adoptively transferred immune cells through the induction of cytokine expression, B-cell and T-cell homeostatic proliferation, and specific tumor infiltration. Clin Cancer Res 13(2 Pt 1):644-653 (2007).
Brown et al. Tolerance of single, but not multiple, amino acid replacements in antibody VH CDR 2: a means of minimizing B cell wastage from somatic hypermutation? J Immunol 156(9):3285-3291 (1996).
Caldas et al. Humanization of the anti-CD18 antibody 6.7: an unexpected effect of a framework residue in binding to antigen. Mol Immunol. 39(15):941-952 (2003).
Carter et al. Humanization of an anti-p185HER2 antibody for human cancer therapy. PNAS USA 89(10):4285-4289 (1992).
Casset et al. A peptide mimetic of an anti-CD4 monoclonal antibody by rational design. Biochemical and Biophysical Research Communication 307:198-205 (2003).

(56) References Cited

OTHER PUBLICATIONS

Chang et al. Loop-sequence features and stability determinants in antibody variable domains by high-throughput experiments. Structure 22(1):9-21 (2014).
Chang et al. Molecular cloning of mesothelin, a differentiation antigen present on mesothelium, mesotheliomas, and ovarian cancers. PNAS USA 93:136-140 (1996).
Chatalic et al. A Novel 111 In-labeled Anti-PSMA Nanobody for Targeted SPECT/CT Imaging of Prostate Cancer. J Nucl Med 56(7):1094-1099 and Supplemental Data (2015).
Chen et al. Selection and analysis of an optimized anti-VEGF antibody: Crystal structure of an affinity-matured Fab in complex with antigen. J Mol Bio 293:865-881 (1999).
Chen, Xiaoying et al. Fusion protein linkers: Property, design and functionality. Advanced Drug Delivery Reviews 65:1357-1369 (2013).
Chien et al. Significant structural and functional change of an antigen-binding site by a distant amino acid substitution: proposal of a structural mechanism. PNAS USA 86(14):5532-5536 (1989).
Cho et al. Targeting B Cell Maturation Antigen (BCMA) in Multiple Myeloma: Potential Uses of BCMA-Based Immunotherapy. Front Immunol 9:1821 (2018).
Choi et al. Engineering of Immunoglobulin Fc heterodimers using yeast surface-displayed combinatorial Fc library screening. PLOS One 10(12):e0145349 (2015).
Chothia et al. Canonical structures for the hypervariable regions of immunoglobulins. J Mol Biol 196(4):901-917 (1987).
Chothia, et al. Conformations of immunoglobulin hypervariable regions. Nature. Dec. 21-28, 1989;342(6252):877-83.
Corso et al. Real-time detection of mesothelin in pancreatic cancer cell line supernatant using an acoustic wave immunosensor. Cancer Detect Prev 30:180-187 (2006).
Creaney et al. Detection of malignant mesothelioma in asbestos-exposed individuals: the potential role of soluble mesothelin-related protein. Hematol. Oncol. Clin. North Am. 19:1025-1040 (2005).
Cristaudo et al. Clinical significance of serum mesothelin in patients with mesothelioma and lung cancer. Clin. Cancer Res. 13:5076-5081 (2007).
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Dennis et al. Imaging Tumors with an Albumin-Binding Fab, a Novel Tumor-Targeting Agent. Cancer Res 67(1):254-61 (2007).
Document D28—Investigation of human CD3ε variants binding to monoclonal antibodies. Submitted by Pfizer to the European Patent Register on Apr. 30, 2014 in connection with their opposition to the EP2155783 patent. (3 pages) (2014).
Document D78—CD3ε N-terminal peptide bound to the CDRs of SP24. Submitted by Janssen Biotech to the European Patent Register on Mar. 18, 2016 in connection with their opposition to the EP2155783 patent (1 page) (2016).
Document D79—Interactions between CD3ε and SP34 CDR residues. CD3ε residues are in ellipses, SP34 CDR residues are in boxes. Submitted by Janssen Biotech to the European Patent Register on Mar. 18, 2016 in connection with their opposition to the EP2155783 patent (1 page) (2016).
Document D83—Alignment of variable domains from the prior art and the patent. Submitted by Janssen Biotech to the European Patent Register on Mar. 18, 2016 in connection with their opposition to the EP2155783 patent (1 page) (2016).
Foote et al. Antibody Framework Residues Affecting the Conformation of the Hypervariable Loops. J. Mol. Biol. 224(2):487-99 (1992).
Frankel et al. Targeting T cells to tumor cells using bispecific antibodies. Curr Opin Chem Biol 17(3):385-392 (2013).
Giusti et al. Somatic diversification of S107 from an antiphosphocholine to an anti-DNA autoantibody is due to a single base change in its heavy chain variable region. PNAS USA 84(9):2926-30 (1987).
Goldman et al. Enhancing Stability of Camelid and Shark Single Domain Antibodies: An Overview. Front. Immunol. 8:865 (2017).
Goodman et al. The Pharmaceutical Basis of Therapeutics. 6th ed. pp. 21-25 (1980).
Goswami et al. Developments and Challenges for mAb-Based Therapeutics. Antibodies 2:452-500 (2013).
Gross et al. Endowing T cells with antibody specificity using chimeric T cell receptors. FASEB J. 6(15):3370-3378 (1992).
Gubbels et al. Mesothelin-MUC16 binding is a high affinity, N-glycan dependent interaction that facilitates peritoneal metastasis of ovarian tumors. Mol Cancer 5:50 (2006).
Gussow et al. Chapter 5: Humanization of Monoclonal Antibodies. Methods in Enzymology 203:99-121 (1991).
Harding et al. The immunogenicity of humanized and fully human antibodies: residual immunogenicity resides in the CDR regions. MAbs 2(3):256-265 (2010).
Hassan et al. Detection and quantitation of serum mesothelin, a tumor marker for patients with mesothelioma and ovarian cancer. Clin Cancer Res 12:447-453 (2006).
Hassan et al. Mesothelin targeted cancer immunotherapy. Eur J Cancer 44:46-53 (2008).
Hassan et al. Mesothelin: a new target for immunotherapy. Clin Cancer Res 10:3937-3942 (2004).
Hassan et al. Phase I study of SS1P, a recombinant anti-mesothelin immunotoxin given as a bolus I.V. infusion to patients with mesothelin-expressing mesothelioma, ovarian, and pancreatic cancers. Clin Cancer Res 13(17):5144-5149 (2007).
Hassan et al. Preclinical evaluation of MORAb-009, a chimeric antibody targeting tumor-associated mesothelin. Cancer Immun. 7:20 (2007).
Hellstrom et al. Mesothelin variant 1 is released from tumor cells as a diagnostic marker. Cancer Epidemiol Biomarkers Prev 15:1014-1020 (2006).
Hipp et al. A novel BCMA/CD3 bispecific T-cell engager for the treatment of multiple myeloma induces selective lysis in vitro and in vivo. Leukemia 31(8):1743-1751 (2017).
Ho et al. A novel high-affinity human monoclonal antibody to mesothelin. Int J Cancer 128:2020-2030 (2011).
Ho et al. Mesothelin expression in human lung cancer. Clin Cancer Res 13:1571-1575 (2007).
Ho et al. Mesothelin is shed from tumor cells. Cancer Epidemiol Biomarkers Prev 15:1751 (2006).
Holm et al. Functional mapping and single chain construction of the anti-cytokeratin 8 monoclonal antibody TS1. Mol Immunol 44(6):1075-1084 (2007).
Holt et al. Anti-serum albumin domain antibodies for extending the half-lives of short lived drugs. Protien Eng Des Sel 21(5):283-288 (2008).
Hopp et al. The effects of affinity and valency of an albumin-binding domain (ABD) on the half-life of a single-chain diabody-ABD fusion protein. Protein Eng. Des. Sel. 23(11):827-34 (2010).
Hutchinson et al. Mutagenesis at a specific position in a DNA sequence. J Biol Chem 253:6551-6560 (1978).
Janssen letter—Submission under Rule 116 EPC. Submitted by Janssen Biotech to the European Patent Register on Mar. 18, 2016 in connection with their opposition to the EP2155783 patent (6 pages) (2016).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).
Kabat et al. Sequences of proteins of immunological interest. NIH Publ. No. 91-3242 1:647-669 (1991).
Kojima et al. Molecular cloning and expression of megakaryocyte potentiating factor cDNA. J Biol Chem 270:21984-21990 (1995).
Laabi et al. The BCMA gene, preferentially expressed during B lymphoid maturation, is bidirectionally transcribed. Nucleic Acids Res 22(7):1147-1154 (1994).
Le Gall et al. Immunosuppressive properties of anti-CD3 single-chain Fv and diabody. J Immunol Methods 285(1):111-127 (2004).
Li et al. Development of novel tetravalent anti-CD20 antibodies with potent antitumor activity. Cancer Res 68:2400-2408 (2008).

(56) References Cited

OTHER PUBLICATIONS

Liu et al. A New Format of Single Chain Tri-specific Antibody with Diminished Molecular Size Efficiently Induces Ovarian Tumor Cell Killing. Biotechnology Letters 27(22):1821-1827 (2005).
Liu et al. MGD011, a CD19 × CD3 Dual Affinity Re-Targeting Bi-specific Molecule Incorporating Extended Circulating Half-life for the Treatment of B-cell Malignancies. Clin Cancer Res 23(6):1506-1518 (epub 2016) (2017).
Lowman et al. Monovalent phage display: A method for selecting variant proteins from random libraries. Methods 3:205-216 (1991).
Lu et al. In vitro and in vivo antitumor effect of a trivalent bispecific antibody targeting ErbB2 and CD16. Cancer Biol Ther. 7(11):1744-1750 (2008).
Lutterbuese et al. T cell-engaging BiTE antibodies specific for EGFR potently eliminate KRAS- and BRAF-mutated colorectal cancer cells. PNAS 107:12605-12610 (2007).
Maccallum et al. Antibody-antigen interactions: contact analysis and binding site topography. J Mol Biol. 262(5):732-745 (1996).
Mariuzza et al. The structural basis of antigen-antibody recognition. Annu Rev Biophys Biophys Chem 16:139-159 (1987).
Mirsky et al. Antibody-Specific Model of Amino Acid Substitution for Immunological Inferences from Alignments of Antibody Sequences. Mol. Biol. Evol. 32(3):806-819 (2014).
Morea et al. Antibody modeling: implications for engineering and design. Methods 20(3):267-279 (2000).
Moschella et al. Unraveling cancer chemoimmunotherapy mechanisms by gene and protein expression profiling of responses to cyclophosphamide. Cancer Res 71(10):3528-3539 (2011).
Mueller et al. Improved pharmacokinetics of recombinant bispecific antibody molecules by fusion to human serum albumin. J Bio Chem 282(17):12650-12660 (2007).
Müller et al. Improved Pharmacokinetics of Recombinant Bispecific Antibody Molecules by Fusion to Human Serum Albumin. J. Biol. Chem. 282(17):12650-60 (2007).
Muller et al. Improving the pharmacokinetic properties of biologics by fusion to an anti-HSA shark VNAR domain. MAbs 4(6):673-685 (2012).
Muul et al. Persistence and expression of the adenosine deaminase gene for 12 years and immune reaction to gene transfer components: long-term results of the first clinical gene therapy trial. Blood 101(7):2563-2569 (2003).
Muyldermans. Nanobodies: natural single-domain antibodies. Annu Rev Biochem 82:775-797 (2013).
Nazarian et al. Characterization of bispecific T-cell Engager (BiTE) antibodies with a high-capacity T-cell dependent cellular cytotoxicity (TDCC) assay. J Biomol Screen 20:519-527 (2015).
Nelson et al. Antibody fragments Hope and Hype. mAbs 2(1):77-83 (2010).
Nunez-Prado et al. The coming of age of engineered multivalent antibodies. Drug Discovery Today 20(5):588-594 (2015).
Ohiro et al. A homogeneous and noncompetitive immunoassay based on the enhanced fluorescence resonance energy transfer by leucine zipper interaction. Anal Chem 74(22):5786-5792 (2002).
O'Keefe et al. Chapter 18: Prostate specific membrane antigen. In: Chung L.W.K., Isaacs W.B., Simons J.W. (eds) Prostate Cancer. Contemporary Cancer Research. Humana Press, Totowa, NJ (pp. 307-326) (2001).
Ordonez. Application of mesothelin immunostaining in tumor diagnosis. Am J Surg Pathol 27:1418-1428 (2003).
Padlan et al. Structure of an antibody-antigen complex: Crystal structure of the HyHEL-10 Fab-lysozyme complex. PNAS USA 86:5938-5942 (1989).
Padlan. Anatomy Of The Antibody Molecule. Mol Immunol 31(3):169-217 (1994).
Pawluczkowycz et al. Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by RTX. J Immunol 183:749-758 (2009).

PCT/US2016/033644 International Preliminary Report on Patentability dated Nov. 30, 2017.
PCT/US2016/033644 International Search Report and Written Opinion dated Sep. 6, 2016.
PCT/US2017/033665 International Search Report and Written Opinion dated Oct. 18, 2017.
PCT/US2017/033673 International Search Report and Written Opinion dated Oct. 18, 2017.
PCT/US2017/056530 International Preliminary Report on Patentability dated Apr. 25, 2019.
PCT/US2017/063121 International Search Report and Written Opinion dated Mar. 26, 2018.
PCT/US2017/063121 Invitation to Pay Additional Fees dated Feb. 1, 2018.
PCT/US2017/063126 International Search Report and Written Opinion dated Apr. 5, 2018.
PCT/US2017/063126 Invitation to Pay Additional Fees dated Feb. 1, 2018.
PCT/US2017056530 International Search Report and Written Opinion dated Jan. 23, 2018.
PCT/US2018/014396 International Preliminary Report on Patentability dated Aug. 1, 2019.
PCT/US2018/014396 International Search Report and Written Opinion dated Jun. 14, 2018.
PCT/US2018/020185 International Search Report and Written Opinion dated Jun. 15, 2018.
PCT/US2018/020307 International Search Report and Written Opinion dated Aug. 24, 2018.
PCT/US2018/030983 International Search Report and Written Opinion dated Sep. 25, 2018.
PCT/US2018/030983 Invitation to Pay Additional Fees dated Jul. 31, 2018.
PCT/US2018/032418 International Search Report and Written Opinion dated Sep. 24, 2018.
PCT/US2018/032427 International Search Report and Written Opinion dated Sep. 13, 2018.
PCT/US2018/055659 International Search Report and Written Opinion dated Feb. 21, 2019.
PCT/US2018/055659 Invitation to Pay Additional Fees dated Dec. 19, 2018.
PCT/US2018/055682 International Search Report and Written Opinion dated Mar. 1, 2019.
PCT/US2018/055682 Invitation to Pay Additional Fees dated Jan. 8, 2019.
PCT/US2018/32418 Invitation to Pay Additional Fees dated Jul. 23, 2018.
PCT/US2018/32427 Invitation to Pay Additional Fees dated Jul. 24, 2018.
PCT/US2019/032224 International Search Report and Written Opinion dated Aug. 28, 2019.
PCT/US2019/032302 International Search Report and Written Opinion dated Aug. 22, 2019.
PCT/US2019/032306 International Search Report and Written Opinion dated Aug. 22, 2019.
PCT/US2019/032307 International Search Report and Written Opinion dated Aug. 22, 2019.
Pfizer letter—Opposition to European Patent EP2155783 (Application 08735001.3). Submitted by Pfizer to the European Patent Register on Apr. 30, 2014 in connection with their opposition to the EP2155783 patent. (pp. 1-23 and Appendix 1 on pp. 24-26) (2014).
Presta et al. Humanization of an antibody directed against IgE. J Immunol 151:2623-2632 (1993).
Ramadoss et al. An Anti-B Cell Maturation Antigen bispecific Antibody for Multiple Myeloma. J. Ann. Chem. Soc. 137(16):5288-91 (2015).
Riechmann et al. Single domain antibodies: comparison of camel VH and camelised human VH domains. J Immunol Methods 231(1-2):25-38 (1999).
Rosok et al. A Combinatorial Library Strategy for the Rapid Humanization of Anticarcinoma BR96 Fab. J Biol Chem 271:22611-22618 (1996).

(56) References Cited

OTHER PUBLICATIONS

Rozan et al. Single-domain antibody-based and linker-free bispecific antibodies targeting FcγRIII induce potent antitumor activity without recruiting regulatory T cells. Mol Cancer Ther 12(8):1481-1491 (2013).
Rudikoff et al. Single amino acid substitution altering antigen-binding Specificity. PNAS USA 79:1979-1983 (1982).
Rump et al. Binding of ovarian cancer antigen CA125/MUC16 to mesothelin mediates cell adhesion. J Biol Chem 279:9190-9198 (2004).
Running Deer et al. High-level expression of proteins in mammalian cells using transcription regulatory sequences from the Chinese hamster EF-1alpha gene. Biotechnol Prog. 20:880-889 (2004).
Sadelain et al. Targeting tumours with genetically enhanced T lymphocytes. Nat Rev Cancer 3(1):35-45 (2003).
Saerens et al. Identification of a universal VHH framework to graft non-canonical antigen-binding loops of camel single-domain antibodies. J. Mol. Biol. 352(3):597-607 (2005).
Schmidt et al. Cloning and Characterization of Canine Prostate-Specific Membrane Antigen. The Prostate 73:642-650 (2013).
Schmittgen et al. Expression of prostate specific membrane antigen and three alternatively spliced variants of PSMA in prostate cancer patients. Int J Cancer 107:323-329 (2003).
Sims et al. A humanized CD18 antibody can block function without cell destruction. J Immunol., 151 (1993): 2296-2308.
Smirnova et al. Identification of new splice variants of the genes BAFF and BCMA. Mol. Immunol. 45 (4):1179-83 (2008).
Spiess et al. Alternative molecular formats and therapeutic applications for bispecific antibodies. Mol. Immunol. 67(2 Pt A):95-106 (2015).
Sternjak et al. Cancer Research, (Jul. 2017) vol. 77, No. 13, Supp. Supplement 1. Abstract No. 3630. Meeting Info: American Association for Cancer Research Annual Meeting 2017. Washington, DC, United States. Apr. 1, 2017-Apr. 5, 2017.
Stork et al. A novel tri-functional antibody fusion protein with improved pharmacokinetic properties generated by fusing a bispecific single-chain diabody with an albumin-binding domain from streptococcal protein G. Protein Eng. Des. Sel. 20(11):569-76 (2007).
Strop. Veracity of microbial transglutaminase. Bioconjugate Chem. 25(5):855-862 (2014).
Su et al. PSMA specific single chain antibody-mediated targeted knockdown of Notch1 inhibits human prostate cancer cell proliferation and tumor growth. Cancer Lett. 338 (2): 282-291 (2013).
Tang et al. A human single-domain antibody elicits potent antitumor activity by targeting an epitope in mesothelin close to the cancer cell surface. Mol. Cancer Thera 12(4):416-426 (2013).
Thomas et al. Mesothelin-specific CD8(+) T cell responses provide evidence of in vivo cross-priming by antigen-presenting cells in vaccinated pancreatic cancer patients. J Exp Med 200:297-306 (2004).
Tijink et al. Improved tumor targeting of anti-epidermal growth factor receptor nanobodies through albumin binding: taking advantage of modular Nanobody technology. Mol. Cancer Ther. 7(8):2288-97 (2008).
Tiller et al. Facile Affinity Maturation of Antibody Variable Domains Using Natural Diversity Mutagenesis. Front. Immunol. 8:986 (2017).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
U.S. Appl. No. 15/160,984 Office Action dated Feb. 24, 2017.
U.S. Appl. No. 15/160,984 Office Action dated Sep. 22, 2016.
U.S. Appl. No. 15/600,264 Office Action dated Apr. 25, 2019.
U.S. Appl. No. 15/600,264 Office Action dated Apr. 26, 2018.
U.S. Appl. No. 15/600,264 Office Action dated Nov. 27, 2018.
U.S. Appl. No. 15/600,264 Office Action dated Oct. 3, 2017.
U.S. Appl. No. 15/600,582 Office Action dated Nov. 16, 2017.
U.S. Appl. No. 15/704,620 Office Action dated Oct. 26, 2017.
U.S. Appl. No. 15/821,498 Office Action dated May 3, 2019.
U.S. Appl. No. 15/821,498 Office Action dated Oct. 26, 2018.
U.S. Appl. No. 15/821,530 Office Action dated Apr. 3, 2019.
U.S. Appl. No. 15/821,530 Office Action dated Sep. 25, 2018.
U.S. Appl. No. 15/977,968 Office Action dated Feb. 21, 2019.
U.S. Appl. No. 15/977,988 Office Action dated Aug. 20, 2019.
U.S. Appl. No. 15/977,988 Office Action dated Mar. 26, 2019.
U.S. Appl. No. 15/977,988 Preinterview First Office Action dated Jan. 25, 2019.
U.S. Appl. No. 16/159,545 Office Action dated Aug. 6, 2019.
U.S. Appl. No. 16/159,554 Office Action dated Jun. 7, 2019.
U.S. Appl. No. 16/159,554 Office Action dated Oct. 1, 2019.
Vajdos et al. Comprehensive functional maps of the antigen-binding site of an anti-ErbB2 antibody obtained with shotgun scanning mutagenesis. J Mol Biol 320:415-428 (2002).
Van Den Beuchken et al. Building novel binding ligands to B7.1 and B7.2 based on human antibody single variable light chain domains. J Mol biol 310:591-601 (2001).
Van Der Linden et al. Induction of immune responses and molecular cloning of the heavy chain antibody repertoire of Lama glama. J Immunol Methods 240:185-195 (2000).
Vaughan et al. Human antibodies by design. Nature Biotech 16:535-539 (1998).
Vincke et al. General strategy to humanize a camelid single-domain antibody and identification of a universal humanized nanobody scaffold. J. Biol. Chem. 284(5):3273-3284 (2009).
Wang et al. A New Recombinant Single Chain Trispecific Antibody Recruits T Lymphocytes to Kill CEA (Carcinoma Embryonic Antigen) Positive Tumor Cells In Vitro Efficiently. Journal Of Biochemistry 135(4):555-565 (2004).
Winkler et al. Changing the antigen binding specificity by single point mutations of an anti-p24 (HIV-1) antibody. J Immunol. 165(8):4505-4514 (2000).
Wu et al. Humanization of a murine monoclonal antibody by simultaneous optimization of framework and CDR residues. J.Mol. Biol. 294:151-162 (1999).
Yee et al. Adoptive T cell therapy using antigen-specific CD8+ T cell clones for the treatment of patients with metastatic melanoma: in vivo persistence, migration, and antitumor effect of transferred T cells. PNAS USA 99(25):16168-16173 (2002).
Yu et al. Rationalization and design of the complementarity determining region sequences in an antibody-antigen recognition interface. PLoS One 7(3):e33340 (2012).
Zare et al. Production of nanobodies against prostate-specific membrane antigen (PSMA) recognizing LnCaP cells. Int. J. Biol. Markers 29(2):e169-e179 (2014).
Zhu et al. COMBODY: one-domain antibody multimer with improved avidity. Immunology And Cell Biology 88(6):667-675 (2010).
Zhang et al. New High Affinity Monoclonal Antibodies Recognize Non-Overlapping Epitopes On Mesothelin For Monitoring And Treating Mesothelioma. Sci Rep 5:9928 (2015).
Balzar et al. The biology of the 17-1A antigen (Ep-CAM). J. Mol. Med. 77:699-712 (1999).
Bluemel et al. Epitope distance to the target cell membrane and antigen size determine the potency of T cell-mediated lysis by BiTE antibodies specific for a large melanoma surface antigen. Cancer Immunol Immunother 59(8):1197-209 (2010).
Chaubal et al. Ep-CAM—a marker for the detection of disseminated tumor cells in patients suffering from SCCHN. Anticancer Res 19:2237-2242 (1999).
Davé et al. Fab-dsFv: A bispecific antibody format with extended serum half-life through albumin binding. MAbs 8(7):1319-1335 (2016).
Dickopf et al. Format and geometries matter: Structure-based design defines the functionality of bispecific antibodies. Comput Struct Biotechnol J 18:1221-1227 (2020).
Eyvazi et al. Antibody Based EpCAM Targeted Therapy of Cancer, Review and Update. Curr Cancer Drug Targets. 18(9):857-868 (2018).
Gastl et al. Ep-CAM overexpression in breast cancer as a predictor of survival. Lancet. 356:1981-1982 (2000).
Goettlinger et al. The epithelial cell surface antigen 17-1A, a target for antibody-mediated tumor therapy: its biochemical nature, tissue distribution and recognition by different monoclonal antibodies. Int J Cancer. 38:47-53 (1986).

(56) References Cited

OTHER PUBLICATIONS

Kim et al. Strategies and Advancement in Antibody-Drug Conjugate Optimization for Targeted Cancer Therapeutics. Biomol Ther (Seoul) 23(6):493-509 (2015).

Koprowski et al. Colorectal carcinoma antigens detected by hybridoma antibodies. Somatic Cell Genet. 5:957-971 (1979).

Lehmann et al. Stability engineering of anti-EGFR scFv antibodies by rational design of a lambda-to-kappa swap of the VL framework using a structure-guided approach. MAbs 7(6):1058-1071 (2015).

Lin et al. Improved affinity of a chicken single-chain antibody to avian infectious bronchitis virus by site-directed mutagenesis of complementarity-determining region H3. African Journal of Biotechnology 10(79):18294-18302 (2011).

Litvinov et al. Epithelial cell adhesion molecule (Ep-CAM) modulates cell-cell interactions mediated by classic cadherins. J Cell Biol. 139:1337-1348 (1997).

Litvinov et al. Expression of Ep-CAM in cervical squamous epithelia correlates with an increased proliferation and the disappearance of markers for terminal differentiation. Am. J. Pathol. 148:865-75 (1996).

Lucchi et al. The Masking Game: Design of Activatable Antibodies and Mimetics for Selective Thera-peutics Cell Control. ACS Cent Sci 7(5):724-738 (2021).

Mccall et al. Isolation and characterization of an anti-CD16 single-chain Fv fragment and construction of an anti-HER2/neu/anti-CD16 bispecific scFv that triggers CD16-dependent tumor cytolysis Mol Immunol. 36(7):433-46 (1999).

Mccarthy et al. Altering the fine specificity of an anti-Legionella single chain antibody by a single amino acid insertion. J Immunol Methods 251(1-2):137-49 (2001).

Osta et al. EpCAM is overexpressed in breast cancer and is a potential target for breast cancer gene therapy. Cancer Res 64:5818-24 (2004).

PCT/US2021/058108 International Search Report and Written Opinion dated Apr. 1, 2022.

Piyathilake et al. The expression of Ep-CAM (17-1A) in squamous cell cancers of the lung. Hum Pathol. 31:482-487 (2000).

Quak et al. Production of a monoclonal antibody (K 931) to a squamous cell carcinoma associated antigen identified as the 17-1A antigen. Hybridoma 9:377-387 (1990).

Roda-Navarro et al. Understanding the Spatial Topology of Artificial Immunological Synapses Assembled in T Cell-Redirecting Strategies: A Major Issue in Cancer Immunotherapy. Front Cell Dev Biol 7:370 (2020).

Simon et al. Epithelial glycoprotein is a member of a family of epithelial cell surface antigens homologous to nidogen, a matrix adhesion protein. PNAS USA 87:2755-2759 (1990).

Trail et al. Antibody drug conjugates for treatment of breast cancer: Novel targets and diverse approaches in ADC design. Pharmacol Ther 181:126-142 (2018).

Trebak et al. Oligomeric state of the colon carcinoma-associated glycoprotein GA733-2 (Ep-CAM/EGP40) and its role in GA733-mediated homotypic cell-cell adhesion. J Biol Chem. 276:2299-2309 (2001).

U.S. Appl. No. 16/339,263 Office Action dated Jan. 11, 2022.
U.S. Appl. No. 16/339,263 Office Action dated May 3, 2022.
U.S. Appl. No. 16/773,843 Office Action dated Feb. 8, 2022.

* cited by examiner

```
                            SEQUENCE LISTING

<160> NUMBER OF SEQ ID NOS: 67

<210> SEQ ID NO 1
<211> LENGTH: 8
<212> TYPE: PRT
<213> ORGANISM: Unknown
<220> FEATURE:
<223> OTHER INFORMATION: Description of Unknown:
      MMP7 cleavage domain sequence

<400> SEQUENCE: 1

Lys Arg Ala Leu Gly Leu Pro Gly
1               5

<210> SEQ ID NO 2
<211> LENGTH: 40
<212> TYPE: PRT
<213> ORGANISM: Unknown
<220> FEATURE:
<223> OTHER INFORMATION: Description of Unknown:
      MMP7 cleavage domain sequence

<400> SEQUENCE: 2

Asp Glu Asp Glu Asp Glu Asp Glu Asp Glu Asp Glu Asp Glu Asp Glu
1               5                   10                  15

Arg Pro Leu Ala Leu Trp Arg Ser Asp Arg Asp Arg Asp Arg Asp Arg
            20                  25                  30

Asp Arg Asp Arg Asp Arg Asp Arg
        35                  40

<210> SEQ ID NO 3
<211> LENGTH: 5
```

```
<212> TYPE: PRT
<213> ORGANISM: Unknown
<220> FEATURE:
<223> OTHER INFORMATION: Description of Unknown:
      MMP9 cleavage domain sequence
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Leu or Ile
<220> FEATURE:
<221> NAME/KEY: MOD_RES
<222> LOCATION: (5)..(5)
<223> OTHER INFORMATION: Ser or Thr

<400> SEQUENCE: 3

Pro Arg Xaa Xaa Xaa
1               5

<210> SEQ ID NO 4
<211> LENGTH: 5
<212> TYPE: PRT
<213> ORGANISM: Unknown
<220> FEATURE:
<223> OTHER INFORMATION: Description of Unknown:
      MMP9 cleavage domain sequence

<400> SEQUENCE: 4

Leu Glu Ala Thr Ala
1               5

<210> SEQ ID NO 5
<211> LENGTH: 10
<212> TYPE: PRT
<213> ORGANISM: Unknown
<220> FEATURE:
<223> OTHER INFORMATION: Description of Unknown:
      MMP11 cleavage domain sequence

<400> SEQUENCE: 5

Gly Gly Ala Ala Asn Leu Val Arg Gly Gly
1               5                   10

<210> SEQ ID NO 6
<211> LENGTH: 10
<212> TYPE: PRT
<213> ORGANISM: Unknown
<220> FEATURE:
<223> OTHER INFORMATION: Description of Unknown:
      MMP14 cleavage domain sequence

<400> SEQUENCE: 6

Ser Gly Arg Ile Gly Phe Leu Arg Thr Ala
1               5                   10

<210> SEQ ID NO 7
<211> LENGTH: 6
<212> TYPE: PRT
<213> ORGANISM: Unknown
<220> FEATURE:
<223> OTHER INFORMATION: Description of Unknown:
      MMP cleavage domain sequence

<400> SEQUENCE: 7

Pro Leu Gly Leu Ala Gly
1               5
```

```
<210> SEQ ID NO 8
<211> LENGTH: 6
<212> TYPE: PRT
<213> ORGANISM: Unknown
<220> FEATURE:
<223> OTHER INFORMATION: Description of Unknown:
      MMP cleavage domain sequence
<220> FEATURE:
<221> NAME/KEY: MOD_RES
<222> LOCATION: (6)..(6)
<223> OTHER INFORMATION: Any amino acid

<400> SEQUENCE: 8

Pro Leu Gly Leu Ala Xaa
1               5

<210> SEQ ID NO 9
<211> LENGTH: 6
<212> TYPE: PRT
<213> ORGANISM: Unknown
<220> FEATURE:
<223> OTHER INFORMATION: Description of Unknown:
      MMP cleavage domain sequence

<400> SEQUENCE: 9

Pro Leu Gly Cys Ala Gly
1               5

<210> SEQ ID NO 10
<211> LENGTH: 8
<212> TYPE: PRT
<213> ORGANISM: Unknown
<220> FEATURE:
<223> OTHER INFORMATION: Description of Unknown:
      MMP cleavage domain sequence

<400> SEQUENCE: 10

Glu Ser Pro Ala Tyr Tyr Thr Ala
1               5

<210> SEQ ID NO 11
<211> LENGTH: 6
<212> TYPE: PRT
<213> ORGANISM: Unknown
<220> FEATURE:
<223> OTHER INFORMATION: Description of Unknown:
      MMP cleavage domain sequence

<400> SEQUENCE: 11

Arg Leu Gln Leu Lys Leu
1               5

<210> SEQ ID NO 12
<211> LENGTH: 7
<212> TYPE: PRT
<213> ORGANISM: Unknown
<220> FEATURE:
<223> OTHER INFORMATION: Description of Unknown:
      MMP cleavage domain sequence

<400> SEQUENCE: 12

Arg Leu Gln Leu Lys Ala Cys
1               5

<210> SEQ ID NO 13
<211> LENGTH: 7
<212> TYPE: PRT
<213> ORGANISM: Unknown
```

```
<220> FEATURE:
<223> OTHER INFORMATION: Description of Unknown:
      MMP2, MMP9, MMP14 cleavage domain sequence
<220> FEATURE:
<221> NAME/KEY: MOD_RES
<222> LOCATION: (3)..(3)
<223> OTHER INFORMATION: Citrulline
<220> FEATURE:
<221> NAME/KEY: MOD_RES
<222> LOCATION: (5)..(5)
<223> OTHER INFORMATION: Homophenylalanine

<400> SEQUENCE: 13

Glu Pro Xaa Gly Xaa Tyr Leu
1               5

<210> SEQ ID NO 14
<211> LENGTH: 5
<212> TYPE: PRT
<213> ORGANISM: Unknown
<220> FEATURE:
<223> OTHER INFORMATION: Description of Unknown:
      Urokinase plasminogen activator (uPA) cleavage domain sequence

<400> SEQUENCE: 14

Ser Gly Arg Ser Ala
1               5

<210> SEQ ID NO 15
<211> LENGTH: 4
<212> TYPE: PRT
<213> ORGANISM: Unknown
<220> FEATURE:
<223> OTHER INFORMATION: Description of Unknown:
      Urokinase plasminogen activator (uPA) cleavage domain sequence

<400> SEQUENCE: 15

Asp Ala Phe Lys
1

<210> SEQ ID NO 16
<211> LENGTH: 5
<212> TYPE: PRT
<213> ORGANISM: Unknown
<220> FEATURE:
<223> OTHER INFORMATION: Description of Unknown:
      Urokinase plasminogen activator (uPA) cleavage domain sequence

<400> SEQUENCE: 16

Gly Gly Gly Arg Arg
1               5

<210> SEQ ID NO 17
<211> LENGTH: 4
<212> TYPE: PRT
<213> ORGANISM: Unknown
<220> FEATURE:
<223> OTHER INFORMATION: Description of Unknown:
      Lysosomal Enzyme cleavage domain sequence

<400> SEQUENCE: 17

Gly Phe Leu Gly
1

<210> SEQ ID NO 18
<211> LENGTH: 4
<212> TYPE: PRT
<213> ORGANISM: Unknown
<220> FEATURE:
```

```
<223> OTHER INFORMATION: Description of Unknown:
      Lysosomal Enzyme cleavage domain sequence

<400> SEQUENCE: 18

Ala Leu Ala Leu
1

<210> SEQ ID NO 19
<211> LENGTH: 2
<212> TYPE: PRT
<213> ORGANISM: Unknown
<220> FEATURE:
<223> OTHER INFORMATION: Description of Unknown:
      Lysosomal Enzyme cleavage domain sequence

<400> SEQUENCE: 19

Phe Lys
1

<210> SEQ ID NO 20
<211> LENGTH: 3
<212> TYPE: PRT
<213> ORGANISM: Unknown
<220> FEATURE:
<223> OTHER INFORMATION: Description of Unknown:
      Cathepsin B cleavage domain sequence

<400> SEQUENCE: 20

Asn Leu Leu
1

<210> SEQ ID NO 21
<211> LENGTH: 5
<212> TYPE: PRT
<213> ORGANISM: Unknown
<220> FEATURE:
<223> OTHER INFORMATION: Description of Unknown:
      Cathepsin D cleavage domain sequence

<400> SEQUENCE: 21

Pro Ile Cys Phe Phe
1               5

<210> SEQ ID NO 22
<211> LENGTH: 8
<212> TYPE: PRT
<213> ORGANISM: Unknown
<220> FEATURE:
<223> OTHER INFORMATION: Description of Unknown:
      Cathepsin K cleavage domain sequence

<400> SEQUENCE: 22

Gly Gly Pro Arg Gly Leu Pro Gly
1               5

<210> SEQ ID NO 23
<211> LENGTH: 6
<212> TYPE: PRT
<213> ORGANISM: Unknown
<220> FEATURE:
<223> OTHER INFORMATION: Description of Unknown:
      Prostate Specific Antigen cleavage domain sequence

<400> SEQUENCE: 23

His Ser Ser Lys Leu Gln
1               5
```

-continued

```
<210> SEQ ID NO 24
<211> LENGTH: 7
<212> TYPE: PRT
<213> ORGANISM: Unknown
<220> FEATURE:
<223> OTHER INFORMATION: Description of Unknown:
      Prostate Specific Antigen cleavage domain sequence

<400> SEQUENCE: 24

His Ser Ser Lys Leu Gln Leu
1               5

<210> SEQ ID NO 25
<211> LENGTH: 9
<212> TYPE: PRT
<213> ORGANISM: Unknown
<220> FEATURE:
<223> OTHER INFORMATION: Description of Unknown:
      Prostate Specific Antigen cleavage domain sequence

<400> SEQUENCE: 25

His Ser Ser Lys Leu Gln Glu Asp Ala
1               5

<210> SEQ ID NO 26
<211> LENGTH: 10
<212> TYPE: PRT
<213> ORGANISM: Herpes Simplex virus

<400> SEQUENCE: 26

Leu Val Leu Ala Ser Ser Ser Phe Gly Tyr
1               5                   10

<210> SEQ ID NO 27
<211> LENGTH: 10
<212> TYPE: PRT
<213> ORGANISM: Human immunodeficiency virus

<400> SEQUENCE: 27

Gly Val Ser Gln Asn Tyr Pro Ile Val Gly
1               5                   10

<210> SEQ ID NO 28
<211> LENGTH: 10
<212> TYPE: PRT
<213> ORGANISM: Unknown
<220> FEATURE:
<223> OTHER INFORMATION: Description of Unknown:
      CMV Protease cleavage domain sequence

<400> SEQUENCE: 28

Gly Val Val Gln Ala Ser Cys Arg Leu Ala
1               5                   10

<210> SEQ ID NO 29
<211> LENGTH: 4
<212> TYPE: PRT
<213> ORGANISM: Unknown
<220> FEATURE:
<223> OTHER INFORMATION: Description of Unknown:
      Thrombin cleavage domain sequence
<220> FEATURE:
<221> NAME/KEY: MOD_RES
<222> LOCATION: (2)..(2)
<223> OTHER INFORMATION: Piperidine

<400> SEQUENCE: 29

Phe Xaa Arg Ser
1
```

-continued

```
<210> SEQ ID NO 30
<211> LENGTH: 6
<212> TYPE: PRT
<213> ORGANISM: Unknown
<220> FEATURE:
<223> OTHER INFORMATION: Description of Unknown:
      Thrombin cleavage domain sequence

<400> SEQUENCE: 30

Asp Pro Arg Ser Phe Leu
1               5

<210> SEQ ID NO 31
<211> LENGTH: 6
<212> TYPE: PRT
<213> ORGANISM: Unknown
<220> FEATURE:
<223> OTHER INFORMATION: Description of Unknown:
      Thrombin cleavage domain sequence

<400> SEQUENCE: 31

Pro Pro Arg Ser Phe Leu
1               5

<210> SEQ ID NO 32
<211> LENGTH: 4
<212> TYPE: PRT
<213> ORGANISM: Unknown
<220> FEATURE:
<223> OTHER INFORMATION: Description of Unknown:
      Caspase-3 cleavage domain sequence

<400> SEQUENCE: 32

Asp Glu Val Asp
1

<210> SEQ ID NO 33
<211> LENGTH: 5
<212> TYPE: PRT
<213> ORGANISM: Unknown
<220> FEATURE:
<223> OTHER INFORMATION: Description of Unknown:
      Caspase-3 cleavage domain sequence

<400> SEQUENCE: 33

Asp Glu Val Asp Pro
1               5

<210> SEQ ID NO 34
<211> LENGTH: 8
<212> TYPE: PRT
<213> ORGANISM: Unknown
<220> FEATURE:
<223> OTHER INFORMATION: Description of Unknown:
      Caspase-3 cleavage domain sequence

<400> SEQUENCE: 34

Lys Gly Ser Gly Asp Val Glu Gly
1               5

<210> SEQ ID NO 35
<211> LENGTH: 6
<212> TYPE: PRT
<213> ORGANISM: Unknown
<220> FEATURE:
<223> OTHER INFORMATION: Description of Unknown:
```

```
                Interleukin 1-beta converting enzyme cleavage domain sequence

<400> SEQUENCE: 35

Gly Trp Glu His Asp Gly
1               5

<210> SEQ ID NO 36
<211> LENGTH: 7
<212> TYPE: PRT
<213> ORGANISM: Unknown
<220> FEATURE:
<223> OTHER INFORMATION: Description of Unknown:
      Enterokinase cleavage domain sequence

<400> SEQUENCE: 36

Glu Asp Asp Asp Asp Lys Ala
1               5

<210> SEQ ID NO 37
<211> LENGTH: 9
<212> TYPE: PRT
<213> ORGANISM: Unknown
<220> FEATURE:
<223> OTHER INFORMATION: Description of Unknown:
      FAP cleavage domain sequence

<400> SEQUENCE: 37

Lys Gln Glu Gln Asn Pro Gly Ser Thr
1               5

<210> SEQ ID NO 38
<211> LENGTH: 6
<212> TYPE: PRT
<213> ORGANISM: Unknown
<220> FEATURE:
<223> OTHER INFORMATION: Description of Unknown:
      Kallikrein 2 cleavage domain sequence

<400> SEQUENCE: 38

Gly Lys Ala Phe Arg Arg
1               5

<210> SEQ ID NO 39
<211> LENGTH: 4
<212> TYPE: PRT
<213> ORGANISM: Unknown
<220> FEATURE:
<223> OTHER INFORMATION: Description of Unknown:
      Plasmin cleavage domain sequence

<400> SEQUENCE: 39

Asp Ala Phe Lys
1

<210> SEQ ID NO 40
<211> LENGTH: 4
<212> TYPE: PRT
<213> ORGANISM: Unknown
<220> FEATURE:
<223> OTHER INFORMATION: Description of Unknown:
      Plasmin cleavage domain sequence

<400> SEQUENCE: 40

Asp Val Leu Lys
1

<210> SEQ ID NO 41
```

```
<211> LENGTH: 4
<212> TYPE: PRT
<213> ORGANISM: Unknown
<220> FEATURE:
<223> OTHER INFORMATION: Description of Unknown:
      Plasmin cleavage domain sequence

<400> SEQUENCE: 41

Asp Ala Phe Lys
1

<210> SEQ ID NO 42
<211> LENGTH: 7
<212> TYPE: PRT
<213> ORGANISM: Unknown
<220> FEATURE:
<223> OTHER INFORMATION: Description of Unknown:
      TOP cleavage domain sequence

<400> SEQUENCE: 42

Ala Leu Leu Leu Ala Leu Leu
1               5

<210> SEQ ID NO 43
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Gly Ser Ser Gly Gly Ser
            100                 105                 110

Gly Gly Ser Gly Gly Ser Gly Leu Ser Gly Arg Ser Asp Asn His Gly
        115                 120                 125

Ser Ser Gly Thr Glu Val Gln Leu Val Glu Ser Gly Gly Gly Leu Val
    130                 135                 140

Gln Pro Gly Gly Ser Leu Arg Leu Ser Cys Ala Ala Ser Gly Tyr Ser
145                 150                 155                 160

Phe Thr Gly Tyr Tyr Ile His Trp Val Arg Gln Ala Pro Gly Lys Gly
                165                 170                 175

Leu Glu Trp Val Ala Arg Val Ile Pro Asn Ala Gly Gly Thr Ser Tyr
            180                 185                 190

Asn Gln Lys Phe Lys Gly Arg Phe Thr Leu Ser Val Asp Asn Ser Lys
        195                 200                 205

Asn Thr Ala Tyr Leu Gln Met Asn Ser Leu Arg Ala Glu Asp Thr Ala
    210                 215                 220
```

Val Tyr Tyr Cys Ala Arg Glu Gly Ile Tyr Trp Trp Gly Gln Gly Thr
225                 230                 235                 240

Leu Val Thr Val Ser Ser Gly Gly Gly Gly Asp Lys Thr His Thr
            245                 250                 255

Cys Pro Pro Cys Pro Ala Pro Glu Leu Leu Gly Gly Pro Ser Val Phe
                260                 265                 270

Leu Phe Pro Pro Lys Pro Lys Asp Thr Leu Met Ile Ser Arg Thr Pro
            275                 280                 285

Glu Val Thr Cys Val Val Val Asp Val Ser His Glu Asp Pro Glu Val
            290                 295                 300

Lys Phe Asn Trp Tyr Val Asp Gly Val Glu Val His Asn Ala Lys Thr
305                 310                 315                 320

Lys Pro Arg Glu Glu Gln Tyr Gly Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
            355                 360                 365

Lys Ala Lys Gly Gln Pro Arg Glu Pro Gln Val Tyr Thr Leu Pro Pro
370                 375                 380

Ser Arg Lys Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Lys Ser Asp
            420                 425                 430

Gly Ser Phe Phe Leu Tyr Ser Lys Leu Thr Val Asp Lys Ser Arg Trp
            435                 440                 445

Gln Gln Gly Asn Val Phe Ser Cys Ser Val Met His Glu Ala Leu His
            450                 455                 460

Asn His Tyr Thr Gln Lys Ser Leu Ser Leu Ser Pro Gly
465                 470                 475

<210> SEQ ID NO 44
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
                100                 105                 110

Gly Thr Thr Val Thr Val Ser Ser Gly Ser Gly Gly Ser Gly Gly
            115                 120                 125

Ser Gly Gly Ser Gly Leu Ser Gly Arg Ser Asp Asn His Gly Ser Ser
    130                 135                 140

Gly Thr Asp Ile Gln Met Thr Gln Ser Pro Ser Ser Leu Ser Ala Ser
145                 150                 155                 160

Val Gly Asp Arg Val Thr Ile Thr Cys Arg Ser Ser Gln Ser Leu Val
                165                 170                 175

His Ser Asn Gly Asn Thr Phe Leu His Trp Tyr Gln Gln Lys Pro Gly
            180                 185                 190

Lys Ala Pro Lys Leu Leu Ile Tyr Thr Val Ser Asn Arg Phe Ser Gly
        195                 200                 205

Val Pro Ser Arg Phe Ser Gly Ser Gly Ser Gly Thr Asp Phe Thr Leu
    210                 215                 220

Thr Ile Ser Ser Leu Gln Pro Glu Asp Phe Ala Thr Tyr Phe Cys Ser
225                 230                 235                 240

Gln Thr Thr His Val Pro Trp Thr Phe Gly Gln Gly Thr Lys Val Glu
                245                 250                 255

Ile Lys Gly Gly Gly Gly Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Gly Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Glu Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Asp Thr Thr Pro Pro Val Leu Asp Ser Asp Gly Ser Phe Phe
        435                 440                 445

Leu Tyr Ser Asp Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly
                485

<210> SEQ ID NO 45
<211> LENGTH: 489
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 45

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Gly Ser Ser Gly Gly Ser
            100                 105                 110

Gly Gly Ser Gly Gly Ser Gly Leu Ser Gly Arg Ser Asp Asn His Gly
        115                 120                 125

Ser Ser Gly Thr Gln Val Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Gly Tyr Tyr Met His Trp Val Arg Gln Ala Pro Gly Gln Gly
                165                 170                 175

Leu Glu Trp Met Gly Trp Ile Asn Pro Asp Ser Gly Gly Thr Asn Tyr
            180                 185                 190

Ala Gln Lys Phe Gln Gly Arg Val Thr Met Thr Arg Asp Thr Ser Ile
        195                 200                 205

Ser Thr Ala Tyr Met Glu Leu Asn Arg Leu Arg Ser Asp Asp Thr Ala
    210                 215                 220

Val Tyr Tyr Cys Ala Arg Asp Gln Pro Leu Gly Tyr Cys Thr Asn Gly
225                 230                 235                 240

Val Cys Ser Tyr Phe Asp Tyr Trp Gly Gln Gly Thr Leu Val Thr Val
                245                 250                 255

Ser Ser Gly Gly Gly Gly Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Gly Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Lys Glu
385                 390                 395                 400

```
Met Thr Lys Asn Gln Val Ser Leu Thr Cys Leu Val Lys Gly Phe Tyr
            405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Lys Ser Asp Gly Ser Phe Phe
            435                 440                 445

Leu Tyr Ser Lys Leu Thr Val Asp Lys Ser Arg Trp Gln Gln Gly Asn
450                 455                 460

Val Phe Ser Cys Ser Val Met His Glu Ala Leu His Asn His Tyr Thr
465                 470                 475                 480

Gln Lys Ser Leu Ser Leu Ser Pro Gly
            485

<210> SEQ ID NO 46
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Gly Ser Gly Gly Ser Gly Gly
            115                 120                 125

Ser Gly Gly Ser Gly Leu Ser Gly Arg Ser Asp Asn His Gly Ser Ser
            130                 135                 140

Gly Thr Asp Ile Gln Met Thr Gln Ser Pro Ser Ser Val Ser Ala Ser
145                 150                 155                 160

Val Gly Asp Arg Val Thr Ile Thr Cys Arg Ala Ser Gln Gly Ile Tyr
                165                 170                 175

Ser Trp Leu Ala Trp Tyr Gln Gln Lys Pro Gly Lys Ala Pro Asn Leu
            180                 185                 190

Leu Ile Tyr Thr Ala Ser Thr Leu Gln Ser Gly Val Pro Ser Arg Phe
            195                 200                 205

Ser Gly Ser Gly Ser Gly Thr Asp Phe Thr Leu Thr Ile Ser Ser Leu
            210                 215                 220

Gln Pro Glu Asp Phe Ala Thr Tyr Tyr Cys Gln Gln Ala Asn Ile Phe
225                 230                 235                 240

Pro Leu Thr Phe Gly Gly Gly Thr Lys Val Glu Ile Lys Gly Gly Gly
            245                 250                 255

Gly Gly Asp Lys Thr His Thr Cys Pro Pro Cys Pro Ala Pro Glu Leu
```

```
                    260                 265                 270
Leu Gly Gly Pro Ser Val Phe Leu Phe Pro Lys Pro Lys Asp Thr
            275                 280                 285
Leu Met Ile Ser Arg Thr Pro Glu Val Thr Cys Val Val Asp Val
        290                 295                 300
Ser His Glu Asp Pro Glu Val Lys Phe Asn Trp Tyr Val Asp Gly Val
305                 310                 315                 320
Glu Val His Asn Ala Lys Thr Lys Pro Arg Glu Glu Gln Tyr Gly Ser
                325                 330                 335
Thr Tyr Arg Val Val Ser Val Leu Thr Val Leu His Gln Asp Trp Leu
            340                 345                 350
Asn Gly Lys Glu Tyr Lys Cys Lys Val Ser Asn Lys Ala Leu Pro Ala
        355                 360                 365
Pro Ile Glu Lys Thr Ile Ser Lys Ala Lys Gly Gln Pro Arg Glu Pro
    370                 375                 380
Gln Val Tyr Thr Leu Pro Pro Ser Arg Glu Glu Met Thr Lys Asn Gln
385                 390                 395                 400
Val Ser Leu Thr Cys Leu Val Lys Gly Phe Tyr Pro Ser Asp Ile Ala
                405                 410                 415
Val Glu Trp Glu Ser Asn Gly Gln Pro Glu Asn Asn Tyr Asp Thr Thr
            420                 425                 430
Pro Pro Val Leu Asp Ser Asp Gly Ser Phe Phe Leu Tyr Ser Asp Leu
        435                 440                 445
Thr Val Asp Lys Ser Arg Trp Gln Gln Gly Asn Val Phe Ser Cys Ser
    450                 455                 460
Val Met His Glu Ala Leu His Asn His Tyr Thr Gln Lys Ser Leu Ser
465                 470                 475                 480

Leu Ser Pro Gly

<210> SEQ ID NO 47
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Gln Met Thr Gln Ser Pro Ser Thr Leu Ser Ala Ser Val Gly
1               5                   10                  15
Asp Arg Val Thr Ile Thr Cys Lys Cys Gln Leu Ser Val Gly Tyr Met
            20                  25                  30
His Trp Tyr Gln Gln Lys Pro Gly Lys Ala Pro Lys Leu Leu Ile Tyr
        35                  40                  45
Asp Thr Ser Lys Leu Ala Ser Gly Val Pro Ser Arg Phe Ser Gly Ser
    50                  55                  60
Gly Ser Gly Thr Glu Phe Thr Leu Thr Ile Ser Ser Leu Gln Pro Asp
65                  70                  75                  80
Asp Phe Ala Thr Tyr Tyr Cys Phe Gln Gly Ser Gly Tyr Pro Phe Thr
                85                  90                  95
Phe Gly Gly Gly Thr Lys Leu Glu Ile Lys Gly Ser Ser Gly Gly Ser
            100                 105                 110
Gly Gly Ser Gly Gly Ser Gly Leu Ser Gly Arg Ser Asp Asn His Gly
        115                 120                 125
Ser Ser Gly Thr Gln Val Gln Leu Val Glu Ser Gly Gly Gly Val Val
```

```
                130             135              140
Gln Pro Gly Arg Ser Leu Arg Leu Ser Cys Ala Ala Ser Gly Phe Thr
145                 150                 155                 160

Phe Ser Ser Tyr Thr Met His Trp Val Arg Gln Ala Pro Gly Lys Gly
                165                 170                 175

Leu Glu Trp Val Thr Phe Ile Ser Tyr Asp Gly Asn Asn Lys Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Ile Tyr Tyr Cys Ala Arg Thr Gly Trp Leu Gly Pro Phe Asp Tyr Trp
225                 230                 235                 240

Gly Gln Gly Thr Leu Val Thr Val Ser Ser Gly Gly Gly Gly Asp
                245                 250                 255

Lys Thr His Thr Cys Pro Pro Cys Pro Ala Pro Glu Leu Leu Gly Gly
                260                 265                 270

Pro Ser Val Phe Leu Phe Pro Pro Lys Pro Lys Asp Thr Leu Met Ile
            275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Gly Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Lys Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Lys Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly
```

<210> SEQ ID NO 48
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Thr Leu Arg Glu Ser Gly Pro Ala Leu Val Lys Pro Thr Gln

-continued

```
1               5                   10                  15
Thr Leu Thr Leu Thr Cys Thr Phe Ser Gly Phe Ser Leu Ser Thr Ser
                20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
                100                 105                 110

Gly Thr Thr Val Thr Val Ser Ser Gly Ser Ser Gly Gly Ser Gly Gly
                115                 120                 125

Ser Gly Gly Ser Gly Leu Ser Gly Arg Ser Asp Asn His Gly Ser Ser
130                 135                 140

Gly Thr Glu Ile Val Leu Thr Gln Ser Pro Gly Thr Leu Ser Leu Ser
145                 150                 155                 160

Pro Gly Glu Arg Ala Thr Leu Ser Cys Arg Ala Ser Gln Ser Val Gly
                165                 170                 175

Ser Ser Tyr Leu Ala Trp Tyr Gln Gln Lys Pro Gly Gln Ala Pro Arg
            180                 185                 190

Leu Leu Ile Tyr Gly Ala Phe Ser Arg Ala Thr Gly Ile Pro Asp Arg
            195                 200                 205

Phe Ser Gly Ser Gly Ser Gly Thr Asp Phe Thr Leu Thr Ile Ser Arg
210                 215                 220

Leu Glu Pro Glu Asp Phe Ala Val Tyr Tyr Cys Gln Gln Tyr Gly Ser
225                 230                 235                 240

Ser Pro Trp Thr Phe Gly Gln Gly Thr Lys Val Glu Ile Lys Gly Gly
                245                 250                 255

Gly Gly Gly Asp Lys Thr His Thr Cys Pro Pro Cys Pro Ala Pro Glu
                260                 265                 270

Leu Leu Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
            290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Gly
                325                 330                 335

Ser Thr Tyr Arg Val Val Ser Val Leu Thr Val Leu His Gln Asp Trp
                340                 345                 350

Leu Asn Gly Lys Glu Tyr Lys Cys Lys Val Ser Asn Lys Ala Leu Pro
            355                 360                 365

Ala Pro Ile Glu Lys Thr Ile Ser Lys Ala Lys Gly Gln Pro Arg Glu
            370                 375                 380

Pro Gln Val Tyr Thr Leu Pro Pro Ser Arg Glu Glu Met Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Asp Thr
                420                 425                 430
```

```
Thr Pro Pro Val Leu Asp Ser Asp Gly Ser Phe Phe Leu Tyr Ser Asp
            435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly
                485

<210> SEQ ID NO 49
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Gly Ser Ser Gly Gly Ser
            100                 105                 110

Gly Gly Ser Gly Gly Ser Gly Leu Ser Gly Arg Ser Asp Asn His Gly
        115                 120                 125

Ser Ser Gly Thr Gln Val Gln Leu Val Glu Ser Gly Gly Gly Val Val
130                 135                 140

Gln Pro Gly Arg Ser Leu Arg Leu Ser Cys Ala Ala Ser Gly Phe Thr
145                 150                 155                 160

Phe Ser Ser Tyr Gly Met His Trp Val Arg Gln Ala Pro Gly Lys Gly
                165                 170                 175

Leu Glu Trp Val Ala Val Ile Trp Tyr Asp Gly Ser Asn Lys Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Asp Pro Arg Gly Ala Thr Leu Tyr Tyr Tyr
225                 230                 235                 240

Tyr Tyr Gly Met Asp Val Trp Gly Gln Gly Thr Thr Val Thr Val Ser
                245                 250                 255

Ser Gly Gly Gly Gly Gly Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
```

```
                    290                 295                 300
Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Gly Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
    370                 375                 380

Pro Arg Glu Pro Gln Val Tyr Thr Leu Pro Pro Ser Arg Lys Glu Met
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Lys Ser Asp Gly Ser Phe Phe Leu
        435                 440                 445

Tyr Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480

Lys Ser Leu Ser Leu Ser Pro Gly
                485

<210> SEQ ID NO 50
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Gly Ser Gly Gly Ser Gly Gly
        115                 120                 125

Ser Gly Gly Ser Gly Leu Ser Gly Arg Ser Asp Asn His Gly Ser Ser
    130                 135                 140

Gly Thr Asp Ile Gln Met Thr Gln Ser Pro Ser Ser Leu Ser Ala Ser
145                 150                 155                 160
```

-continued

Val Gly Asp Arg Val Thr Ile Thr Cys Arg Ala Ser Gln Ser Ile Asn
                165                 170                 175

Ser Tyr Leu Asp Trp Tyr Gln Gln Lys Pro Gly Lys Ala Pro Lys Leu
            180                 185                 190

Leu Ile Tyr Ala Ala Ser Ser Leu Gln Ser Gly Val Pro Ser Arg Phe
        195                 200                 205

Ser Gly Ser Gly Ser Gly Thr Asp Phe Thr Leu Thr Ile Ser Ser Leu
    210                 215                 220

Gln Pro Glu Asp Phe Ala Thr Tyr Tyr Cys Gln Gln Tyr Tyr Ser Thr
225                 230                 235                 240

Pro Phe Thr Phe Gly Pro Gly Thr Lys Val Glu Ile Lys Gly Gly Gly
                245                 250                 255

Gly Gly Asp Lys Thr His Thr Cys Pro Pro Cys Pro Ala Pro Glu Leu
            260                 265                 270

Leu Gly Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Gly Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
    370                 375                 380

Gln Val Tyr Thr Leu Pro Pro Ser Arg Glu Glu Met Thr Lys Asn Gln
385                 390                 395                 400

Val Ser Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Asp Thr Thr
            420                 425                 430

Pro Pro Val Leu Asp Ser Asp Gly Ser Phe Phe Leu Tyr Ser Asp Leu
        435                 440                 445

Thr Val Asp Lys Ser Arg Trp Gln Gln Gly Asn Val Phe Ser Cys Ser
    450                 455                 460

Val Met His Glu Ala Leu His Asn His Tyr Thr Gln Lys Ser Leu Ser
465                 470                 475                 480

Leu Ser Pro Gly

<210> SEQ ID NO 51
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Ser Ser Gly Gly Ser Gly Gly Ser Gly Gly Ser Gly Leu Ser Gly
1               5                   10                  15

Arg Ser Asp Asn His Gly Ser Ser Gly Thr
            20                  25

```
<210> SEQ ID NO 52
<211> LENGTH: 8
<212> TYPE: PRT
<213> ORGANISM: Unknown
<220> FEATURE:
<223> OTHER INFORMATION: Description of Unknown:
      cleavage domain sequence

<400> SEQUENCE: 52

Gly Pro Leu Gly Ile Ala Gly Gln
1               5

<210> SEQ ID NO 53
<211> LENGTH: 8
<212> TYPE: PRT
<213> ORGANISM: Unknown
<220> FEATURE:
<223> OTHER INFORMATION: Description of Unknown:
      cleavage domain sequence

<400> SEQUENCE: 53

Ala Val Arg Trp Leu Leu Thr Ala
1               5

<210> SEQ ID NO 54
<211> LENGTH: 6
<212> TYPE: PRT
<213> ORGANISM: Unknown
<220> FEATURE:
<223> OTHER INFORMATION: Description of Unknown:
      cleavage domain sequence

<400> SEQUENCE: 54

Arg Arg Arg Arg Arg Arg
1               5

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-10 "Gly Ser"
      repeating units

<400> SEQUENCE: 55

Gly Ser Gly Ser Gly Ser Gly Ser Gly Ser Gly Ser Gly Ser Gly Ser
1               5                   10                  15

Gly Ser Gly Ser
            20

<210> SEQ ID NO 56
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-10 "Gly Gly Ser"
      repeating units

<400> SEQUENCE: 56
```

Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 57
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Gly
      Ser" repeating units

<400> SEQUENCE: 57

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
            35                  40

<210> SEQ ID NO 58
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Ser
      Gly" repeating units

<400> SEQUENCE: 58

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
            35                  40

<210> SEQ ID NO 59
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Ser
      Gly Gly" repeating units

<400> SEQUENCE: 59

Gly Gly Ser Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Gly Gly Gly Gly Ser Gly Gly Gly Ser
        35                  40                  45

Gly Gly
    50

<210> SEQ ID NO 60
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Ser" repeating units

<400> SEQUENCE: 60

Gly Gly Gly Gly Ser Gly Gly Gly Ser Gly Gly Gly Gly Ser Gly
1               5                   10                  15

Gly Gly Ser Gly Gly Gly Gly Ser Gly Gly Gly Gly Ser Gly Gly
            20                  25                  30

Gly Gly Ser Gly Gly Gly Ser Gly Gly Gly Ser Gly Gly Gly
        35                  40                  45

Gly Ser
    50

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Gly Gly Gly Ser Gly Gly Gly Gly Ser Gly Gly Gly Gly Ser Gly
1               5                   10                  15

Gly Gly Gly Ser
            20

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gly Gly Gly Ser Gly Gly Gly Gly Ser Gly Gly Gly Gly Ser
1               5                   10                  15

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Pro Leu Gly Leu Trp Ala
1               5

```
<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Val Leu Ala Glu Ala
1               5

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Asp Val Val Cys Cys Ser Met Ser Tyr
1               5                   10

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Gly Ile Glu Gly Arg Gly Ser
1               5

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Phe Leu Gly
1
```

INDUCIBLE MONOVALENT ANTIGEN BINDING PROTEIN

CROSS-REFERENCE

This application claims the benefit of U.S. Provisional Application No. 62/465,000, filed Feb. 28, 2017, which is incorporated by reference herein in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if set forth in their entireties.

SEQUENCE LISTING

The instant application contains a Sequence Listing which has been filed electronically in ASCII format and is hereby incorporated by reference in its entirety. Said ASCII copy, created on Sep. 24, 2019, is named 47517-710_831_SL.txt and is 49,801 bytes in size.

BACKGROUND OF THE INVENTION

The present disclosure provides an inducible monovalent target-binding protein which are activated upon protease cleavage, and can be used for diagnosing and treating cancers.

SUMMARY OF THE INVENTION

In one embodiment is provided, an inducible monovalent target-binding protein, wherein the protein comprises a first polypeptide chain and a second polypeptide chain,
  the first polypeptide chain comprising: a VH target-binding domain (VH), an inactive VL domain (iVL) that binds to the VH domain, a linker (L1), and a first monomeric Fc domain (Fc1) comprising a CH3 and a CH2 domain;
  the second polypeptide chain comprising: a VL target-binding domain (VL), an inactive VH domain (iVH) that binds to the VL domain, a linker (L6), a second monomeric Fc domain (Fc2) comprising a CH3 and a CH2 domain;
wherein the iVL and the iVH each comprise at least one protease cleavage site, wherein upon activation by protease cleavage of the at least one protease cleavage site of both the iVL and the iVH, the VH and the VL associate to form an active target-binding domain, and wherein the CH3 domains of the Fc1 and Fc2 form a heterodimer.

In one embodiment is provided, An inducible monovalent target-binding protein, wherein the protein comprises a first polypeptide chain and a second polypeptide chain,
  the first polypeptide chain comprising: a VL target-binding domain (VL), an inactive VH domain (iVH) that binds to the VL domain, a linker (L1'), and a first monomeric Fc domain (Fc1) comprising a CH3 and a CH2 domain;
  the second polypeptide chain comprising: a VH target-binding domain (VH), an inactive VL domain (iVL) that binds to the VH domain, a linker (L6'), a second monomeric Fc domain (Fc2) comprising a CH3 and a CH2 domain;
wherein the iVH and the iVL each comprise at least one protease cleavage site, wherein upon activation by protease cleavage of the at least one protease cleavage site of both iVH and the iVL, the VL and the VH associate to form an active target-binding domain, and wherein the CH3 domains of the Fc1 and the Fc2 form a heterodimer.

In some embodiments, the iVL comprises a CDRL1, CDRL2, and CDRL3, and the at least one protease cleavage site of the iVL is located within the CDRL1, CDRL2, or CDRL3. In some embodiments, the iVH comprises a CDRH1, CDRH2, and CDRH3, and the at least one protease cleavage site of the iVH is located within the CDRH1, CDRH2, or CDRH3. In some embodiments, the first polypeptide chain comprises a further protease cleavage site, and wherein the second polypeptide comprises a further protease cleavage site. In some embodiments, the further protease cleavage site of the first polypeptide chain is located within the L1 or the L1', and the further protease cleavage site of the second polypeptide chain is located within the L6 or the L6'. In some embodiments, the Fc1 and Fc2 each independently comprise one or more amino acid substitutions favoring formation of a heterodimeric Fc region. In some embodiments, the CH3 domain of the Fc1 comprises a substitution of an amino acid with a negatively charged amino acid, and the CH3 domain of the Fc2 comprises a substitution of an amino acid with a positively charged amino acid. In some embodiments, the CH3 domain of the Fc1 comprises a substitution of an amino acid with a positively charged amino acid, and the CH3 domain of the Fc2 comprises a substitution of an amino acid with a negatively charged amino acid. In some embodiments, the iVH and the iVL each independently comprise one or more mutations that prohibit target binding of said domains. In some embodiments, the VH, iVL, and the L1 or the L1' of the first polypeptide form a scFv. In some embodiments, the VL, iVH, and the L6 or the L6' of the second polypeptide form a scFv.

In one embodiment is provided, an inducible monovalent target-binding protein, wherein the protein comprises a first scFv (scFv1) and a second scFv (scFv2), and a first (Fc1) and a second (Fc2) monomeric Fc domain, each comprising a CH2 domain and a CH3 domain,
  the scFv1 comprising: a VH target-binding domain (VH), an inactive VL domain (iVL) that binds to the VH domain, and a (L1);
  the scFv2 comprising: a VL target-binding domain (VL), an inactive VH domain (iVH) that binds to the VL domain, and a linker (L6);
wherein the scFv1 and the scFv2 each comprise at least one protease cleavage site, wherein upon activation by protease cleavage of the protease cleavage sites, the VH and the VL associate to form an active target-binding domain, and wherein the Fc1 and the Fc2 form a Fc region comprising a heterodimeric CH3 domain.

In one embodiment is provided, an inducible monovalent target-binding protein, wherein the protein comprises a first scFv (scFv1) and a second scFv (scFv2), and a first (Fc1) and a second (Fc2) monomeric Fc domain, each comprising a CH2 domain and a CH3 domain,
  the scFv1 comprising: a VL target-binding domain (VL), an inactive VH domain (iVH) that binds to the VL domain, and a linker (L1');
  the scFv2 comprising: a VH target-binding domain (VH), an inactive VL domain (iVL) that binds to the VH domain, and a linker (L6');
wherein the scFv1 and the scFv2 each comprise at least one protease cleavage site, wherein upon activation by protease cleavage of the at least one protease cleavage site of both the scFv1 and the scFv2, the VL and the VH associate to form an active target-binding domain, and wherein the Fc1 and the Fc2 form a Fc region comprising a heterodimeric CH3 domain.

In some embodiments, the iVL comprises a CDRL1, CDRL2, and CDRL3, and the at least one protease cleavage site of the iVL is located within the CDRL1, CDRL2, or CDRL3. In some embodiments, the iVH comprises a CDRH1, CDRH2, and CDRH3, and the at least one protease cleavage site of the iVH is located within the CDRH1, CDRH2, or CDRH3. In some embodiments, the scFv1 comprises a further protease cleavage site, and wherein the scFv2 comprises a further protease cleavage site. In some embodiments, the further protease cleavage site of the scFv1 is located within the L1 or the L1', and the further protease cleavage site of the scFv2 is located within L6 or L6'. In some embodiments, the Fc1 and the Fc2 each independently comprise one or more amino acid substitution in their respective CH3 domain favoring formation of the Fc region comprising a heterodimeric CH3 domain. In some embodiments, the CH3 domain of the Fc1 comprises a substitution of an amino acid with a negatively charged amino acid, and the CH3 domain of the Fc2 comprises a substitution of an amino acid with a positively charged amino acid. In some embodiments, the CH3 domain of the Fc1 comprises a substitution of an amino acid with a positively charged amino acid, and the CH3 domain of the Fc2 comprises a substitution of an amino acid with a negatively charged amino acid. In some embodiments, the iVH and the iVL domains each independently comprise one or more mutation that prohibit target binding of said domains. In some embodiments, the active target-binding domain binds to a target expressed on a tumor cell. In some embodiments, the active target-binding domain binds to a tumor antigen. In some embodiments, the active target-binding domain binds to an immune checkpoint protein. In some embodiments, the active target-binding domain binds to CD27, CD40, OX40, GITR, CD137, B7, CD28, ICOS, A2AR, B7-H3, B7-H4, BTLA, CTLA-4, IDO, KIR, LAG3, PD-1, PD-L1, TIM-3, VISTA. In some embodiments, the at least one protease cleavage site is recognized by at least one of a serine protease, a cysteine protease, an aspartate protease, a threonine protease, a glutamic acid protease, a metalloproteinase, a gelatinase, and an asparagine peptide lyase. In some embodiments, the at least one protease cleavage site is recognized by at least one of a Cathepsin B, a Cathepsin C, a Cathepsin D, a Cathepsin E, a Cathepsin K, a Cathepsin L, a kallikrein, a hK1, a hK10, a hK15, a plasmin, a collagenase, a Type IV collagenase, a stromelysin, a Factor Xa, a chymotrypsin-like protease, a trypsin-like protease, a elastase-like protease, a subtilisin-like protease, an actinidain, a bromelain, a calpain, a caspase, a caspase-3, a Mir1-CP, a papain, a HIV-1 protease, a HSV protease, a CMV protease, a chymosin, a renin, a pepsin, a matriptase, a legumain, a plasmepsin, a nepenthesin, a metalloexopeptidase, a metalloendopeptidase, a matrix metalloprotease (MMP), a MMP1, a MMP2, a MMP3, a MMP8, a MMP9, a MMP10, a MMP11, a MMP12, a MMP13, a MMP14, an ADAM10, an ADAM12, an urokinase plasminogen activator (uPA), an enterokinase, a prostate-specific target (PSA, hK3), an interleukin-1β converting enzyme, a thrombin, a FAP (FAP-α), a dipeptidyl peptidase, and a dipeptidyl peptidase IV (DPPIV/CD26).

One embodiment provides an inducible monovalent target-binding protein, wherein the protein comprises a first polypeptide chain and a second polypeptide chain,
  the first polypeptide chain comprising: a VH target-binding domain (VH), an inactive VL domain (iVL) that binds to the VH domain, a linker (L1), and a first monomeric Fc domain (Fc1) comprising a CH3 and a CH2 domain;
  the second polypeptide chain comprising: a VL target-binding domain (VL), an inactive VH domain (iVH) that binds to the VL domain, a linker (L6), a second monomeric Fc domain (Fc2) comprising a CH3 and a CH2 domain;
wherein the L1 and L6 each comprise at least one protease cleavage site, wherein upon activation by protease cleavage of the at least one protease cleavage site of both L1 and L6, the VH and the VL associate to form an active target-binding domain, and wherein the CH3 domains of the Fc1 and Fc2 form a heterodimer.

One embodiment provides an inducible monovalent target-binding protein, wherein the protein comprises a first polypeptide chain and a second polypeptide chain,
  the first polypeptide chain comprising: a VL target-binding domain (VL), an inactive VH domain (iVH) that binds to the VL domain, a linker (L1'), and a first monomeric Fc domain (Fc1) comprising a CH3 and a CH2 domain;
  the second polypeptide chain comprising: a VH target-binding domain (VH), an inactive VL domain (iVL) that binds to the VH domain, a linker (L6'), a second monomeric Fc domain (Fc2) comprising a CH3 and a CH2 domain;
wherein the L1' and L6' each comprise at least one protease cleavage site, wherein upon activation by protease cleavage of the at least one protease cleavage site of both L1' and L6', the VL and the VH associate to form an active target-binding domain, and wherein the CH3 domains of the Fc1 and Fc2 form a heterodimer.

In some embodiments, the inducible monovalent target-binding protein of claim 29 or 30, wherein the iVL comprises a CDRL1, CDRL2, and CDRL3. In some embodiments, the iVH comprises a CDRH1, CDRH2, and CDRH3. In some embodiments, the Fc1 and the Fc2 each independently comprise one or more amino acid substitutions favoring formation of a heterodimeric Fc region. In some embodiments, the CH3 domain of the Fc1 comprises a substitution of an amino acid with a negatively charged amino acid, and the CH3 domain of the Fc2 comprises a substitution of an amino acid with a positively charged amino acid. In some embodiments, the CH3 domain of the Fc1 comprises a substitution of an amino acid with a positively charged amino acid, and the CH3 domain of the Fc2 comprises a substitution of an amino acid with a negatively charged amino acid. In some embodiments, the iVH and the iVL each independently comprise one or more mutations that prohibit target binding of said domains. In some embodiments, the VH, the iVL, and the L1 or the L1' of the first polypeptide form a scFv. In some embodiments, the iVH, and the L6 or the L6' of the second polypeptide form a scFv.

One embodiment provides an inducible monovalent target-binding protein, wherein the protein comprises a first scFv (scFv1) and a second scFv (scFv2), and a first (Fc1) and a second (Fc2) monomeric Fc domain, each comprising a CH2 domain and a CH3 domain,
  the scFv1 comprising: a VH target-binding domain (VH), an inactive VL domain (iVL) that binds to the VH domain, and a (L1);
  the scFv2 comprising: a VL target-binding domain (VL), an inactive VH domain (iVH) that binds to the VL domain, and a linker (L6);

wherein the scFv1 and the scFv2 each comprise at least one protease cleavage site, wherein upon activation by protease cleavage of the protease cleavage sites, the VH and the VL associate to form an active target-binding domain, and wherein Fc1 and Fc2 form a Fc region comprising a heterodimeric CH3 domain.

One embodiment provides an inducible monovalent target-binding protein, wherein the protein comprises a first scFv (scFv1) and a second scFv (scFv2), and a first (Fc1) and a second (Fc2) monomeric Fc domain, each comprising a CH2 domain and a CH3 domain,
- the scFv1 comprising: a VL target-binding domain (VL), an inactive VH domain (iVH) that binds to the VL domain, and a linker (L1');
- the scFv2 comprising: a VH target-binding domain (VH), an inactive VL domain (iVL) that binds to the VH domain, and a linker (L6');

wherein the scFv1 and the scFv2 each comprise at least one protease cleavage site, wherein upon activation by protease cleavage of the at least one protease cleavage site of both the scFv1 and the scFv2, the VL and the VH associate to form an active target-binding domain, and wherein the Fc1 and Fc2 form a Fc region comprising a heterodimeric CH3 domain.

In some embodiments, the iVL comprises a CDRL1, CDRL2, and CDRL3. In some embodiments, the iVH comprises a CDRH1, CDRH2, and CDRH3. In some embodiments, the at least one protease cleavage site of the scFv1 is located within the L1 or the L1'. In some embodiments, the further protease cleavage site of the scFv2 is located within the L6 or the L6'. In some embodiments, the Fc1 and the Fc2 each independently comprise one or more amino acid substitution in their respective CH3 domain favoring formation of the Fc region comprising a heterodimeric CH3 domain. In some embodiments, the CH3 domain of the Fc1 comprises a substitution of an amino acid with a negatively charged amino acid, and the CH3 domain of the Fc2 comprises a substitution of an amino acid with a positively charged amino acid. In some embodiments, the CH3 domain of the Fc1 comprises a substitution of an amino acid with a positively charged amino acid, and the CH3 domain of the Fc2 comprises a substitution of an amino acid with a negatively charged amino acid. In some embodiments, the iVH and the iVL domains each independently comprise one or more mutation that prohibit target binding of said domains. In some embodiments, the active target-binding domain binds to a target expressed on a tumor cell. In some embodiments, the active target-binding domain binds to a tumor antigen. In some embodiments, the e active target-binding domain binds to an immune checkpoint protein. In some embodiments, the active target-binding domain binds to CD27, CD40, OX40, GITR, CD137, B7, CD28, ICOS, A2AR, B7-H3, B7-H4, BTLA, CTLA-4, IDO, KIR, LAG3, PD-1, PD-L1, TIM-3, VISTA. In some embodiments, the at least one protease cleavage site is recognized by at least one of a serine protease, a cysteine protease, an aspartate protease, a threonine protease, a glutamic acid protease, a metalloproteinase, a gelatinase, and a asparagine peptide lyase.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

Figure 1:
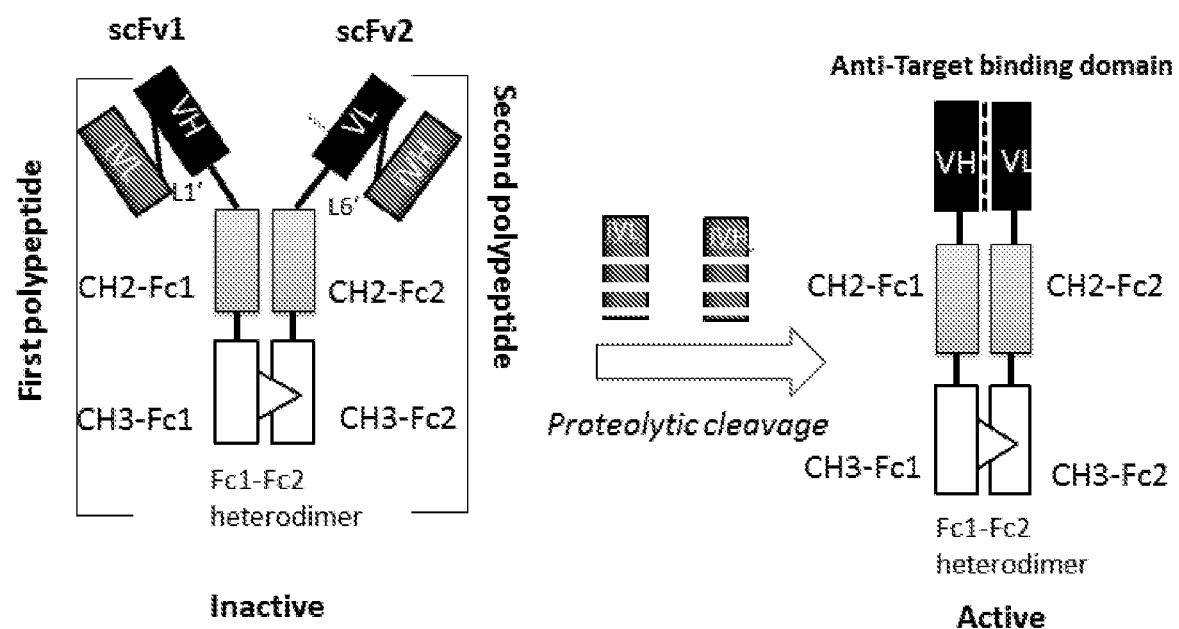
FIG. 1 shows an embodiment of the inducible monovalent target-binding protein of the present disclosure illustrating activation of the target-binding protein upon proteolytic cleavage of at least one protease cleavage site in the inactive VL domain and at least one protease cleavage site in the inactive VH domain.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual," "patient," or "subject" are used interchangeably. None of the terms require or are limited to situation characterized by the supervision (e.g. constant or intermittent) of a health care worker (a doctor, a registered nurse, a nurse practitioner, a physician's assistant, an orderly, or a hospice worker).

The term "Framework" or "FR" residues (or regions) refer to variable domain residues other than the CDR or hypervariable region residues as herein defined. A "human consensus framework" is a framework which represents the most commonly occurring amino acid residue in a selection of human immunoglobulin VL or VH framework sequences.

As used herein, "Variable region" or "variable domain" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the βsheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. "Variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (, residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence. It is not intended that CDRs of the present disclosure necessarily correspond to the Kabat numbering convention.

A "single chain Fv" or "scFv", as used herein, refers to a binding protein in which the variable domains of the heavy chain and of the light chain of a traditional two chain antibody are joined to form one chain. Typically, a linker peptide is inserted between the two chains to allow for proper folding and creation of an active binding site.

A "cleavage site for a protease," as meant herein, is an amino acid sequence that can be cleaved by a protease, such as, for example, a matrix metalloproteinase or a furin. Examples of such sites include Gly-Pro-Leu-Gly-Ile-Ala-Gly-Gln (SEQ ID NO: 52) or Ala-Val-Arg-Trp-Leu-Leu-Thr-Ala (SEQ ID NO: 53), which can be cleaved by metalloproteinases, and Arg-Arg-Arg-Arg-Arg-Arg (SEQ ID NO: 54), which is cleaved by a furin. In therapeutic applications, the protease cleavage site can be cleaved by a protease that is produced by target cells, for example cancer cells or infected cells, or pathogens.

As used herein, "elimination half-time" is used in its ordinary sense, as is described in *Goodman and Gillman's The Pharmaceutical Basis of Therapeutics* 21-25 (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, $t_{1/2}$ the time required for 50% completion of the process. The units of these two constants are $time^{-1}$ and time, respectively. A first-order rate constant and the half-time of the reaction are simply related ($k \times t_{1/2} = 0.693$) and may be interchanged accordingly. Since first-order elimination kinetics dictates that a constant fraction of drug is lost per unit time, a plot of the log of drug concentration versus time is linear at all times following the initial distribution phase (i.e. after drug absorption and distribution are complete). The half-time for drug elimination can be accurately determined from such a graph.

Figure 2:
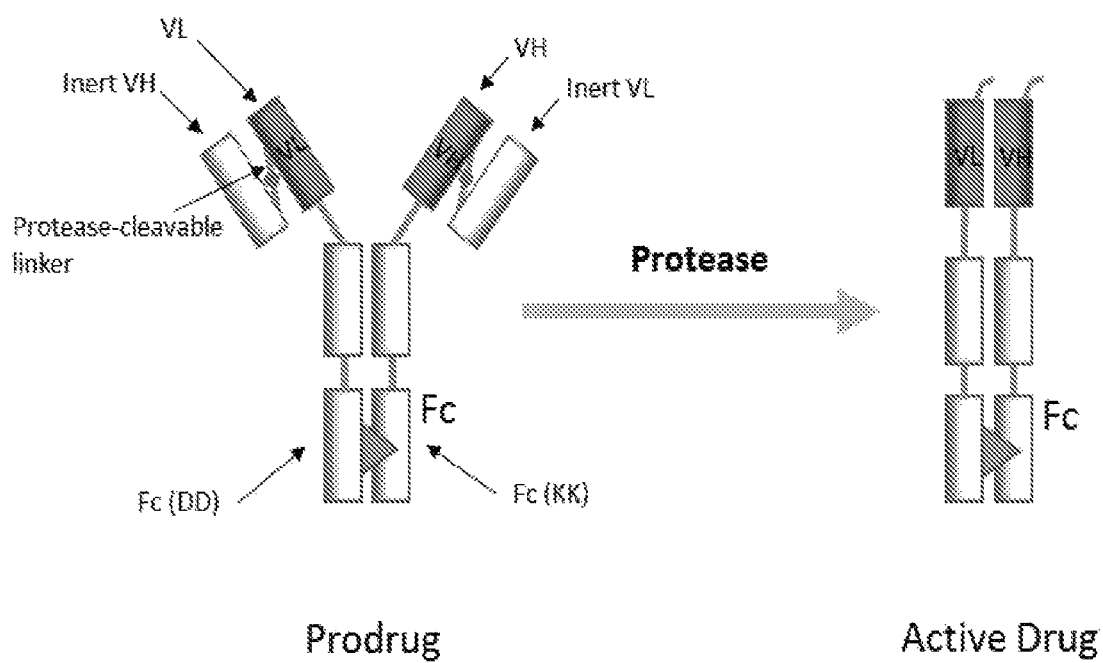
FIG. 2 shows an inducible monovalent antibody according to the present disclosure illustrating activation of the antibody, from its prodrug from to the active drug form, upon proteolytic cleavage of at least one protease cleavage site in the linker between the VL and the inactive VH domain of one polypeptide chain and the linker between the VH and inactive VL domain of another polypeptide chain.

Described herein are inducible monovalent target-binding proteins, pharmaceutical compositions as well as nucleic acids, recombinant expression vectors, and host cells for making such inducible monovalent binding proteins. Also provided are methods of using the disclosed inducible monovalent binding proteins in the prevention, and/or treatment of diseases, conditions and disorders. The inducible monovalent target-binding proteins of this disclosure are heteromultimeric proteins having a binding inactive form and an active form. In the binding inactive form, the protein has an immunoglobulin like structure with two arms, whereas in the active form the two arms associate with each other to form a monovalent structure, as shown in FIGS. 1 and 2. The inducible monovalent target-binding proteins are activated by cleavage of protease sites located within at least two of the domains of the heteromultimeric structure. In some embodiments, the inducible monovalent binding proteins are capable of specifically binding to a tumor antigen. In some embodiments, the inducible monovalent target-binding proteins are half-life extended through an Fc domain, and accordingly has a prolonged elimination half-life. In some instance, the inducible monovalent target-binding proteins are heteromultimeric antibodies. In some cases when a normal or healthy tissue expresses the same antigens as a tumor cell, toxicities are possible due to off-tumor antigen binding. In some embodiments, the inducible monovalent target-binding proteins disclosed herein are advantageously activated in a tumor tissue specific manner, upon exposure to proteases prevalent in tumor microenvironment. The inhibitory domains obstruct the binding domains and accordingly prevent binding of the proteins to their targets until the inhibitory domains are cleaved by proteases.

Inactive Domains

In one aspect, the disclosure provides an inducible monovalent target-binding protein comprising at least two inactive domains. In some embodiments, the inactive domains comprise protease cleavage sites. The inactive domains are alternatively referred to as inhibitory domains or inert domains. Examples of inactive domains include but are not limited to a variable heavy domain (VH), a variable light domain (VL), an scFv comprising a VH and a VL domain, a single domain antibody, or a variable domain of camelid derived nanobody (VHH), a non-Ig binding domain, i.e., antibody mimetic, such as anticalins, affilins, affibody molecules, affimers, affitins, alphabodies, avimers, DARPins, fynomers, kunitz domain peptides, and monobodies, a ligand or peptide. In some embodiments, the inactive domain is an inactive variable heavy (iVH) or an inactive variable light (iVL) domain. The inducible protein is in a binding inactive configuration when the inhibitory or inactive domain is associated with at least one other domain of the protein, in either the first or the second polypeptide of the inducible monovalent target-binding protein, such that said binding domain is prevented from binding its target. In its binding inactive configuration neither the first polypeptide nor the second polypeptide is able to bind a target.

The at least two inactive domains each comprises at least one protease cleavage site. The protease cleavage sites are a stretch of amino acid sequences that are recognized and cleaved by any known protease, such as matrix metalloprotease (, MMP9), or furin. In some cases, an inactive domain comprising a protease cleavage site recognized by MMP9 comprises the amino acid sequence PR(S/T)(L/I)(S/T) (SEQ ID NO: 3). In some cases, an inactive domain comprising a protease cleavage site recognized by MMP9 comprises the amino acid sequence LEATA (SEQ ID NO: 4). In some cases, the protease cleavage site is recognized in a sequence-specific manner by a MMP11. In some cases, the protease cleavage site recognized by a MMP11 comprises a polypeptide having an amino acid sequence GGAANLVRGG (SEQ IN NO: 5). In some cases, the protease cleavage site is recognized by a protease disclosed in Table 1. In some cases, the protease cleavage site recognized by a protease disclosed in Table 1 comprises a polypeptide having an amino acid sequence selected from a sequence disclosed in Table 1 (SEQ ID NOS: 1-42).

Proteases are proteins that cleave proteins, in some cases, in a sequence-specific manner. Proteases include but are not limited to serine proteases, cysteine proteases, aspartate proteases, threonine proteases, glutamic acid proteases, metalloproteases, asparagine peptide lyases, serum proteases, cathepsins, Cathepsin B, Cathepsin C, Cathepsin D, Cathepsin E, Cathepsin K, Cathepsin L, kallikreins, hK1, hK10, hK15, plasmin, collagenase, Type IV collagenase, stromelysin, Factor Xa, chymotrypsin-like protease, trypsin-like protease, elastase-like protease, subtilisin-like protease, actinidain, bromelain, calpain, caspases, caspase-3, Mir1-CP, papain, HIV-1 protease, HSV protease, CMV protease, chymosin, renin, pepsin, matriptase, legumain, plasmepsin, nepenthesin, metalloexopeptidases, metalloendopeptidases, matrix metalloproteases (MMP), MMP1, MMP2, MMP3, MMP8, MMP9, MMPP13, MMP11, MMPP14, urokinase plasminogen activator (uPA), enterokinase, prostate-specific antigen (PSA, hK3), interleukin-1β converting enzyme, thrombin, FAP (FAP-α), dipeptidyl peptidase, and dipeptidyl peptidase IV (DPPIV/CD26).

TABLE 1

Exemplary Proteases and Protease Recognition Sequences

| Protease | Cleavage Domain Sequence | SEQ ID NO: |
| --- | --- | --- |
| MMP7 | KRALGLPG | 1 |
| MMP7 | (DE)$_8$RPLALWRS(DR)$_8$ | 2 |
| MMP9 | PR(S/T)(L/I)(S/T) | 3 |
| MMP9 | LEATA | 4 |
| MMP11 | GGAANLVRGG | 5 |
| MMP14 | SGRIGFLRTA | 6 |
| MMP | PLGLAG | 7 |
| MMP | PLGLAX | 8 |
| MMP | PLGC(me)AG | 9 |
| MMP | ESPAYYTA | 10 |
| MMP | RLQLKL | 11 |
| MMP | RLQLKAC | 12 |

TABLE 1-continued

Exemplary Proteases and Protease Recognition Sequences

| Protease | Cleavage Domain Sequence | SEQ ID NO: |
|---|---|---|
| MMP2, MMP9, MMP14 | EP(Cit)G(Hof)YL | 13 |
| Urokinase plasminogen activator (uPA) | SGRSA | 14 |
| Urokinase plasminogen activator (uPA) | DAFK | 15 |
| Urokinase plasminogen activator (uPA) | GGGRR | 16 |
| Lysosomal Enzyme | GFLG | 17 |
| Lysosomal Enzyme | ALAL | 18 |
| Lysosomal Enzyme | FK | 19 |
| Cathepsin B | NLL | 20 |
| Cathepsin D | PIC(Et)FF | 21 |
| Cathepsin K | GGPRGLPG | 22 |
| Prostate Specific Antigen | HSSKLQ | 23 |
| Prostate Specific Antigen | HSSKLQL | 24 |
| Prostate Specific Antigen | HSSKLQEDA | 25 |
| Herpes Simplex Virus Protease | LVLASSSFGY | 26 |
| HIV Protease | GVSQNYPIVG | 27 |
| CMV Protease | GVVQASCRLA | 28 |
| Thrombin | F(Pip)RS | 29 |
| Thrombin | DPRSFL | 30 |
| Thrombin | PPRSFL | 31 |
| Caspase-3 | DEVD | 32 |
| Caspase-3 | DEVDP | 33 |
| Caspase-3 | KGSGDVEG | 34 |
| Interleukin 1β converting enzyme | GWEHDG | 35 |
| Enterokinase | EDDDDKA | 36 |
| FAP | KQEQNPGST | 37 |
| Kallikrein 2 | GKAFRR | 38 |
| Plasmin | DAFK | 39 |
| Plasmin | DVLK | 40 |
| Plasmin | DAFK | 41 |
| TOP | ALLLALL | 42 |

Proteases are known to be secreted by some diseased cells and tissues, for example tumor or cancer cells, creating a microenvironment that is rich in proteases or a protease-rich microenvironment. In some case, the blood of a subject is rich in proteases. In some cases, cells surrounding the tumor secrete proteases into the tumor microenvironment. Cells surrounding the tumor secreting proteases include but are not limited to the tumor stromal cells, myofibroblasts, blood cells, mast cells, B cells, NK cells, regulatory T cells, macrophages, cytotoxic T lymphocytes, dendritic cells, mesenchymal stem cells, polymorphonuclear cells, and other cells. In some cases, proteases are present in the blood of a subject, for example proteases that target amino acid sequences found in microbial peptides. This feature allows for targeted therapeutics such as antigen-binding proteins to have additional specificity because T cells will not be bound by the antigen binding protein except in the protease rich microenvironment of the targeted cells or tissue.

Inducible Monovalent Target-Binding Proteins

In some embodiments, the inducible monovalent target-binding proteins described herein comprise a first and a second polypeptide chain, each polypeptide comprising an inactive variable domain, a variable heavy domain (VH) or a variable light domain (VL), and an Fc region. The inactive domain is a variable light domain (iVL) or a variable heavy domain (iVH); and the Fc region comprises a CH3 domain with amino acid substitutions, and a CH2 domain. In some embodiments, the inactive domains iVL and iVH each comprise at least one protease cleavage site which is cleaved by a protease to result in activation of the inducible monovalent target-binding proteins described herein.

In some embodiments, the first polypeptide comprises an iVL, a VH, and a first Fc domain (Fc1) comprising CH3-Fc1 and CH2-Fc1; the second polypeptide comprises an iVH, a VL, and a second Fc domain (Fc2) comprising CH3-Fc2 and CH2-Fc2, which VH and VL associate to form the target-binding domain of the inducible monovalent protein, and wherein CH3-Fc1 and CH3-Fc2 form a heterodimer, as shown in FIG. 1. In some embodiments, the first polypeptide comprises an iVH, a VL, and a first Fc domain (Fc1) comprising CH3-Fc1 and CH2-Fc1; the second polypeptide comprises an iVL, a VH, and a second Fc domain (Fc2) comprising CH3-Fc2 and CH2-Fc2, which VL and VH associate to form the target-binding domain of the inducible monovalent protein, and wherein CH3-Fc1 and CH3-Fc2 form a heterodimer.

An Fc domain conjugated to an effector molecule is referred to as an Fc domain molecule or an Fc domain fusion protein. The fusion protein can include, for example, a VH, a engineered antibody domain, a diabody, an scFv, a cytokine, a toxin, an enzyme, and/or a ligand attached an Fc domain, wherein the Fc domain comprises a CH3 and a CH2 domain. CH2 and CH3 domain molecules are small in size, usually less than 15 kD. It is contemplated that in certain embodiments the CH2 and CH3 domain molecules are conjugated to an effector molecule or a label. In other embodiments, CDRs/hypervariable amino acid sequences are inserted into the CH3 and/or CH2 domain. In such embodiments, the CH2 or CH3 domain vary in size depending on the length of CDR/hypervariable amino acid sequence inserted in the loops regions, how many CDRs are inserted and whether another molecule (such as an effector molecule or label) is conjugated to the CH2 or CH3 domain. In some embodiments, the Fc domain does not comprise additional constant domains (i.e. CH1). In one embodiment, the CH3 and/or CH2 domain is from IgG, IgA or IgD. In another embodiment, the CH3 and/or CH2 domain is from IgE or IgM. CH2 and CH3 domain molecules can be glycosylated or unglycosylated. For example, a recombinant CH2 or CH3 domain can be expressed in an appropriate mammalian cell to allow glycosylation of the molecule.

In some embodiments, the inducible monovalent target-binding protein disclosed herein is an Fc domain molecule or an Fc fusion protein. In some embodiments, the inducible monovalent target-binding domains described herein comprise a first and second monomeric Fc domains, Fc1 and Fc2, respectively, which monomeric Fc domains associate with each other to form a heterodimeric Fc domain, and wherein a first scFv (scFv1) is attached to the N-terminus of Fc1, and a second scFv (scFv2) is attached to the N-terminus of Fc2, and further wherein the scFv1 and scFv2 each comprise at least one protease cleavage site. The first monomeric Fc1 domain comprises two domains CH3-Fc1 and CH3-Fc2, and the second monomeric Fc2 domain comprises two domains CH3-Fc2 and CH2-Fc2. Each scFv1 and scFv2 comprises an inactive domain, and a variable light (VL) or variable heavy domain (VH). In some embodiments, the inactive domains are iVL and iVH, and each comprises at least one protease cleavage site which is cleaved by a protease to result in activation of the inducible monovalent target-binding proteins described in this embodiment. The protease cleavage sites of the inactive domains are, in some cases, within the complementarity determining regions of those domains; or within the linkers that connects the inactive domains iVL and iVH with the VH or VL domains, respectively.

In some embodiments, scFv1 comprises an iVH domain and a VL domain. In some embodiments, scFv1 comprises an iVL domain and a VH domain. In some embodiments, scFv2 comprises an iVH domain and a VL domain. In some embodiments, scFv2 comprises an iVL domain and a VH domain. In some embodiments, scFv1 comprises an iVL domain and a VH domain; scFv2 comprises an iVH domain and a VL domain, wherein upon cleavage of the at least one protease cleavage site in iVH and iVL the VL and VH domains associate to form an active monovalent target-binding protein. In some embodiments, scFv1 comprises an iVH domain and a VL domain; scFv2 comprises an iVL domain and a VH domain, wherein upon cleavage of the at least one protease cleavage site in iVH and iVL, the VH and VL domains associate to form an active monovalent target-binding protein.

The inactive variable domains iVL and iVH each comprises complementarity determining regions CDRL1, CDRL2, CDRL3, and CDRH1, CDRH2, CDRH3, respectively, and the at least one protease cleavage site is, in certain embodiments, located within said complementarity determining regions. It is contemplated that, in some embodiments, the CDRs of iVL and/or iVH further comprise one or more mutations that prohibit the binding of said domains to a target.

The proteins described herein are binding inactive in the two-armed form, and only bind target protein when in the monovalent form. In some embodiments, the proteins described herein do not have target-domain binding capability until at least one protease cleavage site in iVL and at least one cleavage site in iVH are cleaved by a protease and the VH and VL domains associate with each other to form a monovalent active target-binding domain. In some embodiments, the proteins do not have target-domain binding capability until all the protease cleavage sites in iVH and iVL are cleaved and the VH and VL domains associate with each other to form a monovalent active target-binding domain.

The VH and iVL domains, the VL and iVH domains, the VL and CH2 domain, the VH and CH2 domain, and the CH3 and CH2 domains are connected to each other by internal linkers. In embodiments where the first polypeptide comprises an iVL, a VH, and a first Fc domain (Fc1) comprising CH3-Fc1 and CH2-Fc1; the second polypeptide comprises an iVH, a VL, and a second Fc domain (Fc2) comprising CH3-Fc2 and CH2-Fc2, the linkers are as follows: L1 links iVL and VH of the first polypeptide; L2 links VH and CH2-Fc1; L3 links CH2-Fc1 and CH3-Fc1; L4 links CH3-Fc2 and CH2-Fc2; L5a links CH2-Fc2 and VL; and L6 links VL and iVH of the second polypeptide. In embodiments where the first polypeptide comprises an iVH, a VL, and a first Fc domain (Fc1) comprising CH3-Fc1 and CH2-Fc1; the second polypeptide comprises an iVL, a VH, and a second Fc domain (Fc2) comprising CH3-Fc2 and CH2-Fc2, the linkers are as follows: L1' links iVH and VL of the first polypeptide; L2' links VH and CH2-Fc1; L3' links CH2-Fc1 and CH3-Fc1; L4' links CH3-Fc2 and CH2-Fc2; L5' links CH2-Fc2 and VL; and L6' links VH and iVL of the second polypeptide. In some embodiments, the linkers L1, L1', L6, and L6', each independently comprises at least one protease cleavage site which is cleaved by a protease to result in activation of the inducible monovalent target-binding proteins described herein Linkers L1, L1', L2, L2', L3, L3', L4, L4', L5, L5', L6, and L6' have an optimized length and/or amino acid composition. In some embodiments, linkers L1, L1', L2, L2', L3, L3', L4, L4', L5, L5', L6, and L6' are 3-200 amino acids in length. In some embodiments, linkers L1, L1', L2, L2', L3, L3', L4, L4', L5, L5', L6, and L6' have the same length or amino acid composition. In other embodiments, linkers L1, L1', L2, L2', L3, L3', L4, L4', L5, L5', L6, and L6' have different amino acid compositions. In other embodiments, linkers L1, L1', L2, L2', L3, L3', L4, L4', L5, L5', L6, and L6' have different lengths. In certain embodiments, internal linkers L1, L2, L3, and/or L4 are "short", i.e., consist of 0, 1, 2, 3, 4, 5, 6, 7, 8, 9, 10, 11 or 12 amino acid residues. Thus, in certain instances, the linkers consist of about 12 or less amino acid residues. In the case of 0 amino acid residues, the linker is a peptide bond. In certain embodiments, linkers L1, L1', L2, L2', L3, L3', L4, L4', L5, L5', L6, and L6' consist of 15, 20 or 25 amino acid residues. In some embodiments, the linkers consist of about 3 to about 15, for example 8, 9 or 10 contiguous amino acid residues. Regarding the amino acid composition of the linkers L1, L1', L2, L2', L3, L3', L4, L4', L5, L5', L6, and L6', peptides are selected with properties that confer flexibility to the antigen-binding proteins, do not interfere with the target-binding domain as well as resist cleavage from proteases, unless the protease cleavage sites are located within the linkers. Examples of internal linkers suitable for linking the domains in the antigen-binding proteins include but are not limited to $(GS)_n$ (SEQ ID NO: 55), $(GGS)_n$ (SEQ ID NO: 56), $(GGGS)_n$ (SEQ ID NO: 57), $(GGSG)_n$ (SEQ ID NO: 58), $(GGSGG)_n$ (SEQ ID NO: 59), or $(GGGGS)_n$ (SEQ ID NO: 60), wherein n is 1, 2, 3, 4, 5, 6, 7, 8, 9, or 10. In one embodiment, internal linker L1, L1', L2, L2', L3, L3', L4, L4', L5, L5', L6, and/or L6' is $(GGGGS)_4$ (SEQ ID NO: 61) or $(GGGGS)_3$ (SEQ ID NO: 62).

In certain instances, one or more of the linkers L1, L1', L2, L2', L3, L3', L4, L4', L5, L5', L6, and L6' comprise protease cleavage sites. Such protease sensitive linkers are, in certain embodiments, sensitive to protease present in specific tissue or intracellular compartments (, MMPs, furin, cathepsin B). Example sequences for such protease sensitive cleavable linkers include but are not limited to $(PLGLWA)_n$ (SEQ ID NO: 63), $(RVLAEA)_n$ (SEQ ID NO: 64); $(EDVVCCSMSY)n$ (SEQ ID NO: 65), $(GGIEGRGS)_n$ (SEQ ID NO: 66), which are recognized by MMP-1, and $(GFLG)n$ (SEQ ID NO: 67) which are recognized by furin. The linkers containing protease cleavage sites play a role in activation of the inducible monovalent target-domain binding protein. In some embodiments, the binding protein is activated upon cleavage of the protease sites in iVL, iVH, and one or more of linkers L1, L1', L2, L2', L3, L3', L4, L4', L5, L5', L6, and L6'. In embodiments where one or more of the linkers comprise protease cleavage sites the inducible monovalent target-domain binding protein is not activated until at least one cleavage site in at least one of the linkers is cleaved.

It is contemplated that in some embodiments the inducible monovalent target-binding protein is no more than 100 kD, no more than 75 kD, no more than 50 kD, no more than 25 kD, no more than 20 kD, no more than 15 kD, or no more than 10 kD, upon its activation by protease cleavage. Prior to cleavage and activation, the inducible protein is, in certain embodiments, no more than 100 kD, no more than 75 kD, no more than 50 kD, no more than 25 kD, no more than 20 kD, or no more than 15 kD.

Fc-Domain Heterodimerization

Although the wild-type Fc region is a homodimer of polypeptides, the Fc domains disclosed herein comprise amino acid substitutions such that they do not form homodimers. The monomeric Fc domains, Fc1 and Fc2, are in some embodiments IgG Fc. In some embodiments, the monomeric Fc domains, Fc1 and Fc2, are from other immunoglobulin subclasses including IgA, IgE, IgD, and IgM.

The heterodimer Fc region of the inducible monovalent target-binding proteins described herein comprises a variant CH3 constant domain comprising amino acid mutations that promote the formation of said heterodimer with stability comparable to a native homodimeric Fc, and a CH2 constant domain. The wild-type Fc is homodimeric in nature and this feature is driven by both hydrophobic interactions at the center of the CH3 interface and symmetric electrostatic interactions around the rim of the hydrophobic core. In some embodiments, the Fc domain described herein comprises amino acid substitutions such that they do not form homodimers. In some embodiments, the Fc domain described herein comprises amino acid substitutions that favor formation of heterodimers over homodimers. In some embodiments, the variant Fc domain is created using (i) symmetric-to-asymmetric steric complementarity design (, KiH, HA-TF, and ZW1), (ii) charge-to-charge swap (, DD-KK), (iii) charge-to-steric complementarity swap plus additional long-range electrostatic interactions (, EW-RVT), and (iv) isotype strand swap [, strand-exchange engineered domain (SEED)]. Strand exchange mutations include, for example, IgA-derived 45 residues on IgG1 CH3-Fc1 and IgG1-derived 57 residues on IgA CH3-Fc2, or vice versa. Examples of symmetric-to-asymmetric sterically complementary mutations include HA-TF (S364H/F405A in Fc1-CH3 or CH3A and Y349T/T394F in Fc2-CH3 or CH3B), ZW1(T350V/L351Y/F405A/Y407V in Fc1-CH3 or CH3A and T350V/T366L/K392L/T394W in Fc2-CH3 or CH3B). In some embodiments, the Fc variant is generated using the "Knobs-into-holes (KiH)" approach where Fc1 comprises a T366W "knob" mutation, in Fc1-CH3 or CH3A, and Fc2 comprises T366S/L368A/Y407V "hole" mutations in Fc2-CH3 or CH3B domain. In some embodiments, the Fc variant is generated using the "Knobs-into-holes (KiH)" plus disulfide bond approach, $KiH_{S-S}$, where Fc1 comprises a T366W/S354C "knob" mutation, in Fc1-CH3 or CH3A, and Fc2 comprises T366S/L368A/Y407V/Y349C "hole" mutations in Fc2-CH3 or CH3B domain. In such exemplary embodiments, the heterodimerization is favored through hydrophobic interactions at the core of the Fc1-CH3 or CH3A and Fc2-CH3 or CH3B interface. Examples of charge-charge swap mutations, where the Fc heterodimer favoring interaction is based on electrostatic complementarity include DD-KK (K409D/K392D in Fc1-CH3 or CH3A and D399K/E356K in Fc2-CH3 or CH3B, or vice versa). Examples of charge-to-steric complementarity swap plus additional long-range electrostatic interaction mutations include EW-RVT (K360E/K409W in Fc1-CH3 or CH3A and Q347R/D399V/F405T in Fc2-CH3 or CH3B, or vice versa); $EW-RVT_{S-S}$ (K360E/K409W/Y349C in Fc1-CH3 or CH3A and Q347R/D399V/F405T/S354C in Fc2-CH3 or CH3B, or vice versa), which comprises an inter-CH3 S—S bond. In some embodiments, the Fc variant is generated using hydrophobic or steric complementarity plus electrostatic complementarity, such as 7.8.60 (K360D/D399M/Y407A in Fc1-CH3 or CH3A and E345R/Q347R/T366V/K409V in Fc2-CH3 or CH3B, or vice versa).

In certain embodiments, the heterodimer forming Fc variants described herein are generated through directed evolution combined with yeast surface display and high-throughput screening. For example, in some embodiments, a combinatorial heterodimeric Fc library display system is developed by mating two haploid yeast cell lines; one haploid cell line displaying an Fc chain library (CH3-Fc1 or CH3A) with mutations in one CH3 domain on the yeast cell surface, and the other cell line secreting an Fc chain library (CH3-Fc2 or CH3B) with mutations in the other CH3 domain. In the mated cells, secreted CH3-Fc2 or CH3B is displayed on the cell surface through heterodimerization with the displayed CH3-Fc1 or CH3A. Fluorescence-based detection of this interaction enables screening of the library for heterodimeric Fc variants by flow cytometry.

The Y-shape of typical IgG antibodies often limits their utility against some targets, whereby bivalent target-binding dimerizes and agonizes, rather than antagonizes, the intended targets (See, Choi et al., Engineering of Immunoglobulin Fc heterodimers using yeast surface-displayed combinatorial Fc library screening, PLOS One, 10(12): e0145349, 2015. Therefore, in some embodiments, the inducible monovalent target-binding proteins described herein are advantageously used for antagonization of binding targets. In some embodiments, the heterodimerization of the Fc1 and Fc2 domains is expected to reduce high molecular weight tetrameric by-products during preparation of the inducible monovalent target-domain binding proteins disclosed herein.

An antibody that includes a wild-type Fc domain has the ability to interact with neonatal Fc-receptor (FcRn) in a pH dependent manner; this interaction confers extended serum half-life. The residues important for the high-affinity interaction of Fc domain and FcγR are located within the CH2 domain. Accordingly, in some embodiments, CH2-Fc1 and CH2-Fc2 comprise wild type IgG sequence.

Activated Monovalent Target-Binding Protein

The inducible monovalent target-binding proteins described herein are activated by cleavage of the at least one protease cleavage site in the inactive VL domain, and the at least one protease cleavage site in the inactive VH domain. Upon protease cleavage the VH and VL target binding domains associate to form a monovalent active target-binding domain. It is contemplated that the target antigen is involved in and/or associated with a disease, disorder or condition. In particular, a target antigen associated with a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease. In some embodiments, a target antigens is a tumor antigen expressed on a tumor cell. In some embodiments, a target antigen is a on a tumor cell, virally infected cell, bacterially infected cell, damaged red blood cell, arterial plaque cell, or fibrotic tissue cell.

In some embodiments, a target antigen is a cell surface molecule such as a protein, lipid or polysaccharide. In some embodiments, a target antigen is an immune checkpoint protein.

Target antigens, in some cases, are expressed on the surface of a diseased cell or tissue, for example a tumor or a cancer cell. Examples of target antigens include but are not limited to CD19, CD20, CD33, CD30, CD64, CD123, EpCAM, EGFR, HER-2, HER-3, c-Met, LAG3, FoIR, EGFR, PSMA, VEGF, and CEA. In one aspect, a target antigen is an immune checkpoint protein. Examples of immune checkpoint proteins include but are not limited to CD27, CD40, OX40, GITR, CD137, B7, CD28, ICOS, A2AR, B7-H3, B7-H4, BTLA, CTLA-4, IDO, KIR, LAG3, PD-1, PD-L1, TIM-3, VISTA. Inhibitory immune checkpoint proteins to be inhibited in activating an immune response include but are not limited to A2AR, B7-H3, B7-H4, BTLA, CTLA-4, IDO, KIR, LAG3, PD-1, PD-L1, TIM-3, and VISTA. In some embodiments, binding of the inducible monovalent target-binding protein to an immune checkpoint target protein is dependent upon protease cleavage of the inhibitory domain which restricts binding of the protein to the immune checkpoint target protein only in the microenvironment of a diseased cell or tissue with elevated levels of proteases, for example in a tumor microenvironment.

In some embodiments, the inducible monovalent target-binding proteins described herein specifically binds to A2AR. In some embodiments, the inducible monovalent target-binding proteins described herein specifically binds to B7-H3. In some embodiments, the inducible monovalent target-binding proteins described herein specifically binds to B7-H4. In some embodiments, the inducible monovalent target-binding proteins described herein specifically binds to BTLA. In some embodiments, the inducible monovalent target-binding proteins described herein specifically binds to CTLA-4. In some embodiments, the inducible monovalent target-binding proteins described herein specifically binds to IDO. In some embodiments, the inducible monovalent target-binding proteins described herein specifically binds to KIR. In some embodiments, the inducible monovalent target-binding proteins described herein specifically binds to LAG3. In some embodiments, the inducible monovalent target-binding proteins described herein specifically binds to PD-1. In some embodiments, the inducible monovalent target-binding proteins described herein specifically binds to PD-L1. In some embodiments, the inducible monovalent target-binding proteins described herein specifically binds to TIM-3. In some embodiments, the inducible monovalent target-binding proteins described herein specifically binds to VISTA.

Binding Protein Variants

As used herein, the term "binding protein variants" refers to variants and derivatives of an inducible monovalent antibody described herein. In certain embodiments, amino acid sequence variants of the inducible antibodies described herein are contemplated. For example, in certain embodiments amino acid sequence variants of the inducible antibodies described herein are contemplated to improve the binding affinity and/or other biological properties of the antibodies. Exemplary method for preparing amino acid variants include, but are not limited to, introducing appropriate modifications into the nucleotide sequence encoding the antibody, or by peptide synthesis. Such modifications include, for example, deletions from, and/or insertions into and/or substitutions of residues within the amino acid sequences of the antibody.

Any combination of deletion, insertion, and substitution can be made to the various domains to arrive at the final construct, provided that the final construct possesses the desired characteristics, antigen-binding. In certain embodiments, antibody variants having one or more amino acid substitutions are provided. Sites of interest for substitution mutagenesis include the CDRs and framework regions. Amino acid substitutions may be introduced into the variable domains of the target-binding protein of interest and the products screened for a desired activity, retained/improved antigen binding, decreased immunogenicity, or improved antibody-dependent cell mediated cytotoxicity (ADCC) or complement dependent cytotoxicity (CDC). Both conservative and non-conservative amino acid substitutions are contemplated for preparing the antibody variants.

In another example of a substitution to create a variant inducible antibody, one or more hypervariable region residues of a parent antibody are substituted. In general, variants are then selected based on improvements in desired properties compared to a parent antibody, for example, increased affinity, reduced affinity, reduced immunogenicity, increased pH dependence of binding. For example, an affinity matured variant antibody can be generated, using phage display-based affinity maturation techniques such as those described herein and known in the field.

Substitutions can be made in hypervariable regions (HVR) of a parent inducible antibody to generate variants and variants are then selected based on binding affinity, i.e., by affinity maturation. In some embodiments of affinity maturation, diversity is introduced into the variable genes chosen for maturation by any of a variety of methods (, error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (, 4-6 residues at a time) are randomized. HVR residues involved in antigen binding may be specifically identified, e.g., using alanine scanning mutagenesis or modeling. Substitutions can be in one, two, three, four, or more sites within a parent antibody sequence.

In some embodiments, an inducible monovalent target-binding protein, as described herein comprises a VL and a VH domain with amino acid sequences corresponding to the amino acid sequence of a naturally occurring VL or VH domain, respectively, but that has been "humanized", i.e., by replacing one or more amino acid residues in the amino acid sequence of said naturally occurring VL or VH domains (and in particular in the framework sequences) by one or more of the amino acid residues that occur at the corresponding position(s) in a VL or VH domain from a conventional 4-chain antibody from a human being (, as indicated above). This can be performed in a manner known in the field, which will be clear to the skilled person, for example on the basis of the further description herein. Again, it should be noted that such humanized inducible monovalent target-binding antibodies of the disclosure are obtained in any suitable manner known per se and thus are not strictly limited to polypeptides that have been obtained using a polypeptide that comprises a naturally occurring VL and/or VH domain as a starting material. In some additional embodiments, an inducible monovalent target-binding antibody, as described herein, comprises a VL and a VH domain with amino acid sequences corresponding to the amino acid sequence of a naturally occurring VL or VH domain, respectively, but that has been "camelized", i.e., by replacing one or more amino acid residues in the amino acid sequence of a naturally occurring VL or VH domain from a conventional 4-chain antibody by one or more of the amino acid residues that occur at the corresponding position(s) in a VL or a VH domain of a heavy chain antibody. Such "camelizing" substitutions are preferably inserted at amino acid positions that form and/or are present at the VH-VL interface, and/or at the so-called Camelidae hallmark residues (see for example WO 94/04678 and Davies and Riechmann (1994 and 1996)). Preferably, the VH sequence that is used as a starting material or starting point for generating or designing the camelized single domain is preferably a VH sequence from a mammal, more preferably the VH sequence of a human being, such as a VH3 sequence. However, it should be noted that such camelized inducible monovalent antibodies of the disclosure, in certain embodiments, are obtained in any suitable manner known in the field and thus are not strictly limited to polypeptides that have been obtained using a polypeptide that comprises a naturally occurring VL and/or VH domain as a starting material. For example, both "humanization" and "camelization" is performed by providing a nucleotide sequence that encodes a naturally occurring VL and/or VH domain, respectively, and then changing, one or more codons in said nucleotide sequence in such a way that the new nucleotide sequence encodes a "humanized" or "camelized" inducible antibody, respectively. This nucleic acid can then be expressed, so as to provide the desired target-antigen binding capability. Alternatively, in other embodiments, a "humanized" or "camelized" inducible antibody is synthesized de novo using known peptide synthesis technique from the amino acid sequence of a naturally occurring antibody comprising a VL and/or VH domain. In some embodiments, a "humanized" or "camelized" inducible antibody is synthesized de novo using known peptide synthesis technique from the amino acid sequence or nucleotide sequence of a naturally occurring antibody comprising a VL and/or VH domain, respectively, a nucleotide sequence encoding the desired humanized or camelized inducible domain antibody of the disclosure, respectively, is designed and then synthesized de novo using known techniques for nucleic acid synthesis, after which the nucleic acid thus obtained is expressed in using known expression techniques, so as to provide the desired inducible antibody of the disclosure.

Other suitable methods and techniques for obtaining the inducible antibody of the disclosure and/or nucleic acids encoding the same, starting from naturally occurring sequences for VL or VH domains for example comprises combining one or more parts of one or more naturally occurring VL or VH sequences (such as one or more framework (FR) sequences and/or complementarity determining region (CDR) sequences), and/or one or more synthetic or semi-synthetic sequences, and/or a naturally occurring sequence for a CH2 domain, and a naturally occurring sequence for a CH3 domain comprising amino acid substitutions that favor formation of heterodimer over homodimer, in a suitable manner, so as to provide an inducible antibody of the disclosure or a nucleotide sequence or nucleic acid encoding the same.

Affinity Maturation

In designing binding proteins for therapeutic applications, it is desirable to create proteins that, for example, modulate a functional activity of a target, and/or improved binding proteins such as binding proteins with higher specificity and/or affinity and/or and binding proteins that are more bioavailable, or stable or soluble in particular cellular or tissue environments.

The inducible monovalent target-binding proteins described in the present disclosure exhibit improved the binding affinities towards the target binding domain, for example a tumor antigen expressed on a cell surface. In some embodiments, the inducible monovalent target-binding protein of the present disclosure is affinity matured to increase its binding affinity to the target binding domain, using any known technique for affinity-maturation (, mutagenesis, chain shuffling, CDR amino acid substitution). Amino acid substitutions may be conservative or semiconservative. For example, the amino acids glycine, alanine, valine, leucine and isoleucine can often be substituted for one another (amino acids having aliphatic side chains). Of these possible substitutions, typically glycine and alanine are used to substitute for one another since they have relatively short side chains and valine, leucine and isoleucine are used to substitute for one another since they have larger aliphatic side chains which are hydrophobic. Other amino acids which may often be substituted for one another include but are not limited to: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur-containing side chains). In some embodiments, the inducible monovalent target-binding proteins are isolated by screening combinatorial libraries, for example, by generating phage display libraries and screening such libraries for antibodies possessing the desired binding characteristics towards a target antigen, such as a tumor antigen expressed on a cell surface.

Inducible Target-Binding Protein Modifications

The binding proteins described herein encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the protein, such as a leader or secretory sequence or a sequence to block an immunogenic domain and/or for purification of the protein.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in the inducible binding proteins described herein, including the peptide backbone, the amino acid side-chains, and the amino or carboxyl termini. Certain common peptide modifications that are useful for modification of the inducible binding proteins include glycosylation, lipid attachment, sulfation, gamma-carboxylation of glutamic acid residues, hydroxylation, blockage of the amino or carboxyl group in a polypeptide, or both, by a covalent modification, and ADP-ribosylation.

In some embodiments, the inducible monovalent target-binding antibodies of the disclosure are conjugated with drugs to form antibody-drug conjugates (ADCs). In general, ADCs are used in oncology applications, where the use of antibody-drug conjugates for the local delivery of cytotoxic or cytostatic agents allows for the targeted delivery of the drug moiety to tumors, which can allow higher efficacy, lower toxicity, etc.

Polynucleotides Encoding Inducible Monovalent Target-Binding Proteins

Also provided, in some embodiments, are polynucleotide molecules encoding an inducible monovalent target-binding protein as described herein. In some embodiments, the polynucleotide molecules are provided as a DNA construct. In other embodiments, the polynucleotide molecules are provided as a messenger RNA transcript.

The polynucleotide molecules are constructed by known methods such as by combining the genes encoding the various domains of the inducible monovalent target-binding protein, operably linked to a suitable promoter, and optionally a suitable transcription terminator, and expressing it in bacteria or other appropriate expression system such as, for example CHO cells.

In some embodiments, the polynucleotide is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described inducible monovalent target-binding protein. Examples of expression vectors for expression in *E. coli* are pSKK (Le Gall et al., J Immunol Methods. (2004) 285(1): 111-27), pcDNA5 (Invitrogen) for expression in mammalian cells, PICHIAPINK™ Yeast Expression Systems (Invitrogen), BACUVANCE™ Baculovirus Expression System (GenScript).

Thus, the inducible monovalent target binding proteins as described herein, in some embodiments, are produced by introducing a vector encoding the protein as described above into a host cell and culturing said host cell under conditions whereby the protein domains are expressed, may be isolated and, optionally, further purified.

Production of Inducible Monovalent Target-Binding Proteins

Disclosed herein, in some embodiments, is a process for the production of an inducible monovalent target binding protein of the present disclosure. In some embodiments, the process comprises culturing a host transformed or transfected with a vector comprising a nucleic acid sequence encoding an inducible monovalent target binding protein under conditions allowing the expression of the an inducible monovalent target binding protein and recovering and purifying the produced protein from the culture.

In an additional embodiment is provided a process directed to improving one or more properties, affinity, stability, heat tolerance, cross-reactivity, etc., of the inducible monovalent target binding protein described herein, compared to a reference binding compound. In some embodiments, a plurality of single-substitution libraries is provided each corresponding to a different domain, or amino acid segment of the inducible monovalent target binding protein or reference binding compound such that each member of the single-substitution library encodes only a single amino acid change in its corresponding domain, or amino acid segment. Typically, this allows all of the potential substitutions in a large protein or protein binding site to be probed with a few small libraries. In some embodiments, the plurality of domains forms or covers a contiguous sequence of amino acids of the inducible monovalent target binding protein or a reference binding compound. Nucleotide sequences of different single-substitution libraries overlap with the nucleotide sequences of at least one other single-substitution library. In some embodiments, a plurality of single-substitution libraries are designed so that every member overlaps every member of each single-substitution library encoding an adjacent domain.

Binding proteins expressed from such single-substitution libraries are separately selected to obtain a subset of variants in each library which has properties at least as good as those of the reference binding compound and whose resultant library is reduced in size. Generally, the number of nucleic acids encoding the selected set of binding compounds is smaller than the number of nucleic acids encoding members of the original single-substitution library. Such properties include, but are not limited to, affinity to a target compound, stability with respect to various conditions such as heat, high or low pH, enzymatic degradation, cross-reactivity to other proteins and the like. The selected compounds from each single-substitution library are referred to herein interchangeably as "pre-candidate compounds," or "pre-candidate proteins." Nucleic acid sequences encoding the pre-candidate compounds from the separate single-substitution libraries are then shuffled in a PCR to generate a shuffled library, using PCR-based gene shuffling techniques.

An exemplary work flow of the screening process is described herein. Libraries of pre-candidate compounds are generated from single substitution libraries and selected for binding to the target protein(s), after which the pre-candidate libraries are shuffled to produce a library of nucleic acids encoding candidate compounds which, in turn, are cloned into a convenient expression vector, such as a phagemid expression system. Phage expressing candidate compounds then undergo one or more rounds of selection for improvements in desired properties, such as binding affinity to a target molecule. Target molecules may be adsorbed or otherwise attached to a surface of a well or other reaction container, or target molecules may be derivatized with a binding moiety, such as biotin, which after incubation with candidate binding compounds may be captured with a complementary moiety, such as streptavidin, bound to beads, such as magnetic beads, for washing. In exemplary selection regimens, the candidate binding compounds undergo a wash step so that only candidate compounds with very low dissociation rates from a target molecule are selected. Exemplary wash times for such embodiments are about 10 minutes, about 15 minutes, about 20 minutes, about 20 minutes, about 30 minutes, about 35 minutes, about 40 minutes, about 45 minutes, about 50 minutes, about 55 mins, about 1 hour, about 2 hours, about 3 hours, about 4 hours, about 5 hours, about 6 hours, about 7 hours, about 8 hours; or in other embodiments, about 24 hours; or in other embodiments, about 48 hours; or in other embodiments, about 72 hours. Isolated clones after selection are amplified and subjected to an additional cycle of selection or analyzed, for example by sequencing and by making comparative measurements of binding affinity towards their target, for example, by ELISA, surface plasmon resonance (SPR), bio-layer interferometry (, OCTET® system, Pall Life Sciences, ForteBio, Menlo Park, Calif.) or the like.

Pharmaceutical Compositions

Also provided, in some embodiments, are pharmaceutical compositions comprising an inducible monovalent target-binding protein described herein, a vector comprising the polynucleotide encoding the polypeptide of the inducible monovalent target binding protein or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

In some embodiments of the pharmaceutical compositions, the inducible monovalent target binding protein is encapsulated in nanoparticles. In some embodiments, the nanoparticles are fullerenes, liquid crystals, liposome, quantum dots, superparamagnetic nanoparticles, dendrimers, or nanorods. In other embodiments of the pharmaceutical compositions, the inducible monovalent target binding protein is attached to liposomes. In some instances, the inducible monovalent target binding protein is conjugated to the surface of liposomes. In some instances, the inducible monovalent target binding protein is encapsulated within the shell of a liposome. In some instances, the liposome is a cationic liposome.

The inducible monovalent target binding proteins described herein are contemplated for use as a medicament. Administration is effected by different ways, by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology and may be determined using known methods. In some embodiments, the inducible monovalent target-binding proteins described herein Methods of Treatment Also provided herein, in some embodiments, are methods and uses for stimulating the immune system of an individual in need thereof comprising administration of an inducible monovalent target binding protein herein. In some instances, the administration of the inducible monovalent target binding protein induces and/or sustains cytotoxicity towards a cell expressing a target antigen. In some instances, the cell expressing a target antigen is a cancer or tumor cell, a virally infected cell, a bacterially infected cell, an autoreactive T or B cell, damaged red blood cells, arterial plaques, or fibrotic tissue. In some embodiments, the target antigen is an immune checkpoint protein.

Also provided herein are methods and uses for a treatment of a disease, disorder or condition associated with a target antigen comprising administering to an individual in need thereof an inducible monovalent target binding protein as described herein. Diseases, disorders or conditions associated with a target antigen include, but are not limited to, viral infection, bacterial infection, auto-immune disease, transplant rejection, atherosclerosis, or fibrosis. In other embodiments, the disease, disorder or condition associated with a target antigen is a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease. In one embodiment, the disease, disorder or condition associated with a target antigen is cancer. In one instance, the cancer is a hematological cancer. In another instance, the cancer is a melanoma. In a further instance, the cancer is non-small cell lung cancer. In yet further instance, the cancer is breast cancer. In some embodiments, the inducible monovalent target-binding protein binds to an immune checkpoint protein and is administered to treat a cancer characterized by upregulation of said immune checkpoint protein. For example, the immune checkpoint protein is, in some cases, CTLA-4 and the cancer is melanoma, non-small cell lung cancer, triple negative breast cancer, or ovarian cancer.

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

In some embodiments of the methods described herein, the inducible monovalent target binding protein described herein are administered in combination with an agent for treatment of the particular disease, disorder or condition. Agents include but are not limited to, therapies involving antibodies, small molecules (, chemotherapeutics), hormones (steroidal, peptide, and the like), radiotherapies (γ-rays, X-rays, and/or the directed delivery of radioisotopes, microwaves, UV radiation and the like), gene therapies (e.g., antisense, retroviral therapy and the like) and other immunotherapies. In some embodiments, the inducible monovalent target binding protein described herein are administered in combination with anti-diarrheal agents, antiemetic agents, analgesics, opioids and/or non-steroidal anti-inflammatory agents. In some embodiments, the inducible monovalent target binding protein described herein are administered before, during, or after surgery.

According to another embodiment of the invention, kits for detecting a cancer, and for diagnosis, prognosis or monitoring are provided. The kits include the foregoing inducible monovalent target binding protein (, labeled anti-immune checkpoint protein inducible monovalent target-binding protein or antigen binding fragments thereof), and one or more compounds for detecting the label. In some embodiments, the label is selected from the group consisting of a fluorescent label, an enzyme label, a radioactive label, a nuclear magnetic resonance active label, a luminescent label, and a chromophore label.

EXAMPLES

The examples below further illustrate the described embodiments without limiting the scope of the invention.

Example 1: Treatment with Inducible Monovalent CTLA-4 Binding Antibody Attenuates Tumorigenesis and Enhances Survival C57Bl/6 mice are obtained from The Jackson Laboratory. B16F10 murine melanoma cell line is grown in Iscove's modified Dulbeco's medium supplemented with 10% FBS, 2 mM L-glutamine, and antibiotics (50 U/ml penicillin and 50 µg/ml streptomycin). Mice of 8-14 weeks of age (n=5-10) are subcutaneously inoculated with $2 \times 10^5$ B16F10 melanoma cells. Mice which do not receive the full injection, or whose injection does not result in a visible subcutaneous bleb without leakage, are not used in the experiment and sacrificed immediately.

For the treatment of B16F10 melanoma, mice are given intraperitoneal injections (i.p.) of 50 µg of inducible monovalent anti-PD-L1 antibody, or PBS (vehicle control) every other day starting day 10 after B16F10 inoculation.

Tumor measurements are taken every other day using digital calipers. Results indicate that treatment of tumor-bearing mice with the inducible monovalent CTLA-4 binding antibody results in an attenuation of tumorigenesis with a significant decrease in tumor area, and the mice show prolonged survival.

Example 2: Combination Therapies with an Inducible Monovalent CTLA-4 Binding Antibody and a Second Therapeutic Agent Show Increased Effects on Tumorigenesis Attenuation and Survival C57Bl/6 mice are obtained from The Jackson Laboratory. B16F10 murine melanoma cell line is grown in Iscove's modified Dulbeco's medium supplemented with 10% FBS, 2 mM L-glutamine, and antibiotics (50 U/ml penicillin and 50 µg/ml streptomycin).

Mice of 8-14 weeks of age (n=5-10) are subcutaneously inoculated with $2 \times 10^5$ B16F10 melanoma cells. Mice which do not receive the full injection, or whose injection does not result in a visible subcutaneous bleb without leakage, are not used in the experiment and sacrificed immediately.

Mice with tumor are injected intraperitoneally with the inducible monovalent CTLA-4 binding antibody alone, or in combination with a second therapeutic agent. Tumor measurements are taken every other day using digital calipers.

Treatment of the mice with the combination of the inducible monovalent CTLA-4 binding antibody and the second therapeutic agent results in improved attenuation of tumorigenesis with a significant decrease in tumor area, and improved survival, compared to a monotherapy with the second therapeutic agent alone.

Example 3: Inducible Monovalent CTLA-4 Binding Antibody Exhibits Reduced Specificity Towards Cell Line which Overexpresses CTLA-4 but is Protease Deficient Cells overexpressing CTLA-4 and exhibiting low expression of a matrix metalloprotease are separately incubated with an exemplary inducible monovalent CTLA-4 antibody according to the present disclosure, or a control non-inducible CTLA-4 antibody. Cells expressing normal levels of CTLA-4 and proteases are also incubated with exemplary inducible monovalent CTLA-4 antibody according to the present disclosure, or a control non-inducible CTLA-4 antibody.

Results indicate that in the absence of protease secretion, the inducible antibody of the present disclosure binds the protease expressing cells but does not bind the protease-deficient antigen expressing cells. In contrast, the control non-inducible antibody lacks the ability to selectively bind the protease expressing cells over the protease deficient ones. Thus, the exemplary inducible monovalent antibody of the present disclosure is advantageous, for example, in terms of reducing off-tumor toxicity.

Example 4: Characterization of Exemplary Inducible Monovalent Antibodies of this Disclosure Expression, Purification and Proteolytic Activation of Exemplary Inducible Monovalent Antibodies of this Disclosure Heavy and light chain sequences for four exemplary monovalent antibodies (disclosed as SEQ ID Nos. 43-50) according to this disclosure were cloned into mammalian expression vector pcDNA 3.4 (ThermoFisher) preceded by a leader sequence. Two of the four exemplary inducible monovalent antibodies were CTLA4 binding inducible monovalent antibodies, derived from parental antibodies targeting CTLA4 (ipilimumab, tremelimumab), and two were CD40 binding inducible monovalent antibodies derived from two parental antibodies targeting CD40 (dacetuzumab, selicrelumab). The CTLA4 binding inducible monovalent antibodies are referred to herein as Ipi-ProMonoMab and Treme-ProMonoMab, and the CD40 binding inducible monovalent antibodies are referred to herein as Dace-ProMonoMab and Seli-ProMonoMab. Sequences for the four exemplary inducible monovalent antibodies are provided in Table I. Each of these antibodies contained variable heavy and light domains connected by a linker comprising the sequence set forth as SEQ ID No. 51 (GSSGGSGGSGGSGLSGRSDNHGSSGT). The linker sequence is in bold font and underlined in Table I. In each of these antibody sequences, lysine residues in the Fc region of the heavy chains and aspartic acid residues in the Fc region of the light chains, are involved in forming heterodimeric Fc regions. The lysine residues (K) are underlined in bold font, Table I. The aspartic acid residues (D) are underlined in bold font, in Table I.

Expi293F cells (ThermoFisher) were maintained in suspension between 0.2 to 8E6 cells/ml in Expi293 media. Purified plasmid DNA was transfected into Expi293 cells in accordance with Expi293 Expression System Kit (ThermoFisher) protocols, and maintained for 4-6 days post transfection. Conditioned media was partially purified by affinity and desalting chromatography, polished by ion exchange chromatography, and concentrated with Amicon Ultra centrifugal filtration units (EMD Millipore). Fractions pooling and final purity were assessed by SDS-PAGE. Purified exemplary monovalent antibodies were either proteolytically activated with 40 nM recombinant human matriptase (R&D Systems) in phosphate-buffered saline (PBS) or untreated control with PBS alone for overnight at room temperature. Assessment of proteolytic activation was confirmed using SDS-PAGE.

Steady-State Affinity Measurements

The affinities of the exemplary monovalent antibodies, in the prodrug and activated forms, were measured by an ELISA assay. Briefly, target antigens, CD40 or CTLA4 (both from Acro Biosystems), were coated at 1 µg/ml in a Nunc MaxiSorp plate (ThermoFisher) for 1 hour and blocked with SuperBlock (ThermoFisher). The exemplary monovalent antibodies, whether intact or matriptase-activated, were added at concentrations ranging from 0.001 to 1000 nM, as indicated in the x-axis of each plot shown in FIG. 4, and incubated for 1 hour at room temperature. Plates were washed 3 times using PBS supplemented with 0.05% Tween-20 (PBS-T). Goat anti-human IgG-Fc-peroxidase conjugate antibody (Sigma) was used at 1:10,000 dilution in PBS-T and incubated for an additional hour. Plates were washed 3 times using PBS-T, followed by development using TMB substrate (ThermoFisher), and neutralizing with 0.1 M sulfuric acid. The resulting colorimetric assay was measured at 450 nm using SpectraMax spectrophotometer (Molecular Devices).

CD40 Signaling Assay

The agonistic activity of the CD40 binding inducible monovalent antibodies was determined using a human CD40-dependent reporter cell line assay, HEK-Blue CD40L assay (InvivoGen®), as per manufacture's protocol. Briefly, 293-Blue cells at 8000 cells per well were mixed with baseline level of CD40L at 0.1 nM and the CD40 binding inducible monovalent antibodies at the indicated concentrations, with or without the addition of mouse anti-human Fc polyclonal antibody at 20 µg/ml for crosslinking. After incubating at 37° C. for 20 hours, the supernatants were removed and mixed with QUANTI-Blue (InvivoGen®) at 1:4 ratio for 3 additional hours at 37° C. The resulting colorimetric assay was measured at 640 nm using SpectraMax spectrophotometer (Molecular Devices).

Results

Figure 3:
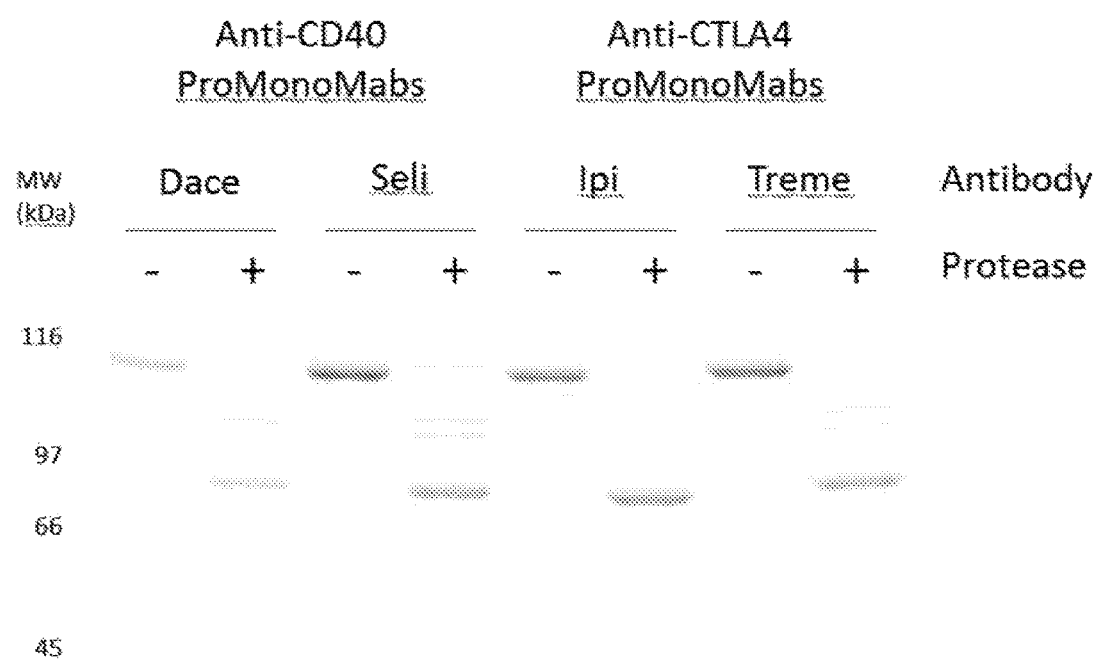
FIG. 3 shows proteolytic activation of four exemplary inducible monovalent antibodies of this disclosure, Lanes 1 and 2 correspond to Dace-ProMonoMab, Lanes 3 and 4 correspond to Seli-ProMonoMab, Lanes 5 and 6 correspond to Ipi-ProMonoMab, and Lanes 7 and 8 correspond to Treme-ProMonoMab. The lanes marked as "−" correspond to unactivated ProMonoMab and the lanes marked as "+" correspond to proteolytically activated ProMonoMab. The indicated antibodies denote parental antibodies from which the VH and VL sequences were derived. Dace, dacetuzumab; seli, selicrelumab; ipi, ipilimumab; treme, tremelimumab.

The Exemplary Inducible Monovalent Antibodies were Specifically Cleaved by a Tumor Associated Protease In Vitro The CTLA4 binding (Ipi-ProMonoMab and Treme-ProMonoMab) and CD40 binding (Dace-ProMonoMab and Seli-ProMonoMab) inducible monovalent antibodies were kept in the prodrug form by splitting the monovalent functional scFv as two separate non-binding scFvs (as shown in FIG. 2). The non-binding scFvs were kept inert by keeping the functional VH or VL domains preferentially paired with non-binding VL and VH domains, respectively, and tethered via a protease-cleavable linker. The anti-respiratory syncytial virus (RSV) F-protein antibody, palivizumab, was used as the non-binding VL and VH domains because RSV F-proteins are not normally found in healthy tissues. It was observed that all four inducible monovalent antibodies, targeting either CD40 or CTLA4, were proteolytically activated using the tumor-associated protease matriptase (as shown in FIG. 3). The SDS-PAGE confirmed that the expected molecular weights of the inducible monovalent antibodies in their prodrug forms (, 105.1 kDa for Dace-ProMonoMa, 105.9 kDa for Treme-ProMonoMab) dropped upon proteolytic cleavage when the antibodies were converted to their active forms (, in case of Dace-ProMonoMab the molecular weight dropped to about 77.7 kDa, in case of Treme-ProMonoMab the molecular weight dropped to about 78.6 kda).

Figure 4:
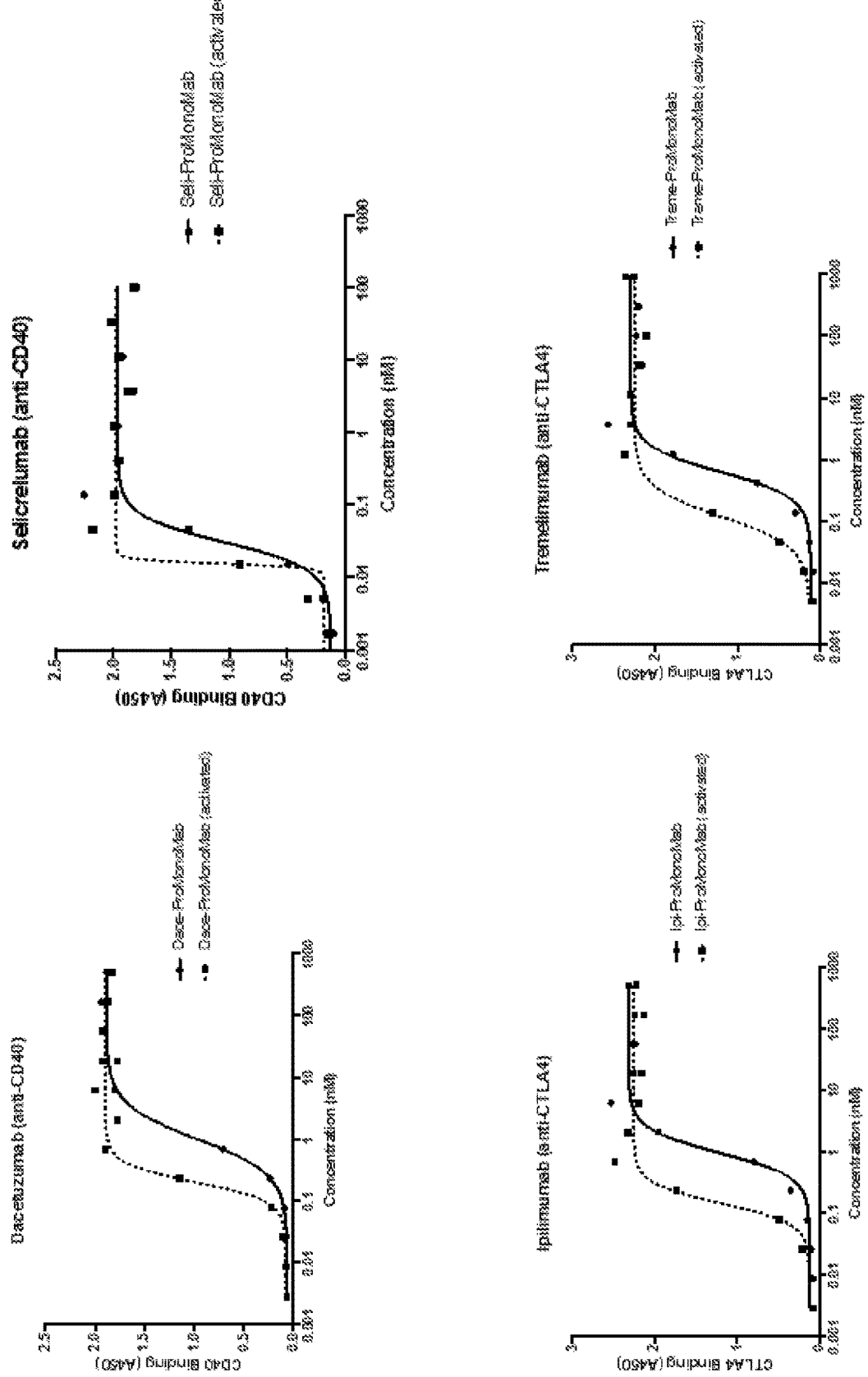
FIG. 4 shows target binding of four exemplary inducible monovalent antibodies of this disclosure. Top left panel shows CD40 binding of Dace-ProMonoMab in prodrug (dotted line) and activated (solid line) forms; top right panel shows CD40 binding of Seli-ProMonoMab in prodrug (dotted line) and activated (solid line) forms; bottom left panel shows CTLA4 binding of Ipi-ProMonoMab in prodrug (dotted line) and activated (solid line) forms; and bottom right panel shows CTLA4 binding of Treme-ProMonoMab in prodrug (dotted line) and activated (solid line) forms.

Proteolytic Activation of the Inducible Monovalent Antibodies Increases their Binding Affinity to Target Antigen Differential binding of the inducible monovalent antibodies in their prodrug and active forms was determined by comparing the apparent $K_D$ of the untreated (prodrug) or the protease-treated (active) forms of the inducible monovalent antibodies to their target antigens in an ELISA assay (results shown in FIG. 4). Differences in the apparent affinities of the inducible monovalent antibodies were 5.1× (for Dace-ProMonoMab), 2.0× (for Seli-ProMonoMab), 6.8× (for the Ipi-ProMonoMab), and 5.3× (for Treme-ProMonoMab) before and after matriptase treatment, with the matriptase-treated inducible monovalent antibody having the higher binding affinity in every instance.

Figure 5:
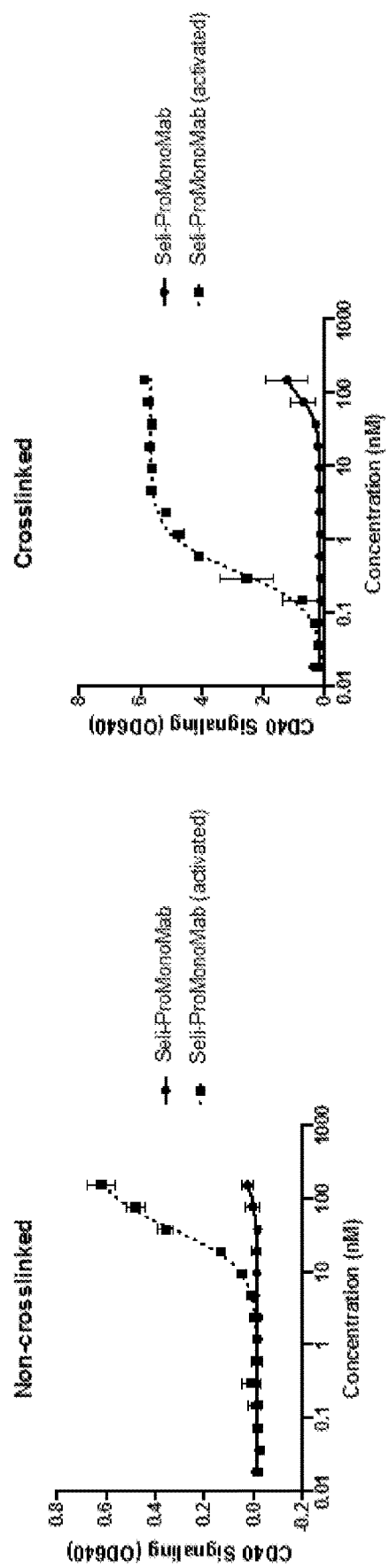
FIG. 5 shows CD40 binding of Seli-ProMonoMab upon protease activation. This assay uses HEK293 cells that are engineered to express CD40 and are also engineered to express and secrete alkaline phosphatase when CD40 is activated. The amount of secreted alkaline phosphatase is measure using a substrate that changes color proportionate to the amount of secreted alkaline phosphatase. Left panel shows CD40 activation in cells by Seli-ProMonoMab in prodrug (dotted line) and activated (solid line) forms. Right panel shows CD40 activation in cells by Seli-ProMonoMab in prodrug (dotted line) and activated (solid line) forms, crosslinked with anti-human IgG Fc polyclonal antibody.

CD40 Binding Inducible Monovalent Antibodies Demonstrated Potent CD40 Signaling after Proteolytic Activation In this experiment it was demonstrated that the inducible monovalent antibodies retain potent activity after proteolytic activation in a cell-based functional assay. In particular, the experiment determined the activity of Seli-ProMonoMab in the untreated (prodrug) or the matriptase-treated (active) forms, in a CD40-sensitive reporter cell line (results shown in FIG. 5). The engineered HEK-Blue CD40L cell line used in this method secreted alkaline phosphatase into the media in response to CD40 signaling, which was subsequently measured using a colorimetric assay. Despite a relatively small 2.0× differential affinity on ELISAs, there was a distinct and clear differential activity between the prodrug and active forms of the Seli-ProMonoMab (FIG. 5, left panel). Because anti-CD40 agonistic antibodies often depend on FcγR-mediated clustering of antibodies on cell membranes to correspondingly cluster CD40 on the opposing cell membrane, an experiment was designed to stimulate such clustering effect by adding anti-human IgG polyclonal antibodies to crosslink the Seli-ProMonoMabs. The addition of crosslinking antibodies to simulate the clustering effect on cell membranes improved the sensitivity of the cell assay, and allowed determination of a >405× differential activity. As shown in FIG. 4, $EC_{50}$ of the protease-activated form of the Seli-ProMonoMab was 0.37 nM whereas $EC_{50}$ was not reached for the untreated Seli-ProMonoMab even at the highest tested concentration of 150 nM.

TABLE I

Sequences of exemplary inducible monovalent antibodies of this disclosure

| | |
|---|---|
| Dace-ProMonoMab VH (SEQ ID No. 43) | DIQMTQSPSTLSASVGDRVTITCKCQLSVGYMHWYQQKPGKAPKLLIYDTSKLASGV PSRFSGSGSGTEFTLTISSLQPDDFATYYCFQGSGYPFTFGGGTKLEIKGSSGGSGG SGGSGLSGRSDNHGSSGTEVQLVESGGGLVQPGGSLRLSCAASGYSFTGYYTHWVRQ APGKGLEWVARVIPNAGGTSYNQKFKGRFTLSVDNSKNTAYLQMNSLRAEDTAVYYC AREGIYWWGQGTLVTVSSGGGGGDKTHTCPPCPAPELLGGPSVFLFPPKPKDTLMIS RTPEVTCVVVDVSHEDPEVKFNWYVDGVEVHNAKTKPREEQYGSTYRVVSVLTVLHQ DWLNGKEYKCKVSNKALPAPIEKTISKAKGQPREPQVYTLPPSRKEMTKNQVSLTCL VKGFYPSDIAVEWESNGQPENNYKTTPPVLKSDGSFFLYSKLTVDKSRWQQGNVFSC SVMHEALHNHYTQKSLSLSPG* |
| Dace-ProMonoMab VL (SEQ ID No. 44) | QVTLRESGPALVKPTQTLTLTCTFSGFSLSTSGMSVGWIRQPPGKALEWLADIWWDD KKDYNPSLKSRLTISKDTSKNQVVLKVTNMDPADTATYYCARSMITNWYFDVWGAGT TVTVSS GSSGGSGGSGGSGLSGRSDNHGSSGTDIQMTQSPSSLSASVGDRVTITCRSSQSLVH SNGNTFLHWYQQKPGKAPKLLIYTVSNRFSGVPSRFSGSGSGTDFTLTISSLQPEDF ATYFCSQTTHVPWTFGQGTKVEIKGGGGGDKTHTCPPCPAPELLGGPSVFLFPPKPK DTLMISRTPEVTCVVVDVSHEDPEVKFNWYVDGVEVHNAKTKPREEQYGSTYRVVSV LTVLHQDWLNGKEYKCKVSNKALPAPIEKTISKAKGQPREPQVYTLPPSREEMTKNQ VSLTCLVKGFYPSDIAVEWESNGQPENNYDTTPPVLDSDGSFFLYSDLTVDKSRWQQ GNVFSCSVMHEALHNHYTQKSLSLSPG* |
| Seli-ProMonoMab VH (SEQ ID No. 45) | DIQMTQSPSTLSASVGDRVTITCKCQLSVGYMHWYQQKPGKAPKLLIYDTSKLASGV PSRFSGSGSGTEFTLTISSLQPDDFATYYCFQGSGYPFTFGGGTKLEIKGSSGGSGG SGGSGLSGRSDNHGSSGTQVQLVQSGAEVKKPGASVKVSCKASGYTFTGYYMHWVRQ APGQGLEWMGWINPDSGGTNYAQKFQGRVTMTRDTSISTAYMELNRLRSDDTAVYYC ARDQPLGYCTNGVCSYFDYWGQGTLVTVSSGGGGGDKTHTCPPCPAPELLGGPSVFL FPPKPKDTLMISRTPEVTCVVVDVSHEDPEVKFNWYVDGVEVHNAKTKPREEQYGST YRVVSVLTVLHQDWLNGKEYKCKVSNKALPAPIEKTISKAKGQPREPQVYTLPPSRK EMTKNQVSLTCLVKGFYPSDIAVEWESNGQPENNYKTTPPVLKSDGSFFLYSKLTVD KSRWQQGNVFSCSVMHEALHNHYTQKSLSLSPG* |
| Seli-ProMonoMab VL (SEQ ID No. 46) | QVTLRESGPALVKPTQTLTLTCTFSGFSLSTSGMSVGWIRQPPGKALEWLADIWWDD KKDYNPSLKSRLTISKDTSKNQVVLKVTNMDPADTATYYCARSMITNWYFDVWGAGT TVTVSS GSSGGSGGSGGSGLSGRSDNHGSSGTDIQMTQSPSSVSASVGDRVTITCRASQGIYS WLAWYQQKPGKAPNLLIYTASTLQSGVPSRFSGSGSGTDFTLTISSLQPEDFATYYC QQANIFPLTFGGGTKVEIKGGGGGDKTHTCPPCPAPELLGGPSVFLFPPKPKDTLMI SRTPEVTCVVVDVSHEDPEVKFNWYVDGVEVHNAKTKPREEQYGSTYRVVSVLTVLH QDWLNGKEYKCKVSNKALPAPIEKTISKAKGQPREPQVYTLPPSREEMTKNQVSLTC LVKGFYPSDIAVEWESNGQPENNYDTTPPVLDSDGSFFLYSDLTVDKSRWQQGNVFS CSVMHEALHNHYTQKSLSLSPG* |
| Ipi-ProMonoMab VH (SEQ ID No. 47) | DIQMTQSPSTLSASVGDRVTITCKCQLSVGYMHWYQQKPGKAPKLLIYDTSKLASGV PSRFSGSGSGTEFTLTISSLQPDDFATYYCFQGSGYPFTFGGGTKLEIKGSSGGSGG SGGSGLSGRSDNHGSSGTQVQLVESGGGVVQPGRSLRLSCAASGFTFSSYTMHWVRQ APGKGLEWVTFISYDGNNKYYADSVKGRFTISRDNSKNTLYLQMNSLRAEDTAIYYC ARTGWLGPFDYWGQGTLVTVSSGGGGGDKTHTCPPCPAPELLGGPSVFLFPPKPKDT LMISRTPEVTCVVVDVSHEDPEVKFNWYVDGVEVHNAKTKPREEQYGSTYRVVSVLT VLHQDWLNGKEYKCKVSNKALPAPIEKTISKAKGQPREPQVYTLPPSRKEMTKNQVS LTCLVKGFYPSDIAVEWESNGQPENNYKTTPPVLKSDGSFFLYSKLTVDKSRWQQGN VFSCSVMHEALHNHYTQKSLSLSPG* |

TABLE I-continued

Sequences of exemplary inducible monovalent antibodies of this disclosure

Ipi-ProMonoMab VL
(SEQ ID No. 48)
QVTLRESGPALVKPTQTLTLTCTFSGFSLSTSGMSVGWIRQPPGKALEWLADIWWDD
KKDYNPSLKSRLTISKDTSKNQVVLKVTNMDPADTATYYCARSMITNWYFDVWGAGT
TVTVSS
GSSGGSGGSGGSGLSGRSDNHGSSGTEIVLTQSPGTLSLSPGERATLSCRASQSVGS
SYLAWYQQKPGQAPRLLIYGAFSRATGIPDRFSGSGSGTDFTLTISRLEPEDFAVYY
CQQYGSSPWTFGQGTKVEIKGGGGGDKTHTCPPCPAPELLGGPSVFLFPPKPKDTLM
ISRTPEVTCVVVDVSHEDPEVKFNWYVDGVEVHNAKTKPREEQYGSTYRVVSVLTVL
HQDWLNGKEYKCKVSNKALPAPIEKTISKAKGQPREPQVYTLPPSREEMTKNQVSLT
CLVKGFYPSDIAVEWESNGQPENNYDTTPPVLDSDGSFFLYSDLTVDKSRWQQGNVF
SCSVMHEALHNHYTQKSLSLSPG*

Treme-ProMonoMab
VH (SEQ ID No. 49)
DIQMTQSPSTLSASVGDRVTITCKCQLSVGYMHWYQQKPGKAPKLLIYDTSKLASGV
PSRFSGSGSGTEFTLTISSLQPDDFATYYCFQGSGYPFTFGGGTKLEIK**GSSGGSGG
SGGSGLSGRSDNHGSSGT**QVQLVESGGGVVQPGRSLRLSCAASGFTFSSYGMHWVRQ
APGKGLEWVAVIWYDGSNKYYADSVKGRFTISRDNSKNTLYLQMNSLRAEDTAVYYC
ARDPRGATLYYYYYGMDVWGQGTTVTVSSGGGGGDKTHTCPPCPAPELLGGPSVFLF
PPKPKDTLMISRTPEVTCVVVDVSHEDPEVKFNWYVDGVEVHNAKTKPREEQYGSTY
RVVSVLTVLHQDWLNGKEYKCKVSNKALPAPIEKTISKAKGQPREPQVYTLPPSRKE
MTKNQVSLTCLVKGFYPSDIAVEWESNGQPENNYKTTPPVLKSDGSFFLYSKLTVDK
SRWQQGNVFSCSVMHEALHNHYTQKSLSLSPG*

Treme-ProMonoMab
VL (SEQ ID No. 50)
QVTLRESGPALVKPTQTLTLTCTFSGFSLSTSGMSVGWIRQPPGKALEWLADIWWDD
KKDYNPSLKSRLTISKDTSKNQVVLKVTNMDPADTATYYCARSMITNWYFDVWGAGT
TVTVSS
GSSGGSGGSGGSGLSGRSDNHGSSGTDIQMTQSPSSLSASVGDRVTITCRASQSINS
YLDWYQQKPGKAPKLLIYAASSLQSGVPSRFSGSGSGTDFTLTISSLQPEDFATYYC
QQYYSTPFTFGPGTKVEIKGGGGGDKTHTCPPCPAPELLGGPSVFLFPPKPKDTLMI
SRTPEVTCVVVDVSHEDPEVKFNWYVDGVEVHNAKTKPREEQYGSTYRVVSVLTVLH
QDWLNGKEYKCKVSNKALPAPIEKTISKAKGQPREPQVYTLPPSREEMTKNQVSLTC
LVKGFYPSDIAVEWESNGQPENNYDTTPPVLDSDGSFFLYSDLTVDKSRWQQGNVFS
CSVMHEALHNHYTQKSLSLSPG*

What is claimed is:

1. An inducible monovalent target-binding protein, wherein the protein comprises a first polypeptide chain and a second polypeptide chain,
   - the first polypeptide chain comprising: a VH target-binding domain (VH), an inactive VL domain (iVL) that binds to the VH domain, a linker (L1), and a first monomeric Fc domain (Fc1) comprising a CH3 and a CH2 domain;
   - the second polypeptide chain comprising: a VL target-binding domain (VL), an inactive VH domain (iVH) that binds to the VL domain, a linker (L6), a second monomeric Fc domain (Fc2) comprising a CH3 and a CH2 domain;

wherein the iVL and the iVH each comprise at least one protease cleavage site, wherein upon activation by protease cleavage of the at least one protease cleavage site of both the iVL and the iVH, the VH and the VL associate to form an active target-binding domain, and wherein the CH3 domains of the Fc1 and Fc2 form a heterodimer.

2. The inducible monovalent target-binding protein of claim 1, wherein the iVL comprises a CDRL1, CDRL2, and CDRL3, and the at least one protease cleavage site of the iVL is located within the CDRL1, CDRL2, or CDRL3.

3. The inducible monovalent target-binding protein of claim 1, wherein the iVH comprises a CDRH1, CDRH2, and CDRH3, and the at least one protease cleavage site of the iVH is located within the CDRH1, CDRH2, or CDRH3.

4. The inducible monovalent target-binding protein of claim 1, wherein the first polypeptide chain comprises a further protease cleavage site, and wherein the second polypeptide comprises a further protease cleavage site.

5. The inducible monovalent target-binding protein of claim 4, wherein the further protease cleavage site of the first polypeptide chain is located within L1, and the further protease cleavage site of the second polypeptide chain is located within L6.

6. The inducible monovalent target-binding protein of claim 1, wherein the Fc1 and the Fc2 each independently comprise one or more amino acid substitutions favoring formation of a heterodimeric Fc region.

7. The inducible monovalent target-binding protein of claim 1, wherein the iVH and the iVL each are derived from an anti-respiratory syncytial virus (RSV) F-protein antibody.

8. The inducible monovalent target-binding protein of claim 1, wherein the VH, the iVL, and the L1 of the first polypeptide form a scFv.

9. The inducible monovalent target-binding protein of claim 1, wherein the VL, the iVH, and the L6 of the second polypeptide form a scFv.

10. The inducible monovalent target-binding protein of claim 1, wherein the active target-binding domain binds to a target expressed on a tumor cell.

11. The inducible monovalent target-binding protein of claim 1, wherein the active target-binding domain binds to a tumor antigen.

12. The inducible monovalent target-binding protein of claim 1, wherein the active target-binding domain binds to an immune checkpoint protein.

13. The inducible monovalent target-binding protein of claim 1, wherein the active target-binding domain binds to CD27, CD40, OX40, GITR, CD137, B7, CD28, ICOS, A2AR, B7-H3, B7-H4, BTLA, CTLA-4, IDO, KIR, LAG3, PD-1, PD-L1, TIM-3, VISTA.

14. The inducible monovalent target-binding protein of claim 1, wherein the at least one protease cleavage site of the first polypeptide and the at least one protease cleavage site is independently recognized by at least one of a serine protease, a cysteine protease, an aspartate protease, a threonine protease, a glutamic acid protease, a metalloproteinase, a gelatinase, and a asparagine peptide lyase.

15. An inducible monovalent target-binding protein, wherein the protein comprises a first polypeptide chain and a second polypeptide chain,
the first polypeptide chain comprising: a VH target-binding domain (VH), an inactive VL domain (iVL) that binds to the VH domain, a linker (L1), and a first monomeric Fc domain (Fc1) comprising a CH3 and a CH2 domain;
the second polypeptide chain comprising: a VL target-binding domain (VL), an inactive VH domain (iVH) that binds to the VL domain, a linker (L6), a second monomeric Fc domain (Fc2) comprising a CH3 and a CH2 domain;
wherein the L1 and L6 each comprise at least one protease cleavage site, wherein upon activation by protease cleavage of the at least one protease cleavage site of both L1 and L6, the VH and the VL associate to form an active target-binding domain, and wherein the CH3 domains of the Fc1 and Fc2 form a heterodimer.

16. The inducible monovalent target-binding protein of claim 15, wherein the iVH and the iVL each are derived from an anti-respiratory syncytial virus (RSV) F-protein antibody.

17. The inducible monovalent target-binding protein of claim 15, wherein the VH, the iVL, and the L1 of the first polypeptide form a scFv.

18. The inducible monovalent target-binding protein of claim 15, wherein the VL, the iVH, and the L6 of the second polypeptide form a scFv.

19. The inducible monovalent target-binding protein of claim 1, wherein the VH comprises a sequence selected from the group consisting of SEQ ID Nos. 43, 45, 47, and 49.

20. The inducible monovalent target-binding protein of claim 1, wherein the VL comprises a sequence selected from the group consisting of SEQ ID Nos. 44, 46, 48, and 50.

* * * * *